United States Patent
Selitrennikoff et al.

(10) Patent No.: US 9,333,246 B2
(45) Date of Patent: May 10, 2016

(54) COMPOSITIONS AND METHODS TO ELICIT IMMUNE RESPONSES AGAINST PATHOGENIC ORGANISMS USING YEAST-BASED VACCINES

(71) Applicant: GlobeImmune, Inc., Louisville, CO (US)

(72) Inventors: Claude P. Selitrennikoff, Highlands Ranch, CO (US); Tamara K Miller, Wheatridge, CO (US)

(73) Assignee: GlobeImmune, Inc., Louisville, CO (US)

( * ) Notice: Subject to any disclaimer, the term of this patent is extended or adjusted under 35 U.S.C. 154(b) by 230 days.

(21) Appl. No.: 13/800,094

(22) Filed: Mar. 13, 2013

(65) Prior Publication Data

US 2013/0344110 A1   Dec. 26, 2013

Related U.S. Application Data

(63) Continuation of application No. 12/570,947, filed on Sep. 30, 2009, now Pat. No. 8,460,919, which is a continuation of application No. 11/610,457, filed on Dec. 13, 2006, now abandoned.

(60) Provisional application No. 60/750,029, filed on Dec. 13, 2005, provisional application No. 60/817,300, filed on Jun. 28, 2006.

(51) Int. Cl.
   *C12N 1/00*       (2006.01)
   *A61K 39/00*      (2006.01)

(52) U.S. Cl.
   CPC ....... *A61K 39/0002* (2013.01); *A61K 2039/521* (2013.01); *A61K 2039/523* (2013.01)

(58) Field of Classification Search
   None
   See application file for complete search history.

(56) References Cited

U.S. PATENT DOCUMENTS

| | | | |
|---|---|---|---|
| 4,775,622 A | 10/1988 | Hitzeman et al. | |
| 5,310,654 A | 5/1994 | Isberg et al. | |
| 5,413,914 A | 5/1995 | Franzusoff | |
| 5,830,463 A | 11/1998 | Duke et al. | |
| 5,858,378 A | 1/1999 | Bostwick | |
| 5,919,651 A | 7/1999 | Hitzeman et al. | |
| 7,083,787 B2 | 8/2006 | Duke et al. | |
| 7,439,042 B2 | 10/2008 | Duke et al. | |
| 7,465,454 B2 | 12/2008 | Franzusoff et al. | |
| 7,563,447 B2 | 7/2009 | Franzusoff et al. | |
| 7,595,060 B2 | 9/2009 | Duke et al. | |
| 7,625,569 B2 | 12/2009 | Duke et al. | |
| 7,632,511 B2 | 12/2009 | Duke et al. | |
| 7,736,642 B2 | 6/2010 | Duke et al. | |
| 7,745,128 B2 | 6/2010 | Guo et al. | |
| 7,914,799 B2 | 3/2011 | Jira et al. | |
| 8,007,816 B2 | 8/2011 | Duke et al. | |
| 8,067,559 B2 | 11/2011 | Franzusoff et al. | |
| 8,153,136 B2 | 4/2012 | Franzusoff et al. | |
| 8,221,763 B2 | 7/2012 | Duke et al. | |
| 8,337,830 B2 | 12/2012 | Franzusoff et al. | |
| 8,343,502 B2 | 1/2013 | Franzusoff et al. | |
| 8,388,980 B2 | 3/2013 | Duke et al. | |
| 8,460,919 B2 | 6/2013 | Selitrennikoff et al. | |
| 8,470,313 B2 | 6/2013 | Guo et al. | |
| 8,501,167 B2 | 8/2013 | Apelian et al. | |
| 2002/0044948 A1 | 4/2002 | Khleif et al. | |
| 2003/0035810 A1 | 2/2003 | Caplan | |
| 2007/0172503 A1 | 7/2007 | Selitrennikoff et al. | |
| 2008/0038286 A1* | 2/2008 | Geng et al. | 424/188.1 |
| 2010/0034840 A1 | 2/2010 | Apelian et al. | |
| 2010/0189749 A1 | 7/2010 | Franzusoff et al. | |
| 2010/0196411 A1 | 8/2010 | Duke et al. | |
| 2011/0171267 A1 | 7/2011 | Bourinbaiar et al. | |

FOREIGN PATENT DOCUMENTS

| | | |
|---|---|---|
| EP | 0414404 | 2/1991 |
| FR | 2486400 | 1/1982 |
| WO | WO 2007/008780 | 1/2007 |

OTHER PUBLICATIONS

Levitz et al. Molecular characterization of a mannoprotein with homology to chitin deacetylases that stimulates T cell responses to Cryptococcus neoformans. Proc Natl Acad Sci U S A. Aug. 28, 2001;98(18):10422-7. Epub Aug. 14, 2001.*
Adams et al., International Reviews of Immunology, vol. 11, No. 2, pp. 133-141 (1994).
Allsopp et al., European Journal of Immunology, vol. 26, No. 8, pp. 1951-1959 (1996).
Asif, A.R., et al., "Proteome of Conidial Surface Associated Proteins Aspergillis fumigatus Reflecting Potential Vaccine Candidates and Allergens," J Proteome Research 2006 5 954-2.
Biondo, C. et al., "Identification and Cloning of a Cryptococcal Deacetylase that Produces Protective Immune Responses" Infection and Immunity 2002 70(5): 2383-1.
Bizzini et al., 1990, FEMS Microbiol. Immunol., 64:155-168.
Bozza, S. et al., "Dendritic Cell-Based Vaccination Against Oportunistic Fungi" Vaccine 2004 22: 857-4.
Brake et al., 1984, Proc. Natl. Acad. Sci. USA, 81:4642-4646.
Capilla et al. "Aspergillus fumigatus antigens and fungal elements as vaccines against aspergillosis in mice." In 46th Interscience Conference on Antimicrobial Agents and Chemotherapy, San Francisco, Sep. 2006, Abstract No. G-153. Washington, DC, American Society for Microbiology. Abstract Only.
Cardenas-Freytag, L. et al., "Effectiveness of a Vaccine Composed of Heat-Killed Candida albicans and a Novel Mucosal Adjuvant, LT (R192G), against Systemic Candidiasis" Infection and Immunity 1999 67(2): 826-3.

(Continued)

*Primary Examiner* — Michele K Joike
(74) *Attorney, Agent, or Firm* — Sheridan Ross P.C.

(57) ABSTRACT

Embodiments of the present invention illustrate methods of treating and preventing infection due to a pathogen such as a fungal pathogen. In particular, the present invention relates to compositions and methods for vaccinations against or treatment for a fungal organism in a non-immunocompromised or immunocompromised subject.

12 Claims, 11 Drawing Sheets

(56) References Cited

OTHER PUBLICATIONS

Casadevall, A. et al., "Polysaccharide-containing Conjugate Vaccines for Fungal Diseases" Trends in Molecular Medicine 2006 12(1): 6-9.
Cox, R.A. et al., "Coccidioidomycosis: Host Response and Vaccine Development" Clinical Microbiology Reviews 2004 17(4): 604-39.
Datta, K. et al., "Towards a Vaccine for Cryptococcus Neoformans: Principles and Caveats" FEMS Yeast Res 2006 6: 525-36.
Deepe, G.S. et al., "Preventative and Therapeutic Vaccines for Fungal Infections: From Concept to Implementation" Expert Rev. Vaccines 2004 3(6) 701-9.
Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.
Fattal-German et al., 1992, Develop. Biol. Standard., 77:115-120.
Fierer, et al., "Both CD4+ and CD8+ T Cells Can Mediate Vaccine-Induced Protection against Coccidioides immitis Infection in Mice," 2006, JID, 193:1323-1.
Franzusoff, A. et al. "Yeasts Encoding Tumour Antigens in Cancer Immunotherapy," Expert Opinion on Biological Therapy, Apr. 2005, vol. 5, No. 4, pp. 565-575.
Franzusoff et al., 1995, J. Biol. Chem., 270(7):3154-3159.
Fujita et al., Bulletin of World Health Organization, 1987, vol. 65, pp. 303-308.
Jiang, C. et al., "Role of Signal Sequence in Vaccine-Induced Protection against Experimental Coccidioidomycosis" Infection and Immunity 2002 70(7): 3330-5.
Kirkland, T.N. et al., "Molecular and Cellular Mechanisms of Protective Immunity to Coccidioidomycosis" Vaccine 2006 24: 495-500.
Klepfer et al., Archives of Virology, 1993, vol. 128, pp. 269-286.
Lu, et al., "Mutation-Selective Tumor Remission with Ras-Targeted, Whole Yeast-Based Immunotherapy," Cancer Research, 2004, vol. 64, pp. 5084-5088.
Magee, D.M. et al., "Role of B Cells in Vaccine-Induced Immunity Against Coccidioidomycosis" Infection and Immunity 2005 73(10): 7011-3.
Mansour, M.K. et al., "Protective Efficacy of Antigenic Fractions in Mouse Models of Cryptococcosis" Infection and Immunity 2004 72(3}: 1746-4.
Mashewari et al. Microconidia of Neurospora crassa. Fungal Genetics and Biol. 26: 1-18,1999.
Moore et al., "Novel yeast-based vaccine 1-40, against HIV-SF2 gp160 promotes a cytotoxic 43-62 cell response.", FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.
Orsborn, K.1. et al., "Protein Expression Profiling of Coccidioides posadasii by Two-Dimensional Differential Electrophoresis and Evaluation of a Newly Recognized Peroxisomal Matrix Protein as a Recombinant Vaccineln-Gel Candidate," 2006, Infection and Immunity, 74(3): 1865-2.
Peng, T. et al., "Localization within a Proline-Rich Antigen (Ag2/PRA) of Protective Antigenicity against Infection with Coccidioides immitis in Mice" Infection and Immunity 2002 70(7): 3330-5.
Perruccio, K. et al., "Prospects for Dendritic Cell Vaccination Against Fungal Infections in Hematopoietic Transplantation" Blood Cells, Molecules, and Diseases 2004 33: 248-5.
Rabinovich et al., 1994, Science, 265:1401-1404.
Schreuder et al., 1996 Vaccine, 14(5):383-388.
Sheppard. D.C. et al., "Development of a Vaccine for Invasive Aspergillosis" CID 2004 38: 1137-6.
Shubitz, L. et al., Protection of Mice Against Coccidioides immitis Intranasal Infection by Vaccination with Recombinant Antigen 2/PRA 2002 Infection and Immunity 70(6} 3287-9.
Sinai et al., "Enhancement of Resistance to Infectious Diseases by Oral Administration of Brewers Yeast," Infection and Immunity, vol. 9 No. 5, pp. 781-787 (May 1974).
Stevens, DA, "Vaccinate Against Aspergillosis! A Call to Arms of the Immune System" CID 2004 38: 1131-6.
Stubbs, et al., "Whole Recombinant Yeast Vaccine Activates Dendritic Cells and Elicits Protective Cell-Mediated Immunity," National Medicine, 2001, vol. 7, No. 5, pp. 1-5.
Tarcha, E.J. et al., "A Recombinant Aspartyl Protease of Coccidioides posadasii Induces Protection against Pulmonary Coccidioidomycosis in Mice" Infection and Immunity 2006 74(1) 516-27.
Timberlake et al. Genetic Engineering of Filamentous Fungi. Science 244(4910): 1313-1317,1989.
Torosantucci, A et al., "A Novel Glyco-Conjugate Vaccine Against Fungal Pathogens" JEM 2005 202(5) 597-6.
Valenzuela, et al. "Antigen engineering in yeast: Synthesis and assembly of hybrid hepatitis B surface antigen-Herpes simplex 1 gD particles", Bio/Technology, vol. 3, 323-326, Apr. 1985.
Wheeler, R.T. et al., "A Drug-Sensitive Genetic Network Masks Fungi from the Immune System" PLoS Pathogens 2006 2(4): 328-39.
Wuthrich, M. et al., "Vaccine Immunity to Pathogenic Fungi Overcomes the Requirement for CD4 Help in Exogenous Antigen Presentation to CD8+ T Cells: Implications for Vaccine Development in Immune-deficient Hosts" J.Exp. Med. 2003197(11): 1405-16.
Official Action for U.S. Appl. No. 11/610,457, mailed Apr. 6, 2009, 10 pages.
Official Action for U.S. Appl. No. 12/570,947, mailed Apr. 13, 2012 6 pages Restriction Requirement.
Office Action for U.S. Appl. No. 12/570,947, mailed Jun. 20, 2012 6 pages.
Notice of Allowance for U.S. Appl. No. 12/570,947, mailed Feb. 19, 2013 5 pages.

\* cited by examiner

Growth Curve

Fig. 6

***Cryptococcus* vaccine model**

SEQUENCE LISTING

```
<160> NUMBER OF SEQ ID NOS: 41

<210> SEQ ID NO 1
<211> LENGTH: 36
<212> TYPE: DNA
<213> ORGANISM: Artificial
```

```
<220> FEATURE:
<223> OTHER INFORMATION: empty vector control sequence
<220> FEATURE:
<221> NAME/KEY: CDS
<222> LOCATION: (1)..(36)

<400> SEQUENCE: 1 atg gaa cag aag ttg att tcc gaa gaa gac ctc gag                    36
Met Glu Gln Lys Leu Ile Ser Glu Glu Asp Leu Glu
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic Construct

<400> SEQUENCE: 2

Met Glu Gln Lys Leu Ile Ser Glu Glu Asp Leu Glu
1               5                   10

<210> SEQ ID NO 3
<211> LENGTH: 885
<212> TYPE: DNA
<213> ORGANISM: Aspergillus fumigatus
<220> FEATURE:
<221> NAME/KEY: CDS
<222> LOCATION: (1)..(885)

<400> SEQUENCE: 3 atg ctt gtg gcc acc ctc cct acc tcc ccc gtc ccc atc gcg gcg cga    48
Met Leu Val Ala Thr Leu Pro Thr Ser Pro Val Pro Ile Ala Ala Arg
1               5                   10                  15 gca acc ccc cac gaa ccc gtc ttc ttc tcc tgg gac gct ggc gcg gtg    96
Ala Thr Pro His Glu Pro Val Phe Phe Ser Trp Asp Ala Gly Ala Val
            20                  25                  30 acc tcg ttc ccc atc cac tcc agc tgc aat gcg acc cag cgc cgg cag   144
Thr Ser Phe Pro Ile His Ser Ser Cys Asn Ala Thr Gln Arg Arg Gln
        35                  40                  45 atc gag gcc ggc ctg aac gag gcg gtc gag ctc gcc cgg cac gcc aag   192
Ile Glu Ala Gly Leu Asn Glu Ala Val Glu Leu Ala Arg His Ala Lys
    50                  55                  60 gcc cac atc ctc cgc tgg ggc aac gag agc gag atc tac cgg aag tac   240
Ala His Ile Leu Arg Trp Gly Asn Glu Ser Glu Ile Tyr Arg Lys Tyr
65                  70                  75                  80 ttt ggc aac cgg ccc acc atg gag gcc gtc ggt gcc tac gat gtc atc   288
Phe Gly Asn Arg Pro Thr Met Glu Ala Val Gly Ala Tyr Asp Val Ile
                85                  90                  95 gtg aac ggg gac aag gcc aac gtg ctc ttc cgg tgt gac aac ccc gac   336
Val Asn Gly Asp Lys Ala Asn Val Leu Phe Arg Cys Asp Asn Pro Asp
            100                 105                 110 ggc aac tgt gct ttg gaa ggc tgg ggc ggc cac tgg cgc ggc gcg aac   384
Gly Asn Cys Ala Leu Glu Gly Trp Gly Gly His Trp Arg Gly Ala Asn
        115                 120                 125 gcc acc tcc gaa acc gtc atc tgt gat cgc agc tac acc acc cgc cgc   432
Ala Thr Ser Glu Thr Val Ile Cys Asp Arg Ser Tyr Thr Thr Arg Arg
    130                 135                 140 tgg ctt gtc tcc atg tgc tcc cag ggc tac acc gtc gcc ggc tcc gag   480
Trp Leu Val Ser Met Cys Ser Gln Gly Tyr Thr Val Ala Gly Ser Glu
145                 150                 155                 160 acc aac acc ttc tgg gct tcg gac ctg atg cac cgt ctg tac cat gtg   528
Thr Asn Thr Phe Trp Ala Ser Asp Leu Met His Arg Leu Tyr His Val
                165                 170                 175
```

```
cct gct gtg ggt caa ggc cgg gtc gac cac ttc gcc gac ggc tac gac      576
Pro Ala Val Gly Gln Gly Arg Val Asp His Phe Ala Asp Gly Tyr Asp
        180                 185                 190 gag gtg att gcc ctg gcc aag agc aac ggc acc gag tcc acg cat gac      624
Glu Val Ile Ala Leu Ala Lys Ser Asn Gly Thr Glu Ser Thr His Asp
            195                 200                 205 tcg gag gcg ttg cag tat ttc gcc ctt gag gcg tat gcg ttt gat att      672
Ser Glu Ala Leu Gln Tyr Phe Ala Leu Glu Ala Tyr Ala Phe Asp Ile
    210                 215                 220 gcc gct ccc ggt gtc gga tgt gct ggc gag agt cac ggc cct gac cag      720
Ala Ala Pro Gly Val Gly Cys Ala Gly Glu Ser His Gly Pro Asp Gln
225                 230                 235                 240 gga cat gac acc ggg tct gcc tcg gcg cct gcg tct acc tcc acc tct      768
Gly His Asp Thr Gly Ser Ala Ser Ala Pro Ala Ser Thr Ser Thr Ser
                245                 250                 255 agc tcc agc tcg ggc tcg ggc tcg ggc gcc acg act acc ccg acg gat      816
Ser Ser Ser Ser Gly Ser Gly Ser Gly Ala Thr Thr Thr Pro Thr Asp
            260                 265                 270 tct ccc agt gcc act att gat gtg ccg tcg aac tgc cat acc cat gaa      864
Ser Pro Ser Ala Thr Ile Asp Val Pro Ser Asn Cys His Thr His Glu
    275                 280                 285 ggt gga cag ctt cat tgc act                                          885
Gly Gly Gln Leu His Cys Thr
290                 295

<210> SEQ ID NO 4
<211> LENGTH: 295
<212> TYPE: PRT
<213> ORGANISM: Aspergillus fumigatus

<400> SEQUENCE: 4

Met Leu Val Ala Thr Leu Pro Thr Ser Pro Val Pro Ile Ala Ala Arg
1               5                   10                  15

Ala Thr Pro His Glu Pro Val Phe Phe Ser Trp Asp Ala Gly Ala Val
            20                  25                  30

Thr Ser Phe Pro Ile His Ser Ser Cys Asn Ala Thr Gln Arg Arg Gln
        35                  40                  45

Ile Glu Ala Gly Leu Asn Glu Ala Val Glu Leu Ala Arg His Ala Lys
    50                  55                  60

Ala His Ile Leu Arg Trp Gly Asn Glu Ser Glu Ile Tyr Arg Lys Tyr
65                  70                  75                  80

Phe Gly Asn Arg Pro Thr Met Glu Ala Val Gly Ala Tyr Asp Val Ile
                85                  90                  95

Val Asn Gly Asp Lys Ala Asn Val Leu Phe Arg Cys Asp Asn Pro Asp
            100                 105                 110

Gly Asn Cys Ala Leu Glu Gly Trp Gly His Trp Arg Gly Ala Asn
        115                 120                 125

Ala Thr Ser Glu Thr Val Ile Cys Asp Arg Ser Tyr Thr Thr Arg Arg
    130                 135                 140

Trp Leu Val Ser Met Cys Ser Gln Gly Tyr Thr Val Ala Gly Ser Glu
145                 150                 155                 160

Thr Asn Thr Phe Trp Ala Ser Asp Leu Met His Arg Leu Tyr His Val
                165                 170                 175

Pro Ala Val Gly Gln Gly Arg Val Asp His Phe Ala Asp Gly Tyr Asp
            180                 185                 190

Glu Val Ile Ala Leu Ala Lys Ser Asn Gly Thr Glu Ser Thr His Asp
        195                 200                 205
```

Ser Glu Ala Leu Gln Tyr Phe Ala Leu Glu Ala Tyr Ala Phe Asp Ile
    210                 215                 220

Ala Ala Pro Gly Val Gly Cys Ala Gly Glu Ser His Gly Pro Asp Gln
225                 230                 235                 240

Gly His Asp Thr Gly Ser Ala Ser Ala Pro Ala Ser Thr Ser Thr Ser
                245                 250                 255

Ser Ser Ser Ser Gly Ser Gly Ser Gly Ala Thr Thr Thr Pro Thr Asp
            260                 265                 270

Ser Pro Ser Ala Thr Ile Asp Val Pro Ser Asn Cys His Thr His Glu
        275                 280                 285

Gly Gly Gln Leu His Cys Thr
    290                 295

<210> SEQ ID NO 5
<211> LENGTH: 438
<212> TYPE: DNA
<213> ORGANISM: Aspergillus fumigatus

<400> SEQUENCE: 5
accaacacct tctgggcttc ggacctgatg caccgtctgt accatgtgcc tgctgtgggt      60
caaggccggg tcgaccactt cgccgacggc tacgacgagg tgattgccct ggccaagagc     120
aacggcaccg agtccacgca tgactcggag gcgttgcagt atttcgccct tgaggcgtat     180
gcgtttgata ttgccgctcc cggtgtcgga tgtgctggcg agagtcacgg ccctgaccag     240
ggacatgaca ccgggtctgc ctcggcgcct gcgtctacct ccacctctag ctccagctcg     300
ggctcgggct cgggcgccac gactaccccg acggattctc ccagtgccac tattgatgtg     360
ccgtcgaact gccataccca tgaaggtgga cagcttcatt gcactgaaca gaagttgatt     420
tccgaagaag acctcgag                                                    438

<210> SEQ ID NO 6
<211> LENGTH: 438
<212> TYPE: DNA
<213> ORGANISM: Aspergillus fumigatus

<400> SEQUENCE: 6
accaacacct tctgggcttc ggacctgatg caccgtctgt accatgtgcc tgctgtgggt      60
caaggccggg tcgaccactt cgccgacggc tacgacgagg tgattgccct ggccaagagc     120
aacggcaccg agtccacgca tgactcggag gcgttgcagt atttcgccct tgaggcgtat     180
gcgtttgata ttgccgctcc cggtgtcgga tgtgctggcg agagtcacgg ccctgaccag     240
ggacatgaca ccgggtctgc ctcggcgcct gcgtctacct ccacctctag ctccagctcg     300
ggctcgggct cgggcgccac gactaccccg acggattctc ccagtgccac tattgatgtg     360
ccgtcgaact gccataccca tgaaggtgga cagcttcatt gcactgaaca gaagttgatt     420
tccgaagaag acctcgag                                                    438

<210> SEQ ID NO 7
<211> LENGTH: 393
<212> TYPE: DNA
<213> ORGANISM: Aspergillus fumigatus
<220> FEATURE:
<221> NAME/KEY: CDS
<222> LOCATION: (1)..(393)

<400> SEQUENCE: 7

```
atg gca tcg gtc caa gct tac gca cag tgg gtt acg gtt cat ctc atc      48
Met Ala Ser Val Gln Ala Tyr Ala Gln Trp Val Thr Val His Leu Ile
1               5                   10                  15 aat agc atg tct tcc gag acc ttg agt atc aag aat gct agt ctc tcc      96
Asn Ser Met Ser Ser Glu Thr Leu Ser Ile Lys Asn Ala Ser Leu Ser
            20                  25                  30 tgg ggc aag tgg tac aag gac ggt gac aag gac gcc gaa atc aca agt      144
Trp Gly Lys Trp Tyr Lys Asp Gly Asp Lys Asp Ala Glu Ile Thr Ser
        35                  40                  45 gaa gat gtc cag caa aag acg gca ccc cca ggc ggt tcc gtg aac gtc      192
Glu Asp Val Gln Gln Lys Thr Ala Pro Pro Gly Gly Ser Val Asn Val
50                  55                  60 aac tct tgc ggt cgc agc gac gct tcg agt gga acg acg gga ggt ttt      240
Asn Ser Cys Gly Arg Ser Asp Ala Ser Ser Gly Thr Thr Gly Gly Phe
65                  70                  75                  80 gat ttg tat gac ggc aat acc aag att gga aga gtc cac tgg gac tgt      288
Asp Leu Tyr Asp Gly Asn Thr Lys Ile Gly Arg Val His Trp Asp Cys
                85                  90                  95 cca tgg ggt tct aaa acc aac gat ttc gat gtt gga gag aga aac aaa      336
Pro Trp Gly Ser Lys Thr Asn Asp Phe Asp Val Gly Glu Arg Asn Lys
            100                 105                 110 aat tac tgg gtc gaa att gga acg tgg aac aag tat ggt ggt gcc att      384
Asn Tyr Trp Val Glu Ile Gly Thr Trp Asn Lys Tyr Gly Gly Ala Ile
        115                 120                 125 ggc aac tgt                                                          393
Gly Asn Cys
    130
```

<210> SEQ ID NO 8
<211> LENGTH: 131
<212> TYPE: PRT
<213> ORGANISM: Aspergillus fumigatus

<400> SEQUENCE: 8

```
Met Ala Ser Val Gln Ala Tyr Ala Gln Trp Val Thr Val His Leu Ile
1               5                   10                  15

Asn Ser Met Ser Ser Glu Thr Leu Ser Ile Lys Asn Ala Ser Leu Ser
            20                  25                  30

Trp Gly Lys Trp Tyr Lys Asp Gly Asp Lys Asp Ala Glu Ile Thr Ser
        35                  40                  45

Glu Asp Val Gln Gln Lys Thr Ala Pro Pro Gly Gly Ser Val Asn Val
50                  55                  60

Asn Ser Cys Gly Arg Ser Asp Ala Ser Ser Gly Thr Thr Gly Gly Phe
65                  70                  75                  80

Asp Leu Tyr Asp Gly Asn Thr Lys Ile Gly Arg Val His Trp Asp Cys
                85                  90                  95

Pro Trp Gly Ser Lys Thr Asn Asp Phe Asp Val Gly Glu Arg Asn Lys
            100                 105                 110

Asn Tyr Trp Val Glu Ile Gly Thr Trp Asn Lys Tyr Gly Gly Ala Ile
        115                 120                 125

Gly Asn Cys
    130
```

<210> SEQ ID NO 9
<211> LENGTH: 426
<212> TYPE: DNA
<213> ORGANISM: Aspergillus fumigatus

<400> SEQUENCE: 9

```
atggcatcgg tccaagctta cgcacagtgg gttacggttc atctcatcaa tagcatgtct    60
tccgagacct tgagtatcaa gaatgctagt ctctcctggg gcaagtggta caaggacggt   120
gacaaggacg ccgaaatcac aagtgaagat gtccagcaaa agacggcacc cccaggcggt   180
tccgtgaacg tcaactcttg cggtcgcagc gacgcttcga gtggaacgac gggaggtttt   240
gatttgtatg acggcaatac caagattgga agagtccact gggactgtcc atggggttct   300
aaaaccaacg atttcgatgt tggagagaga aacaaaaatt actgggtcga aattggaacg   360
tggaacaagt atggtggtgc cattggcaac tgtgaacaga agttgatttc gaagaagac    420
ctcgag                                                              426
```

<210> SEQ ID NO 10
<211> LENGTH: 426
<212> TYPE: DNA
<213> ORGANISM: Aspergillus fumigatus

<400> SEQUENCE: 10

```
atggcatcgg tccaagctta cgcacagtgg gttacggttc atctcatcaa tagcatgtct    60
tccgagacct tgagtatcaa gaatgctagt ctctcctggg gcaagtggta caaggacggt   120
gacaaggacg ccgaaatcac aagtgaagat gtccagcaaa agacggcacc cccaggcggt   180
tccgtgaacg tcaactcttg cggtcgcagc gacgcttcga gtggaacgac gggaggtttt   240
gatttgtatg acggcaatac caagattgga agagtccact gggactgtcc atggggttct   300
aaaaccaacg atttcgatgt tggagagaga aacaaaaatt actgggtcga aattggaacg   360
tggaacaagt atggtggtgc cattggcaac tgtgaacaga agttgatttc gaagaagac    420
ctcgag                                                              426
```

<210> SEQ ID NO 11
<211> LENGTH: 523
<212> TYPE: DNA
<213> ORGANISM: Artificial
<220> FEATURE:
<223> OTHER INFORMATION: vector

<400> SEQUENCE: 11

```
atcmgsttmg caaaagtmta cmacgcaata tggattgtca gaatmtataa aagagaagca    60
aataactcct tgtcttgtat caattgcatt ataatatctt cttgttagtg caatatcata   120
tagaagtcat cgaaatagat attaagaaaa acaaactgta caatcaatca tcacatcaat   180
catcacataa aatattcagc gaattggatc catggaacag aagttgattt ccgaagaaga   240
cctcgagtga taagaattca ttaacttcca aaatgaaggt catgagtgcc aatgccaatg   300
tggtagctgc aaaaataatg aacaatgcca aaatcatgt agctgcccaa cggggtgtaa    360
cagcgacgac aaatgcccct gcggtaacaa gtctgaagaa accaagaagt catgctgctc   420
tgggaaatga acgaatagt ctttaatata ttcatctaac tatttgctgt ttttaatttt    480
taaaaggaga aggaagttta atcgacgatt ctactcagtt tga                    523
```

<210> SEQ ID NO 12
<211> LENGTH: 582
<212> TYPE: DNA
<213> ORGANISM: Coccidioides spp.
<220> FEATURE:
<221> NAME/KEY: CDS
<222> LOCATION: (1)..(582)

<400> SEQUENCE: 12

```
atg cag ttc tct cac gct ctc atc gct ctc gtc gct gcc ggc ctc gcc      48
Met Gln Phe Ser His Ala Leu Ile Ala Leu Val Ala Ala Gly Leu Ala
1               5                   10                  15 agt gcc cag ctc cca gac atc cca cct tgc gct ctc aac tgc ttc gtt      96
Ser Ala Gln Leu Pro Asp Ile Pro Pro Cys Ala Leu Asn Cys Phe Val
            20                  25                  30 gag gct ctc ggc aac gat ggc tgc act cgc ttg acc gac ttc aag tgc     144
Glu Ala Leu Gly Asn Asp Gly Cys Thr Arg Leu Thr Asp Phe Lys Cys
        35                  40                  45 cac tgc tcc aag cct gag ctc cca gga cag atc act cct tgc gtt gag    192
His Cys Ser Lys Pro Glu Leu Pro Gly Gln Ile Thr Pro Cys Val Glu
    50                  55                  60 gag gcc tgc cct ctc gac gcc cgt atc tcc gtc tcc aac atc gtc gtt    240
Glu Ala Cys Pro Leu Asp Ala Arg Ile Ser Val Ser Asn Ile Val Val
65                  70                  75                  80 gac cag tgc tcc aag gcc ggt gtc cca att gac atc cca cca gtt gac    288
Asp Gln Cys Ser Lys Ala Gly Val Pro Ile Asp Ile Pro Pro Val Asp
                85                  90                  95 acc acc gcc gct ccc gag cca tcc gag acc gct gag ccc acc gct gag    336
Thr Thr Ala Ala Pro Glu Pro Ser Glu Thr Ala Glu Pro Thr Ala Glu
            100                 105                 110 cca acc gag gag ccc act gcc gag cct acc gct gag ccc acc gct gag    384
Pro Thr Glu Glu Pro Thr Ala Glu Pro Thr Ala Glu Pro Thr Ala Glu
        115                 120                 125 ccg act tca gag ccc acc gag gag ccc act gcc gtc cca acc ggc act    432
Pro Thr Ser Glu Pro Thr Glu Glu Pro Thr Ala Val Pro Thr Gly Thr
    130                 135                 140 ggc ggt ggt gtc ccc act ggc acc ggt tcc ttc acc gtc act ggc aga    480
Gly Gly Gly Val Pro Thr Gly Thr Gly Ser Phe Thr Val Thr Gly Arg
145                 150                 155                 160 cca act gcc tcc acc cca gct gag ttc cca ggt gct ggc tcc aac gtc    528
Pro Thr Ala Ser Thr Pro Ala Glu Phe Pro Gly Ala Gly Ser Asn Val
                165                 170                 175 cgt gcc agc gtt ggc ggc att gct gct gct ctc ctc ggt ctc gct gcc    576
Arg Ala Ser Val Gly Gly Ile Ala Ala Ala Leu Leu Gly Leu Ala Ala
            180                 185                 190 tac ctg                                                             582
Tyr Leu
```

<210> SEQ ID NO 13
<211> LENGTH: 194
<212> TYPE: PRT
<213> ORGANISM: Coccidioides spp.

<400> SEQUENCE: 13

```
Met Gln Phe Ser His Ala Leu Ile Ala Leu Val Ala Ala Gly Leu Ala
1               5                   10                  15

Ser Ala Gln Leu Pro Asp Ile Pro Pro Cys Ala Leu Asn Cys Phe Val
            20                  25                  30

Glu Ala Leu Gly Asn Asp Gly Cys Thr Arg Leu Thr Asp Phe Lys Cys
        35                  40                  45

His Cys Ser Lys Pro Glu Leu Pro Gly Gln Ile Thr Pro Cys Val Glu
    50                  55                  60

Glu Ala Cys Pro Leu Asp Ala Arg Ile Ser Val Ser Asn Ile Val Val
65                  70                  75                  80
```

```
Asp Gln Cys Ser Lys Ala Gly Val Pro Ile Asp Ile Pro Pro Val Asp
                85                  90                  95

Thr Thr Ala Ala Pro Glu Pro Ser Glu Thr Ala Glu Pro Thr Ala Glu
            100                 105                 110

Pro Thr Glu Glu Pro Thr Ala Glu Pro Thr Ala Glu Pro Thr Ala Glu
        115                 120                 125

Pro Thr Ser Glu Pro Thr Glu Glu Pro Thr Ala Val Pro Thr Gly Thr
    130                 135                 140

Gly Gly Gly Val Pro Thr Gly Thr Gly Ser Phe Thr Val Thr Gly Arg
145                 150                 155                 160

Pro Thr Ala Ser Thr Pro Ala Glu Phe Pro Gly Ala Gly Ser Asn Val
                165                 170                 175

Arg Ala Ser Val Gly Gly Ile Ala Ala Ala Leu Leu Gly Leu Ala Ala
            180                 185                 190

Tyr Leu

<210> SEQ ID NO 14
<211> LENGTH: 582
<212> TYPE: DNA
<213> ORGANISM: Coccidioides spp.

<400> SEQUENCE: 14
atgcagttct ctcacgctct catcgctctc gtcgctgccg gcctcgccag tgcccagctc      60
ccagacatcc caccttgcgc tctcaactgc ttcgttgagg ctctcggcaa cgatggctgc     120
actcgcttga ccgacttcaa gtgccactgc tccaagcctg agctcccagg acagatcact     180
ccttgcgttg aggaggcctg ccctctcgac gcccgtatct ccgtctccaa catcgtcgtt     240
gaccagtgct ccaaggccgg tgtcccaatt gacatcccac cagttgacac caccgccgct     300
cccgagccat ccgagaccgc tgagcccacc gctgagccaa ccgaggagcc cactgccgag     360
cctaccgctg agcccaccgc tgagccgact catgagccca ccgaggagcc cactgccgtc     420
ccaaccggca ctggcggtgg tgtccccact ggcaccggtt ccttcaccgt cactggcaga     480
ccaactgcct ccaccccagc tgagttccca ggtgctggct ccaacgtccg tgccagcgtt     540
ggcggcattg ctgctgctct cctcggtctc gctgcctacc tg                        582

<210> SEQ ID NO 15
<211> LENGTH: 582
<212> TYPE: DNA
<213> ORGANISM: Coccidioides spp.

<400> SEQUENCE: 15
atgcagttct ctcacgctct catcgctctc gtcgctgccg gcctcgccag tgcccagctc      60
ccagacatcc caccttgcgc tctcaactgc ttcgttgagg ctctcggcaa cgatggctgc     120
actcgcttga ccgacttcaa gtgccactgc tccaagcctg agctcccagg acagatcact     180
ccttgcgttg aggaggcctg ccctctcgac gcccgtatct ccgtctccaa catcgtcgtt     240
gaccagtgct ccaaggccgg tgtcccaatt gacatcccac cagttgacac caccgccgct     300
cccgagccat ccgagaccgc tgagcccacc gctgagccaa ccgaggagcc cactgccgag     360
cctaccgctg agcccaccgc tgagccgact catgagccca ccgaggagcc cactgccgtc     420
ccaaccggca ctggcggtgg tgtccccact ggcaccggtt ccttcaccgt cactggcaga     480
ccaactgcct ccaccccagc tgagttccca ggtgctggct ccaacgtccg tgccagcgtt     540
ggcggcattg ctgctgctct cctcggtctc gctgcctacc tg                        582
```

<210> SEQ ID NO 16
<211> LENGTH: 747
<212> TYPE: DNA
<213> ORGANISM: Coccidioides spp.
<220> FE

<400> SEQUENCE: 17

Met Lys Phe Ile Thr Ser Leu Phe Ala Val Leu Ala Ile Leu Ser Ser
1               5                   10                  15

Val Ser Ala Ser Pro Thr Met Lys Lys Arg Ala Thr Val Glu Thr Ile
            20                  25                  30

Asn Asn Cys Asn Gln Gln Gly Thr Val Ala Leu Thr Phe Asp Asp Gly
        35                  40                  45

Pro Tyr Asn Tyr Glu Ala Gln Val Ala Ser Ala Leu Asp Gly Gly Lys
    50                  55                  60

Gly Thr Phe Phe Leu Asn Gly Ala Asn Tyr Val Cys Ile Tyr Asp Lys
65                  70                  75                  80

Ala Asp Glu Ile Arg Ala Leu Tyr Asp Ala Gly His Thr Leu Gly Ser
                85                  90                  95

His Thr Trp Ser His Ala Asp Leu Thr Gln Leu Asp Glu Ser Gly Ile
            100                 105                 110

Asn Glu Glu Leu Ser Lys Val Glu Asp Ala Phe Val Lys Ile Leu Gly
        115                 120                 125

Val Lys Pro Arg Tyr Phe Arg Pro Tyr Gly Asn Ile Asn Asp Asn
    130                 135                 140

Val Leu Asn Val Leu Ser Glu Arg Gly Tyr Thr Lys Val Phe Leu Trp
145                 150                 155                 160

Ser Asp Asp Thr Gly Asp Ala Asn Gly Glu Ser Val Ser Tyr Ser Glu
                165                 170                 175

Gly Val Leu Asp Asn Val Ile Gln Asp Tyr Pro Asn Pro His Leu Val
            180                 185                 190

Leu Asp His Ser Thr Ile Glu Thr Thr Ser Ser Glu Val Leu Pro Tyr
        195                 200                 205

Ala Val Pro Lys Leu Gln Ser Ala Gly Tyr Gln Leu Val Thr Val Gly
    210                 215                 220

Glu Cys Leu Gly Thr Asp Glu Ser Pro Tyr Glu Trp Val Asp Cys Pro
225                 230                 235                 240

Gly Glu Arg Asp Ser Ser Trp Gln Cys
                245

<210> SEQ ID NO 18
<211> LENGTH: 1872
<212> TYPE: DNA
<213> ORGANISM: Artificial
<220> FEATURE:
<223> OTHER INFORMATION: plasmid with Laccase
<220> FEATURE:
<221> NAME/KEY: CDS
<222> LOCATION: (1)..(1872)

<400> SEQUENCE: 18 atg cgg gga gta gtc aag ctc ttc ttt cta tct tgt tcc ctc gtt tcg    48
Met Arg Gly Val Val Lys Leu Phe Phe Leu Ser Cys Ser Leu Val Ser
1               5                   10                  15 ctg gtc agc agc gag gag act ggc aag tcg cca acc gcg aac tat gac    96
Leu Val Ser Ser Glu Glu Thr Gly Lys Ser Pro Thr Ala Asn Tyr Asp
            20                  25                  30 cat tat atg ccg aag gcg aca gca acc att gat cct agt gta ttc gct   144
His Tyr Met Pro Lys Ala Thr Ala Thr Ile Asp Pro Ser Val Phe Ala
        35                  40                  45 ctt tca aat gac ttt gaa ata aca gat gtt ccg acg acg agg gag tat   192
Leu Ser Asn Asp Phe Glu Ile Thr Asp Val Pro Thr Thr Arg Glu Tyr
    50                  55                  60

```
acc ttc gat atc acc aaa gcg ttg gcc agc cct gat ggt tat gaa cga      240
Thr Phe Asp Ile Thr Lys Ala Leu Ala Ser Pro Asp Gly Tyr Glu Arg
 65                  70                  75                  80 gag gtt tac gtt gtc aac aac atg ttc cct gga cct gtg ata gag gct      288
Glu Val Tyr Val Val Asn Asn Met Phe Pro Gly Pro Val Ile Glu Ala
                 85                  90                  95 aac acc ggg gat act att atc gta cat gtc aac aat cat ttg gag gaa      336
Asn Thr Gly Asp Thr Ile Ile Val His Val Asn Asn His Leu Glu Glu
            100                 105                 110 gga caa agt atc cac tgg cat ggt ttg cgg cag ctt gca acg gct ttc      384
Gly Gln Ser Ile His Trp His Gly Leu Arg Gln Leu Gly Thr Ala Phe
        115                 120                 125 atg gac ggt gtc cct ggt ata aca cag tgt cct att ccc cct gga agc      432
Met Asp Gly Val Pro Gly Ile Thr Gln Cys Pro Ile Pro Pro Gly Ser
130                 135                 140 tca ttt acc tac caa ttc acc gta agc cat cag tca ggc acg ttt tgg      480
Ser Phe Thr Tyr Gln Phe Thr Val Ser His Gln Ser Gly Thr Phe Trp
145                 150                 155                 160 tgg cat tcc cat tat tcc aat tcc atg gcc gac ggc att tgg ggc ccc      528
Trp His Ser His Tyr Ser Asn Ser Met Ala Asp Gly Ile Trp Gly Pro
                165                 170                 175 tta att atc cat tcg ccc aat gaa ccc ctc caa agg gga cga gac tat      576
Leu Ile Ile His Ser Pro Asn Glu Pro Leu Gln Arg Gly Arg Asp Tyr
            180                 185                 190 gac gag gat cga atc gtt ttt ata act gac tgg gtg cat gac aac tca      624
Asp Glu Asp Arg Ile Val Phe Ile Thr Asp Trp Val His Asp Asn Ser
        195                 200                 205 gaa gtc gtt att gca gct cta gct act cca gaa ggg tac aaa gga agc      672
Glu Val Val Ile Ala Ala Leu Ala Thr Pro Glu Gly Tyr Lys Gly Ser
210                 215                 220 cct gct ccg cca caa ggt gat gcg att ctc atc aat gga cgt ggc caa      720
Pro Ala Pro Pro Gln Gly Asp Ala Ile Leu Ile Asn Gly Arg Gly Gln
225                 230                 235                 240 acc aac tgc aca gcc act ggt tcc tcc tca tgc acc tat ccg cct cct      768
Thr Asn Cys Thr Ala Thr Gly Ser Ser Ser Cys Thr Tyr Pro Pro Pro
                245                 250                 255 ccc gag att cac gtg cca gtc aat tgc agg gtt cgt ctg cgc ttt atc      816
Pro Glu Ile His Val Pro Val Asn Cys Arg Val Arg Leu Arg Phe Ile
            260                 265                 270 agt gcg acc gcc cat ccc atg tac cgc ata act atc gac aac cac cct      864
Ser Ala Thr Ala His Pro Met Tyr Arg Ile Thr Ile Asp Asn His Pro
        275                 280                 285 ttg gaa gtt gtg gaa acc gac ggt aca gcc gtc tat ggg ccc aca gtc      912
Leu Glu Val Val Glu Thr Asp Gly Thr Ala Val Tyr Gly Pro Thr Val
290                 295                 300 cat gaa atc tcc att gca cct ggg gaa cgg tac tct gca att atc aac      960
His Glu Ile Ser Ile Ala Pro Gly Glu Arg Tyr Ser Ala Ile Ile Asn
305                 310                 315                 320 acc tca gaa ggg aag gaa ggt gat gcg ttc tgg ctg agg aca agt gtt     1008
Thr Ser Glu Gly Lys Glu Gly Asp Ala Phe Trp Leu Arg Thr Ser Val
                325                 330                 335 gct ctg ggc tgt atg ttt ggt gga ata gat cag gtg gga ttg gcg gtt     1056
Ala Leu Gly Cys Met Phe Gly Gly Ile Asp Gln Val Gly Leu Ala Val
            340                 345                 350 gtg agg tat acg ggt aat gga atg gtt agt act gaa gag cct caa act     1104
Val Arg Tyr Thr Gly Asn Gly Met Val Ser Thr Glu Glu Pro Gln Thr
        355                 360                 365 act gct tgg agt gat cta gcg gga gct aca act cct tgt gct gga ctg     1152
Thr Ala Trp Ser Asp Leu Ala Gly Ala Thr Thr Pro Cys Ala Gly Leu
370                 375                 380
```

```
gac caa aca tat act ctt tca cca cga gag agt ttt agt gca cct cgt    1200
Asp Gln Thr Tyr Thr Leu Ser Pro Arg Glu Ser Phe Ser Ala Pro Arg
385                 390                 395                 400 gaa ttt tca caa agc cat gtc ttc aat agc cag cga gga gcc ttt gtg    1248
Glu Phe Ser Gln Ser His Val Phe Asn Ser Gln Arg Gly Ala Phe Val
                405                 410                 415 aat gtt tat ggc aac acc ttc caa ggt tat ggg ttt aac aat atc tca    1296
Asn Val Tyr Gly Asn Thr Phe Gln Gly Tyr Gly Phe Asn Asn Ile Ser
            420                 425                 430 tat cag aac caa atc ttc aac cct cta ctt tca atc gtc caa cgc ggt    1344
Tyr Gln Asn Gln Ile Phe Asn Pro Leu Leu Ser Ile Val Gln Arg Gly
        435                 440                 445 ggc tct tgc gag agc aca cta gta gcc agt aca act ttc ccc gac ctc    1392
Gly Ser Cys Glu Ser Thr Leu Val Ala Ser Thr Thr Phe Pro Asp Leu
    450                 455                 460 gga tca ggg aac att atc atc aac aat ctt gat ggc gtt atc gac cat    1440
Gly Ser Gly Asn Ile Ile Ile Asn Asn Leu Asp Gly Val Ile Asp His
465                 470                 475                 480 cct tac cac ctg cac ggc aac gag ttc cag gtg ata gga cga gga act    1488
Pro Tyr His Leu His Gly Asn Glu Phe Gln Val Ile Gly Arg Gly Thr
                485                 490                 495 gga gct ctc agc ctt gat aac ctg aca aat att gac ttc aat ttg gac    1536
Gly Ala Leu Ser Leu Asp Asn Leu Thr Asn Ile Asp Phe Asn Leu Asp
                500                 505                 510 aac cct gtg aga aag gat acc ctc tgg ata cag ggc gga agt tgg gtg    1584
Asn Pro Val Arg Lys Asp Thr Leu Trp Ile Gln Gly Gly Ser Trp Val
            515                 520                 525 gta ctg agg atc acg acg gat aac cct gga gtt tgg gcc ttg cac tgt    1632
Val Leu Arg Ile Thr Thr Asp Asn Pro Gly Val Trp Ala Leu His Cys
        530                 535                 540 cat att ggg tgg cat ctt act gag gga aag ttg gct gtg gtt gtc att    1680
His Ile Gly Trp His Leu Thr Glu Gly Lys Leu Ala Val Val Val Ile
545                 550                 555                 560 caa cca ggt gcg att gga cat atg gag ggc ccc gag tct tgg acg aat    1728
Gln Pro Gly Ala Ile Gly His Met Glu Gly Pro Glu Ser Trp Thr Asn
                565                 570                 575 ctc tgt gct aac act gat ccc aat gca ttt gga ccc gca cga cgc tca    1776
Leu Cys Ala Asn Thr Asp Pro Asn Ala Phe Gly Pro Ala Arg Arg Ser
                580                 585                 590 cct tct cca tct att caa tcc tct aag aca tcc act ttc cag tat ctg    1824
Pro Ser Pro Ser Ile Gln Ser Ser Lys Thr Ser Thr Phe Gln Tyr Leu
            595                 600                 605 cgc gaa gtg aaa ggg aag gtc gtt aaa cgt aga ggt gct cga gag gcg    1872
Arg Glu Val Lys Gly Lys Val Val Lys Arg Arg Gly Ala Arg Glu Ala
        610                 615                 620
```

<210> SEQ ID NO 19
<211> LENGTH: 624
<212> TYPE: PRT
<213> ORGANISM: Artificial
<220> FEATURE:
<223> OTHER INFORMATION: Synthetic Construct

<400> SEQUENCE: 19

```
Met Arg Gly Val Val Lys Leu Phe Phe Leu Ser Cys Ser Leu Val Ser
1               5                   10                  15

Leu Val Ser Ser Glu Glu Thr Gly Lys Ser Pro Thr Ala Asn Tyr Asp
                20                  25                  30

His Tyr Met Pro Lys Ala Thr Ala Thr Ile Asp Pro Ser Val Phe Ala
            35                  40                  45
```

```
Leu Ser Asn Asp Phe Glu Ile Thr Asp Val Pro Thr Thr Arg Glu Tyr
 50                  55                  60
Thr Phe Asp Ile Thr Lys Ala Leu Ala Ser Pro Asp Gly Tyr Glu Arg
 65                  70                  75                  80
Glu Val Tyr Val Val Asn Asn Met Phe Pro Gly Pro Val Ile Glu Ala
                 85                  90                  95
Asn Thr Gly Asp Thr Ile Ile Val His Val Asn Asn His Leu Glu Glu
            100                 105                 110
Gly Gln Ser Ile His Trp His Gly Leu Arg Gln Leu Gly Thr Ala Phe
            115                 120                 125
Met Asp Gly Val Pro Gly Ile Thr Gln Cys Pro Ile Pro Pro Gly Ser
130                 135                 140
Ser Phe Thr Tyr Gln Phe Thr Val Ser His Gln Ser Gly Thr Phe Trp
145                 150                 155                 160
Trp His Ser His Tyr Ser Asn Ser Met Ala Asp Gly Ile Trp Gly Pro
                165                 170                 175
Leu Ile Ile His Ser Pro Asn Glu Pro Leu Gln Arg Gly Arg Asp Tyr
            180                 185                 190
Asp Glu Asp Arg Ile Val Phe Ile Thr Asp Trp Val His Asp Asn Ser
            195                 200                 205
Glu Val Val Ile Ala Ala Leu Ala Thr Pro Glu Gly Tyr Lys Gly Ser
210                 215                 220
Pro Ala Pro Pro Gln Gly Asp Ala Ile Leu Ile Asn Gly Arg Gly Gln
225                 230                 235                 240
Thr Asn Cys Thr Ala Thr Gly Ser Ser Cys Thr Tyr Pro Pro Pro Pro
                245                 250                 255
Pro Glu Ile His Val Pro Val Asn Cys Arg Val Arg Leu Arg Phe Ile
            260                 265                 270
Ser Ala Thr Ala His Pro Met Tyr Arg Ile Thr Ile Asp Asn His Pro
            275                 280                 285
Leu Glu Val Val Glu Thr Asp Gly Thr Ala Val Tyr Gly Pro Thr Val
290                 295                 300
His Glu Ile Ser Ile Ala Pro Gly Glu Arg Tyr Ser Ala Ile Ile Asn
305                 310                 315                 320
Thr Ser Glu Gly Lys Glu Gly Asp Ala Phe Trp Leu Arg Thr Ser Val
                325                 330                 335
Ala Leu Gly Cys Met Phe Gly Gly Ile Asp Gln Val Gly Leu Ala Val
            340                 345                 350
Val Arg Tyr Thr Gly Asn Gly Met Val Ser Thr Glu Glu Pro Gln Thr
            355                 360                 365
Thr Ala Trp Ser Asp Leu Ala Gly Ala Thr Thr Pro Cys Ala Gly Leu
370                 375                 380
Asp Gln Thr Tyr Thr Leu Ser Pro Arg Glu Ser Phe Ser Ala Pro Arg
385                 390                 395                 400
Glu Phe Ser Gln Ser His Val Phe Asn Ser Gln Arg Gly Ala Phe Val
                405                 410                 415
Asn Val Tyr Gly Asn Thr Phe Gln Gly Tyr Gly Phe Asn Asn Ile Ser
            420                 425                 430
Tyr Gln Asn Gln Ile Phe Asn Pro Leu Leu Ser Ile Val Gln Arg Gly
            435                 440                 445
Gly Ser Cys Glu Ser Thr Leu Val Ala Ser Thr Thr Phe Pro Asp Leu
450                 455                 460
```

Gly Ser Gly Asn Ile Ile Asn Asn Leu Asp Val Ile Asp His
465                 470                 475                 480

Pro Tyr His Leu His Gly Asn Glu Phe Gln Val Ile Gly Arg Gly Thr
                485                 490                 495

Gly Ala Leu Ser Leu Asp Asn Leu Thr Asn Ile Asp Phe Asn Leu Asp
            500                 505                 510

Asn Pro Val Arg Lys Asp Thr Leu Trp Ile Gln Gly Ser Trp Val
        515                 520                 525

Val Leu Arg Ile Thr Thr Asp Asn Pro Gly Val Trp Ala Leu His Cys
530                 535                 540

His Ile Gly Trp His Leu Thr Glu Gly Lys Leu Ala Val Val Ile
545                 550                 555                 560

Gln Pro Gly Ala Ile Gly His Met Glu Gly Pro Glu Ser Trp Thr Asn
                565                 570                 575

Leu Cys Ala Asn Thr Asp Pro Asn Ala Phe Gly Pro Ala Arg Arg Ser
            580                 585                 590

Pro Ser Pro Ser Ile Gln Ser Ser Lys Thr Ser Thr Phe Gln Tyr Leu
        595                 600                 605

Arg Glu Val Lys Gly Lys Val Val Lys Arg Arg Gly Ala Arg Glu Ala
610                 615                 620

<210> SEQ ID NO 20
<211> LENGTH: 27
<212> TYPE: DNA
<213> ORGANISM: Artificial
<220> FEATURE:
<223> OTHER INFORMATION: PCR primer

<400> SEQUENCE: 20
ggatccatgc ttgtggccac cctccct                                    27

<210> SEQ ID NO 21
<211> LENGTH: 74
<212> TYPE: DNA
<213> ORGANISM: Artificial
<220> FEATURE:
<223> OTHER INFORMATION: PCR primer

<400> SEQUENCE: 21
gaattcttat cactcgaggt cttcttcgga aatcaactta gtgcaatgaa gctgtccacc    60
ttcatgggta tggc                                                    74

<210> SEQ ID NO 22
<211> LENGTH: 42
<212> TYPE: DNA
<213> ORGANISM: Artificial
<220> FEATURE:
<223> OTHER INFORMATION: PCR primer

<400> SEQUENCE: 22
ggattcatgc ttacacctga gcagctaatc actgctccac gg                    42

<210> SEQ ID NO 23
<211> LENGTH: 82
<212> TYPE: DNA
<213> ORGANISM: Artificial
<220> FEATURE:
<223> OTHER INFORMATION: PCR primer

```
<400> SEQUENCE: 23
gaattcttat cactcgaggt cttcttcgga aatcaacttc tgttccggga caacggtgtc      60
ctccaggctg acggcgttgg gg                                              82

<210> SEQ ID NO 24
<211> LENGTH: 25
<212> TYPE: DNA
<213> ORGANISM: Artificial
<220> FEATURE:
<223> OTHER INFORMATION: PCR primer

<400> SEQUENCE: 24
gtcgacatgg ccctcgacaa ggagc                                           25

<210> SEQ ID NO 25
<211> LENGTH: 93
<212> TYPE: DNA
<213> ORGANISM: Artificial
<220> FEATURE:
<223> OTHER INFORMATION: PCR primer

<400> SEQUENCE: 25
ctgcagttat cactcgaggt cttcttcgga aatcaacttc tgttccatct tggatgattc      60
ctcaaaagct gccaccatcc gcgcttcagc cgc                                  93

<210> SEQ ID NO 26
<211> LENGTH: 36
<212> TYPE: DNA
<213> ORGANISM: Artificial
<220> FEATURE:
<223> OTHER INFORMATION: PCR primer

<400> SEQUENCE: 26
ggattcatgg catcggtcca agcttacgca cagtgg                               36

<210> SEQ ID NO 27
<211> LENGTH: 97
<212> TYPE: DNA
<213> ORGANISM: Artificial
<220> FEATURE:
<223> OTHER INFORMATION: PCR primer

<400> SEQUENCE: 27
gaattcttat cactcgaggt cttcttcgga aatcaacttc tgttcacagt tgccaatggc      60
accaccatac ttgttccacg ttccaatttc gacccag                              97

<210> SEQ ID NO 28
<211> LENGTH: 38
<212> TYPE: DNA
<213> ORGANISM: Artificial
<220> FEATURE:
<223> OTHER INFORMATION: PCR primer

<400> SEQUENCE: 28
gtcgacatga agttctcttt gagcgctgct gtcctcgc                             38

<210> SEQ ID NO 29
<211> LENGTH: 92
<212> TYPE: DNA
<213> ORGANISM: Artificial
<220> FEATURE:
<223> OTHER INFORMATION: PCR primer
```

<400> SEQUENCE: 29
gaattcttat cactcgaggt cttcttcgga aatcaacttc tgttccagga tagaaccaag    60
ggcaatgcaa ggaagaccca gtccaatgag gg    92

<210> SEQ ID NO 30
<211> LENGTH: 33
<212> TYPE: DNA
<213> ORGANISM: Artificial
<220> FEATURE:
<223> OTHER INFORMATION: PCR primer

<400> SEQUENCE: 30
ggatccatgt ctcctaccat gaagaaacgt gcg    33

<210> SEQ ID NO 31
<211> LENGTH: 91
<212> TYPE: DNA
<213> ORGANISM: Artificial
<220> FEATURE:
<223> OTHER INFORMATION: PCR primer

<400> SEQUENCE: 31
gaattcttat cactcgaggt cttcttcgga aatcaacttc tgttcgcatt gccaagagct    60
atccctctct ccagggcaat caacccattc g    91

<210> SEQ ID NO 32
<211> LENGTH: 45
<212> TYPE: DNA
<213> ORGANISM: Artificial
<220> FEATURE:
<223> OTHER INFORMATION: PCR primer

<400> SEQUENCE: 32
gtcgacatgt ccctccccga tgcctaccct ccggtcatag ccacc    45

<210> SEQ ID NO 33
<211> LENGTH: 79
<212> TYPE: DNA
<213> ORGANISM: Artificial
<220> FEATURE:
<223> OTHER INFORMATION: PCR primer

<400> SEQUENCE: 33
gaattcttat cactcgaggt cttcttcgga aatcaacttc tgttcacttc tgttggccat    60
ttcagcttcc tgtctcgcc    79

<210> SEQ ID NO 34
<211> LENGTH: 36
<212> TYPE: DNA
<213> ORGANISM: Artificial
<220> FEATURE:
<223> OTHER INFORMATION: PCR primer

<400> SEQUENCE: 34
ggatccatgg aggagactgg caagtcgcca accgcg    36

<210> SEQ ID NO 35
<211> LENGTH: 96
<212> TYPE: DNA
<213> ORGANISM: Artificial
<220> FEATURE:
<223> OTHER INFORMATION: PCR primer

<400> SEQUENCE: 35
gaattcttat cactcgaggt cttcttcgga aatcaacttc tgttccgcct ctcgagcacc    60
tctacgttta acgaccttcc ctttcacttc gcgcag    96

<210> SEQ ID NO 36
<211> LENGTH: 33
<212> TYPE: DNA
<213> ORGANISM: Artificial
<220> FEATURE:
<223> OTHER INFORMATION: PCR primer

<400> SEQUENCE: 36
ggatccatgg ctgttcctcc cgagactccg cgg    33

<210> SEQ ID NO 37
<211> LENGTH: 84
<212> TYPE: DNA
<213> ORGANISM: Artificial
<220> FEATURE:
<223> OTHER INFORMATION: PCR primer

<400> SEQUENCE: 37
gaattcttat cactcgaggt cttcttcgga aatcaacttc tgttcagtga gagagcgcat    60
accattgagc aacatttcgt tggc    84

<210> SEQ ID NO 38
<211> LENGTH: 38
<212> TYPE: DNA
<213> ORGANISM: Artificial
<220> FEATURE:
<223> OTHER INFORMATION: PCR primer

<400> SEQUENCE: 38
ggatccatgc actccaaggt tgttatcatc ggctctgg    38

<210> SEQ ID NO 39
<211> LENGTH: 100
<212> TYPE: DNA
<213> ORGANISM: Artificial
<220> FEATURE:
<223> OTHER INFORMATION: PCR primer

<400> SEQUENCE: 39
gaattcttat cactcgaggt cttcttcgga aatcaacttc tgttcctcct tgtcagtgcc    60
gaagtagtgc tcggcaggga catgcacatc ttcggtctgg    100

<210> SEQ ID NO 40
<211> LENGTH: 30
<212> TYPE: DNA
<213> ORGANISM: Artificial
<220> FEATURE:
<223> OTHER INFORMATION: PCR primer

<400> SEQUENCE: 40
ggatccatgc atctcctccc gagagaaacg    30

<210> SEQ ID NO 41
<211> LENGTH: 93
<212> TYPE: DNA
<213> ORGANISM: Artificial
<220> FEATURE:
<223> OTHER INFORMATION: PCR primer

```
<400> SEQUENCE: 41
gtcgacttat cactcgaggt cttcttcgga aatcaacttc tgttcgtaaa cgaagtatct    60
cctggtcaat gggagtttgt ccgcgggtgg gac                                 93
```

COMPOSITIONS AND METHODS TO ELICIT IMMUNE RESPONSES AGAINST PATHOGENIC ORGANISMS USING YEAST-BASED VACCINES

RELATED APPLICATIONS

This application is a continuation of copending U.S. patent application Ser. No. 12/570,947, filed Sep. 30, 2009, which is a continuation of U.S. patent application Ser. No. 11/610,457, filed Dec. 13, 2006, now abandoned, which claims the benefit of priority under 35 U.S.C. §119(e) of U.S. Provisional Application No. 60/750,029, filed on Dec. 13, 2005, and of U.S. Provisional Application No. 60/817,300, filed on Jun. 28, 2006. Each of U.S. patent application Ser. Nos. 12/570,947, 11/610,457, U.S. Provisional Application No. 60/750,029 and U.S. Provisional Application No. 60/817,300 is incorporated herein by reference in its entirety.

FEDERALLY FUNDED RESEARCH

The studies disclosed herein were supported in part by grants 1 R43AI 052632-01A1, 1 R43AI054020-01A1 and 1 R41AI062482-01 from the Small Business Innovation Research Program (SBIR) and STTR Program of the National Institutes of Health. The U.S. government may have certain rights to practice the subject invention.

REFERENCE TO SEQUENCE LISTING

This application contains a Sequence Listing submitted electronically as a text file by EFS-Web. The text file, named "3923-28-1_ST25", has a size in bytes of 47 KB, and was recorded on 30 Sep. 2009. The information contained in the text file is incorporated herein by reference in its entirety pursuant to 37 CFR §1.52(e) (5).

FIELD

The present invention provides for methods, compositions and kits for reducing a fungal infection and/or inducing a protective or therapeutic response against a pathogenic or non-pathogenic organism.

BACKGROUND

Many conditions in humans and animals are caused by fungal infections and current therapeutics for the prevention of and treatments for these infections are largely ineffective. Coccidioidomycosis, also known as San Joaquin Valley Fever, is a fungal disease caused by *Coccidioides immitis* that is endemic in portions of Southern Arizona, central California, southern New Mexico and west Texas. At least 100,000 new cases are reported each year. The migration of not only permanent residents, but also agricultural workers to these areas increases exposure to *C. immitis* spores that lie dormant in the soil, and as the soil is disturbed, the spores become airborne and are inhaled. Once in the lungs, the arthroconidia transform into spherules. An acute respiratory infection occurs between seven days to three weeks after exposure and often resolves rapidly. However, in a significant number of cases, chronic pulmonary conditions or dissemination to the meninges, bones, and joints can result, leading to acute, life-threatening disease. One population, migrant laborers, is exposed to *C. immitis* and are a highly susceptible to get infected. A variety of approaches have been used to fight coccidioidomycosis, including soil treatments, but only a vaccine can completely eliminate this "emerging disease."

Another pathogen, *Cryptococcus neoformans* is an encapsulated pathogenic yeast that causes pulmonary infections and meningoencephalitis in humans and other animals. During the last 20 years, there has been a dramatic increase in the incidence of cryptococcosis throughout the world that mirrors the increase in not only HIV infections, but also in the growing number of immunocompromised patients. Loss of $CD4^+$ T cells predisposes patients to progressive infection with *C. neoformans*—this emphasizes the role of cell-mediated immunity in host resistance.

*C. neoformans* is a basidiomycetous fungus that is generally isolated as a haploid yeast, although diploids have been identified in nature. There are two mating types that can undergo recognition and fusion, and form a mycelium. A structure called a basidium is made and spores are produced from the surface of the basidium. Under specific conditions, haploid cells can undergo sporulation. Recently, a stable diploid was shown to grow as a yeast at 37° C. and formed hyphae and produced spores at 24° C. *C. neoformans* has been the subject of many studies, the var. *grubii* strain H99, as the source of the candidate immunogens. Var. *grubii* are serotype A strains, have a worldwide distribution, and are the most common variety to cause disease in the United States. Strain H99 has several advantages. First, molecular genetic analysis, including gene deletion and allelic replacement experiments, are well established in H99. Second, the genome sequence of H99 has been determined. The random shotgun and assembly phases of the genome are complete and the assembled genome has been released. Third, a congenic mating partner for H99 has recently been developed. Lastly, several reproducible animal models have been well developed to assess virulence for this strain.

Cryptococcosis is a disease that is acquired by inhalation of the organism from the soil or avian droppings into the lungs. Both immunocompetent and immunocompromised patients can be infected with the organism. In immunocompetent patients, the disease is usually contained in a lung granuloma and induces an antibody response. In contrast, individuals whose cellular immunity has been compromised by viral infection, suppression due to tissue transplantation, or anti-neoplastic chemotherapy are particularly susceptible to disseminated disease, followed by often-fatal meningoencephalitis. For example, an estimated 7-10% of AIDS patients acquire cryptococcosis during the course of their HIV disease. In compromised hosts, patients with cryptococcosis generally present with symptoms of meningitis such as fever, headache, and malaise. Cryptococcal pneumonia is the next most frequent manifestation of cryptococcosis in immunocompromised patients. It occurs as a primary infection in approximately 4% of cases and is associated with general symptoms of pneumonia such as fever, cough, pleuritic chest pain, and/or dyspnea.

*Aspergillus fumigatus* is a ubiquitous spore-bearing fungus that causes multiple diseases in humans. These include allergic asthma, aspergillomas, and invasive pulmonary disease of hosts with predisposing underlying conditions. In the United States in 1996, there were an estimated 10,190 aspergillosis-related hospitalizations; these resulted in 1,970 deaths, 176,300 hospital days, and $633 million in costs. The average hospitalization lasted 17.3 days and cost ~$62,000. Although aspergillosis-related hospitalizations account for a small percentage of hospitalizations in the United States, patients hospitalized with the condition have lengthy hospital stays and high mortality rates. The high mortality rates (in some instances over 90%) are due, in part, to the lack of rapid and sensitive diagnostic tests (all too often the diagnosis is made post mortem), as well as the lack of effective anti-fungal therapeutics.

The most common species of *Aspergillus* causing invasive disease include *A. fumigatus, A. flavus, A. niger, A. terreus* and *A. nidulans. A. fumigatus* is the most frequently found fungus in airborne spore surveys. The organism grows in a variety of environments including air ducts, houseplant soil, compost piles, and at a wide range of temperatures, from ~12° C. to 55° C. Of the genus *Aspergillus, A. fumigatus* is the most common pathogen of man.

Currently, there are a number of anti-fungal vaccine and anti-fungal treatment effort that use a variety of approaches including selected recombinantly-expressed antigens. Safe and effective vaccines against fungal organisms as well as against other similar pathogens are needed.

SUMMARY

Embodiments of the present invention concern methods and compositions for reducing the onset of, preventing or as treatment for a fungal infection. In accordance with these embodiments, a composition derived at least in part from non-viable fungal cells can be used to vaccinate a subject against or treat for a fungal infection. In certain embodiments, fungal cells were heated at a temperature of about 56° C. for about one hour. In other embodiments, fungal cells were heated at temperatures ranging from about 50° C. to about 70° C. for from about 30 minutes to about 2 hours. Time and temperature may vary depending on the fungal organism, as well as, other factors such as the type of vaccine or therapeutic desired.

Certain embodiments of the present invention concern non-viable fungal cell compositions including fungal cells that were heated at a temperature of about 56° C. for about one hour, or a derivative thereof. Other particular embodiments concern vaccines, wherein the vaccines include a composition derived from non-viable fungal cells and wherein fungal cells were heated at a temperature of about 56° C. for about one hour. In accordance with these embodiments, the fungal cells can be transgenic, non-transgenic or a combination thereof. The vaccine compositions contemplated herein are capable of inducing an immune response against viable and non-viable fungal cells when administered to a subject. Fungal cells can include, but are not limited to, *Saccharomyces* spp., *Aspergillus* spp. *Cryptococcus* spp., *Coccidioides* spp., *Neurospora* spp., *Histoplasma* spp., *Blastomyces* spp., and a combination thereof. In other embodiments, the fungal cells may further comprise a tag. In certain exemplary transgenic vaccines, compositions can include fungal cells transformed with an oligonucleotide, a peptide, a protein, a chimeric molecule or combination thereof. In addition, transgenic fungal cells can contain one or more virulence factor.

In some embodiments, a derivative of a non-viable fungal composition can be an active portion of non-viable fungal cells or a fraction thereof that is capable of inducing an immune response when introduced to a subject. In accordance with these embodiments, the derivative can be used a prophylactic against, prevention of and/or treatment for a fungal infection.

In certain embodiments of the present invention, the fungal cells comprise transgenic, non-transgenic or a combination thereof. In other embodiments, the fungal cells can include, but are not limited to, *Saccharomyces* spp., *Aspergillus* spp., *Cryptococcus* spp., *Coccidioides* spp., *Neurospora* spp., *Histoplasma* spp., *Blastomyces* spp., and a combination thereof.

In certain particular embodiments, *Saccharomyces* spp. cells can be spores, vegetative cells, germlings, or a combination thereof. In other embodiments, the *Neurospora* spp. cells can be vegetative hyphae, aerial hyphae, macroconidia, germinating macroconidia, microconidia, germinating microconidia, ascospores, germinating ascospores, or a combination thereof. In other embodiments, the *Aspergllus* spp. cells can be vegetative hyphae, conidia, or germinating conidia, or combinations thereof.

In certain embodiments, *Coccidioides* spp. cells can be arthoconidia, germinating arthroconidia, hyphae, spherules, germinating spherules, endospores, germinating endospores, or a combination thereof. In other particular embodiments, *Cryptococcus* spp. cells can be yeast cells.

In other embodiments, *Histoplasma* spp. cells can be yeast cells, vegetative hyphae, microcondia, germinating microconidia, macroconidia, germinating macroconidia, or combinations thereof.

In other embodiments, *Blastomyces* spp. cells can be yeasts, hyphae, blastoconidia, germinating blastoconidia or combinations thereof. In some embodiments of the present invention, the fungal cells may further include a tag. In other particular embodiments, transgenic fungal cells can contain at least one oligonucleotide. In certain examples, the oligonucleotide can encode a peptide or a protein. Alternatively, the transgenic fungal cells contain at least one virulence factor.

Embodiments of the present invention concern administering to a subject a vaccine that includes, at least in part, non-viable fungal cells. In certain embodiments, vaccines of the present invention induce an immune response in the subject directed against one or more fungal organisms. In accordance with these embodiments, the subject is a mammal, bird or reptile. In one particular embodiment, the subject is a human. In certain examples, the vaccine can be administered in a single dose, a few doses or multiple doses to reduce the onset of a fungal infection, preventing and/or treating a fungal infection. In other embodiments, the vaccination can occur yearly, monthly, or weekly or even more frequent depending on need.

In other embodiments, a subject having a fungal infection can be treated prophylactically to reduce progression of the fungal infection and or eliminate the infection.

In certain embodiments of the present invention, the subject is a human predisposed to a fungal infection or a fungal organism (e.g., predisposed can mean at risk of exposure or having been exposed to a fungal infection or fungal organism). In other embodiments, the subject is an immunocompromised subject. In accordance with this embodiment, the immunocompromised subject is a subject having a viral infection, tissue transplantation, anti-neoplastic chemotherapy or combination thereof.

Other embodiments of the present invention concern kits for treating and/or preventing a fungal infection. In accordance with these embodiments, the kits can include non-viable fungal cells.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 6. illustrates an exemplary schematic of a method to test a vaccine disclosed herein.

DESCRIPTION OF ILLUSTRATIVE EMBODIMENTS

Definitions

Figure 1:
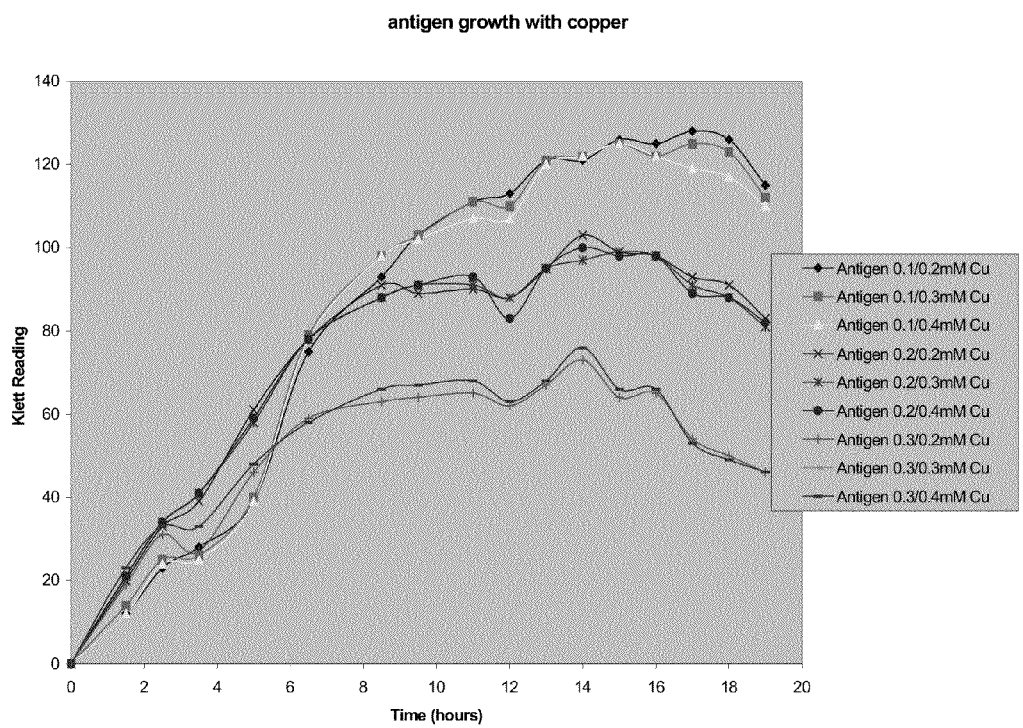
FIG. 1 represents exemplary growth curves of yeast containing a gene encoding an antigen grown in the presence of various concentrations of $CuSO_4$.

As used herein, "a" or "an" may mean one or more than one of an item.

As used herein, "about" can mean plus or minus ten percent.

DETAILED DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that sequences chosen, proteins selected, samples, concentrations, times and other specific details may be modified through routine experimentation. In some cases, well-known methods or components have not been included in the description.

Embodiments of the present invention provide for compositions and methods for reducing the onset of, preventing and/or treating a fungal infection. In particular embodiments, methods and compositions when administered to a subject are capable of inducing a protective immune response against a target. For example, these embodiments include a fungal pathogen. In accordance with these embodiments a fungal pathogenic organism includes, but is not limited to, *Aspergillus* spp., *Cryptococcus* spp., and *Coccidioides* spp. In exemplary embodiments, such pathogenic fungus may include, but are not limited to, *Aspergillus fumigatus, A. flavus, A. niger, A. terreus, A. nidulans, Coccidioides immitis, Coccidioides posadasii* and *Cryptococcus neoformans*. The immune response may be induced by injection of a fungal-based vaccine. Such vaccines may comprise, but are not limited to, suspensions, solutions, extracts, homogenates, precipitates and/or other processed or unprocessed forms of *Saccharomyces cerevisiae*. Although in exemplary embodiments the vaccines may comprise yeast transformed with genetic markers, such as a c-myc tag sequence. In one embodiment, the vaccines may include a non-transgenic fungus or fungi. In one particular embodiment, the vaccines may include non-transgenic or transgenic yeast.

Embodiments of the present invention provide for combination treatments of a subject in need of a vaccine against an organism such as a pathogenic fungal organism. In accordance with these embodiments, any vaccine treatment detailed herein may be combined with, but is not limited to, treatments for cryptococcosis, aspergillosis, or coccidoidomycosis such as amphotericin B or the azoles, fluconazole or itraconazole, 5-flucytosine, voriconazole, and fluconazole. In another embodiment, other treatments may include other antifungal treatments, such as any of the echinocandin class antifungals or any other antifungal agent.

It is contemplated herein that any of the vaccines disclosed may be administered to a subject having or suspected of developing a condition due to exposure or potential exposure to a fungal pathogen. In one embodiment, a subject may include a human. In other embodiments a subject may include a human, other mammals, birds and reptiles. In yet another embodiment, the subject can include a domesticated animal. Any of the methods disclosed herein may be used in combination with other antifungal agents or therapies to treat a subject in order to achieve the desired results.

In another embodiment, it is contemplated that a subject can be vaccinated and/or treated using a composition against a fungal pathogen disclosed herein before infection, during infection, after infection or combination thereof. In one particular embodiment, a composition disclosed herein may be used to vaccinate a subject against a particular fungal organism to reduce the risk of a fungal infection in the subject. In another embodiment, a composition disclosed herein may be used to vaccinate a subject against one or more fungal organisms to reduce the risk of a fungal infection in the subject. In certain embodiments, a vaccine containing non-viable fungal cells of one fungal type when administered to a subject may reduce the onset or progression of fungal infection of one or more additional fungal types in the subject.

In certain embodiments of the present invention, a vaccine or treatment of use in a subject can contain non-viable fungal cells where the fungal cells are transgenic, non-transgenic or a combination thereof. Transgenic cells of the present invention may include an oligonucleotide. In certain examples, the oligonucleotide can encode one or more peptides or proteins.

Advantages

Approaches disclosed herein have several advantages over current fungal vaccines. First, the fungal cells expressing each fungal protein may be engineered so that it is not secreted but rather is retained intracellularly. This likely obviates the need for large amounts of recombinant fungal antigen protein to be produced and purified, ultimately under cGMP conditions. Second, fungal cells are easily transformed and manipulated. Third, putative antigens can be tested rather inexpensively and ineffective antigens can be eliminated quickly. Fourth, whole, heat-killed yeast as a vaccine delivery vehicle is novel and presents antigens directly to dendritic cells to induce the immune system. Fifth, several individual antigen-expressing yeast strains can be mixed to form a vaccine, a possibility not readily available to current vaccine projects. Sixth, the yeast-based vaccine technology has each of the characteristics of a successful vaccine: generates a productive immune response; not neutralized; capable of generating a response to multiple epitopes; and stable and easy to manufacture.

One example of a beneficial therapeutic or a vaccine might consist of a vector with no pathogenic potential that can deliver several antigens to antigen-presenting cells (APCs). The use of recombinant yeast proves to be an ideal vector for vaccine development. In one embodiment, a vaccine contemplated herein could consist of a vector with no pathogenic potential that can deliver several antigens to APCs. In this regard, the use of recombinant yeast proves to be an ideal vector for vaccine development. The yeast *Saccharomyces cerevisiae* is avidly taken up by professional APCs, such as neutrophils, macrophages and dendritic cells. Multiple antigens can be engineered for expression within a single yeast formulation, and these formulations share many advantages with DNA vaccines, including ease of construction, low expense of mass production and biological stability. Unlike DNA vaccines, yeast-based vaccine formulations do not require extensive purification to remove potentially toxic contaminants. Furthermore, while the FDA has not evaluated yeast as a vaccine vector, the organism *S. cerevisiae* is designated by the FDA as GRAS (Generally Regarded As Safe, FDA Proposed Rule 62FR18938, Apr. 17, 1997). As described below, the heterologous proteins expressed in recombinant yeast serve as antigens that elicit CD8+ CTL-mediated immune responses in vitro and in vivo. In animal trials as a tumor vaccine, the yeast formulation was successful at protecting vaccinated animals from tumor growth (refer to FIGS. 4, 7, 11 and 12 as examples of animal model testing).

In another embodiment, it is contemplated that additional immunogens for in vivo efficacy may be tested using methods disclosed herein.

In addition, it is contemplated that the immunogens may be of a single formulation or a combination formulation. To test a formulation, immunocompetent animals or immunocompromised animals may be used in order to assess what formulation may be used to treat a subject. The test can include vaccination and then a challenge of the vaccination. In another embodiment, the appropriate dose of any disclosed therapeutic or vaccine may be determined by the methods disclosed herein including, but not limited to optimum formulation, the appropriate number of treatments or vaccinations and the optimum time for treatment or vaccinations in order to instill maximum treatment or protection against a given organism.

In certain embodiments, methods and compositions disclosed herein are directed toward making and using an anti-fungal vaccine or anti-fungal treatment. Fungal organisms targeted in the present invention include, but are not limited to, *Saccharomyces* spp., *Aspergillus* spp. *Cryptococcus* spp., *Coccidioides* spp., *Neurospora* spp., *Histoplasma* spp., *Blastomyces* spp., and a combination thereof.

*Aspergillus*

In certain embodiments of the present invention, methods, compositions and treatments for a fungal organism infection can concern treatment for or prevention of an *Aspergillus* associated-condition. The most common species of *Aspergillus* causing invasive disease include *A. fumigatus, A. flavus, A. niger, A. terreus* and *A. nidulans*. *A. fumigatus* is the most frequently found fungus in airborne spore surveys. *A. fumigatus* pneumonia and systemic aspergillosis occur primarily in patients who have immunosuppression or T-cell or phagocytic impairment. The immunodeficiency detected in these patients may be congenital, acquired or iatrogenic. Patients with chronic granulomatous diseases, neutrophil dysfunction, and with severe immunodeficiency are at risk for the development of this predominantly fatal infection. Although no important protective antibody response was detected, CD4+ Th1 cytokines appear to be important in rendering protection in these patients. In one embodiment of the present invention, a subject having or suspected of developing a disease derived from an *Aspergillus* species can be administered a composition disclosed herein. In one particular embodiment, a subject having or suspected of developing a disease derived from an *Aspergillus* species can be administered a composition including heated, transformed or non-transformed fungi for example, heated *Aspergillus* fungi.

Three main types of diseases are attributed to *A. fumigatus*; these include asthma, aspergillomas and invasive aspergillosis. The most serious disease involves invasion of hosts with predisposing underlying conditions. Patients undergoing organ transplants, bone marrow transplants, leukemics, or cancer chemotherapy are particularly at risk for invasive aspergillosis. Aspergillosis is often diagnosed when there is an unexplained pulmonary infiltrate, a patient is unresponsive to antibacterials and/or there is a fever of unknown origin. The prognosis for patients with invasive disease is high (mortality rates >50%) due to the lack of a rapid diagnostic test confirming *A. fumigatus* infection and the lack of safe and effective antifungal drugs.

*Coccidioides*

Coccidioidomycosis, also known as San Joaquin Valley Fever, is a fungal disease caused by *Coccidioides immitis* that is endemic in portions of Southern Arizona, central California, southern New Mexico and west Texas. At least 100,000 new cases are reported each year. The migration of not only permanent residents, but also agricultural workers to these areas increases exposure to *Coccidioides* spp. spores that lie dormant in the soil, and as the soil is disturbed, the spores become airborne and are inhaled. Once in the lungs, the arthroconidia transform into spherules. An acute respiratory infection occurs between seven days to three weeks after exposure and often resolves rapidly. However, in a significant number of cases, chronic pulmonary conditions or dissemination to the meninges, bones, and joints can result, leading to acute, life-threatening disease. Migrant laborers who are exposed to *Coccidioides* spp. are a highly mobile and underrepresented population, and unfortunately, this disease is under-reported and receives insufficient attention from the general medical community. A variety of approaches have been used to fight coccidioidomycosis, including soil treatments, but only a vaccine can completely eliminate this "emerging disease."

Cellular Defenses Against *Coccidioides* Spp.

Polymorphonuclear leukocytes (PMNs) are only able to partially inhibit growth of the pathogen, and are unable to kill the organism. PMNs are slightly more effective in inhibiting growth of arthroconidia than mature spherules. Since mature fungal spherules are typically 40-120 µm in diameter, a single PMN is unable to phagocytose the fungal cell. Endospores, on the other hand, are more sensitive to growth inhibition by these host cells. Most investigators of cellular immune response to *Coccidioides* spp. believe that macrophages are the pivotal effector cells in coccidioidomycosis. This concept has arisen from the general paradigm for granulomatous diseases: activated T-lymphocytes secrete cytokines, which activate macrophages, inducing the formation of a granuloma, which kills or contains the organism. As the spherule develops and matures, it becomes more resistant to macrophages, so that less than 10% of mature spherules are killed. It has been suggested that specific immunologic suppression elicited by *Coccidioides* spp. antigens prevents an effective T-cell response.

Cryptococcosis

In certain embodiments of the present invention, methods, compositions and treatments for a fungal organism infection can concern treatment for or prevention of a Cryptococcosis-associated condition. *C. neoformans* can be an intracellular as well as an extracellular pathogen. It is easily found extracellularly in cerebral spinal fluid and lung tissue. It can also be localized inside macrophages and neutrophils where it has been shown to replicate.

Antibody and cell-mediated responses can provide important protection even against an intracellular pathogen. The mammalian host has several defenses against *C. neoformans* that include components from innate, humoral, and cell-mediated immunity. Subjects are continually exposed to *C. neoformans* from the environment, a powerful innate immunity represents part of the protection afforded the normal host. This appears to be inherent in normal macrophage, monocyte, and neutrophil function.

Vaccination against cryptococcosis presents the innovative idea of not only aiming to protect an immunocompromised population, but also possibly expecting an immune response in that population. In one embodiment, a vaccine against cryptococcosis is contemplated for example, to treat a non-immunosuppressed or immunosuppressed subject. In one particular example, immunosuppressed patients such as HIV patients are contemplated. In accordance with this embodiment, an HIV patient may be vaccinated immediately after diagnosis, but before their $CD4^+$ T cell population decreases.

In other embodiments, any of the vaccines detailed herein may be directed towards other fungal organisms, for example, *Coccidioides* and *Aspergillus*. It is contemplated herein that any fungal pathogen disclosed may have one or more virulence factors which may include surface proteins, cell-wall carbohydrates, secreted factors, anchored surface molecules, modes of action to invade a host, etc. Any virulence factor associated with a fungal pathogen may be used herein as a potential target to transform yeast or other fungi of the present invention to generate a vaccine against that fungal pathogen.

In certain embodiments of the present invention, the fungal cells comprise transgenic cells, non-transgenic cells or a combination thereof. In other embodiments, the fungal cells can include, but are not limited to, *Saccharomyces* spp., *Aspergillus* spp., *Cryptococcus* spp., *Coccidioides* spp., *Neurospora* spp., *Histoplasma* spp., *Blastomyces* spp., and a combination thereof.

In certain particular embodiments, *Saccharomyces* spp. cells can be spores, vegetative cells, germlings, or a combination thereof. In other embodiments, the *Neurospora* spp. cells can be vegetative hyphae, aerial hyphae, macroconidia, germinating macroconidia, microconidia, germinating microconidia, ascospores, germinating ascospores, or a combination thereof.

Recombinant Yeast as an Antigen Delivery System

In one example, a yeast vaccine formulation directly accesses DCs, the critical immune responsive cells of the body. In order for DCs to present antigens efficiently to naive T cells, immature DCs must be activated to mature, as evidenced by the up-regulation of MHC and co-stimulatory molecules. Mature DCs are then capable of prolonged antigen presentation and the production of cytokines, such as IL-12, that are critical for the induction of cellular immune responses. Uptake of yeast by DCs increased surface expression of the co-stimulatory molecules CD40, CD80 and CD86, MHC class II, and the adhesion molecule ICAM, to levels comparable to that induced by exposure to bacterial lipopolysaccharide (LPS), a potent DC maturation factor. As further evidence of yeast-induced activation, DCs incubated with yeast produced significant amounts of IL-12 that rivalled levels induced by exposure to LPS. These results show that yeast trigger DC maturation, responses that would be essential for vaccine-induced immunity.

It has been shown that certain yeast vaccine technology can be formulated with a variety of antigens, including 5 from HIV, 3 from Hepatitis B, 1 from Hepatitis C, and 2 from lung cancer cells and, in each case, the yeast-expressed antigen effectively stimulated protective cell-mediated immunity. In addition, yeast as a vaccine vehicle provides an adjuvant effect, such that dendritic cells are triggered to directly take up yeast, causing the DCs to mature and to present the yeast-associated antigens to the host immune system. Further, recent results have shown that heat-killed yeast cells expressing putative antigens are as immunogenic and protective as live yeast cells expressing putative antigens. In addition, yeast cells expressing antigens elicited Th1 responses. Therefore, recombinant-yeast vaccine formulations may elicit systemic, antigen-specific, CD4 and CD8-based protective immunity. Also, DCs have been shown to internalize yeast and present recombinant antigens to naive class I and class II MHC-restricted T cells. It has been shown that yeast exhibit adjuvant activity for DC maturation and immune signalling. Yeast might be providing an adjuvant effect to promote immune responses to the yeast-associated antigens. These results show that i) yeast uptake triggers DC maturation; ii) yeast-expressed recombinant antigens are efficiently presented by MHC class I and MHC class II pathways of DCs, and, iii) yeast provides an adjuvant effect to enhance DC-stimulation of naive T cells.

In another example, a CD8-dependent protective immunity has been elicited in vaccinated mice. For example, EL-4 $CD4^+$ T lymphoma cells ($H-2^b$) transfected with cDNA encoding chicken ovalbumin (E.G7-OVA) and ovalbumin-expressing melanoma (B16-OVA) mouse tumor models have been employed to test vaccine candidates that induce protective CTL response. Mice vaccinated with OVAX, but not mock-vaccinated animals, were protected from E.G7-OVA or B16-OVA tumor formation. Protective immunity was CD8-dependent, since OVAX-vaccinated animals were not protected from tumor challenge in $CD8^{-/-}$ knockout mice.

Kits

In still further embodiments, the present invention concerns kits for the methods described herein. In one embodiment, a fungal organism treatment or (such as a pathogenic or non-pathogenic fungus) prevention kit is contemplated. In another embodiment, a kit for prophylactic treatment of a subject having or suspected of developing a fungal infection is contemplated. In a more particular embodiment, a kit for prevention or treatment of a subject having or suspected of developing a fungal-induced infection is contemplated. In accordance with this embodiment, the kit may be used to treat or vaccinate a subject for or against a fungal infection.

The kits may include a composition including at least a portion of a non-viable fungus within a tube, a vial or other suitable vessel. In addition, the kit may include one or more dose(s) of the composition for administration to a subject having or exposed to a fungal organism infection by a healthcare provider. In another embodiment, the kit may be a portable kit for use at a specified location outside of a healthcare facility.

The container means of any of the kits will generally include at least one vial, test tube, flask, bottle, syringe or other container means, into which the testing agent, may be preferably and/or suitably aliquoted.

Nucleic Acids

In various embodiments, isolated nucleic acids may be used to modify or transform a fungal organism contemplated in the present invention. The isolated nucleic acid may be derived from genomic DNA, RNA or complementary DNA (cDNA). In other embodiments, isolated nucleic acids, such as chemically or enzymatically synthesized DNA, may be of use for generation of oligonucleotides for transformation of a fungal organism.

A "nucleic acid" includes single-stranded and double-stranded molecules, as well as DNA, RNA, chemically modified nucleic acids and nucleic acid analogs. It is contemplated that a nucleic acid may be of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000 or greater nucleotide residues in length, up to a full length protein encoding or regulatory genetic element.

Construction of Nucleic Acids

Isolated nucleic acids may be made by any method known in the art, for example using standard recombinant methods, synthetic techniques, or combinations thereof. In some embodiments, the nucleic acids may be cloned, amplified, or otherwise constructed.

Nucleic acids of use in the present invention may include oligonucleotides that include at least a portion of sequences from a virulence factor (e.g., including but not limited to, antigen-2/proline rich antigen, hemolysin, aspf2, dpp5, dpp4, chitin deacetylase, catalase), a disease-associated factor (e.g., tumor associated antigens, cytokines, viral-associated antigens, bacterial-associated antigens) or other peptides or proteins. In another example, a multi-cloning site comprising one or more endonuclease restriction sites may be added. A nucleic acid may be attached to a vector, adapter, or linker for cloning of a nucleic acid. Additional sequences may be added to such cloning and sequences to optimize their function, to aid in isolation of the nucleic acid, or to improve the introduction of the nucleic acid into a cell. Use of cloning vectors, expression vectors, adapters, and linkers is well known in the art.

Recombinant Methods for Constructing Nucleic Acids

Isolated nucleic acids may be obtained from fungal, bacterial, viral or other sources using any number of cloning methodologies known in the art. In some embodiments, oligonucleotide probes which selectively hybridize, under stringent conditions, to the nucleic acids are used to identify a sequence of interest. Methods for construction of nucleic acid libraries are known and any such known methods may be used. (See, e.g., Current Protocols in Molecular Biology, Ausubel, et al., Eds., Greene Publishing and Wiley-Interscience, New York (1995); Sambrook, et al., Molecular Cloning: A Laboratory Manual, 2nd Ed., Cold Spring Harbor Laboratory Vols. 1-3 (1989); Methods in Enzymology, Vol. 152, Guide to Molecular Cloning Techniques, Berger and Kimmel, Eds., San Diego: Academic Press, Inc. (1987)).

Nucleic Acid Screening and Isolation

Genomic DNA, RNA or cDNA may be screened for the presence of an identified genetic element of interest using a probe based upon one or more sequences. Various degrees of stringency of hybridization may be employed in the assay. As the conditions for hybridization become more stringent, there must be a greater degree of complementarity between the probe and the target for duplex formation to occur. The degree of stringency may be controlled by temperature, ionic strength, pH and/or the presence of a partially denaturing solvent such as formamide. For example, the stringency of hybridization is conveniently varied by changing the concentration of formamide within the range of 0% to 50%. The degree of complementarity (sequence identity) required for detectable binding will vary in accordance with the stringency of the hybridization medium and/or wash medium.

High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. Other exemplary conditions are disclosed in the following Examples. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture. Nucleic acids may be completely complementary to a target sequence or may exhibit one or more mismatches.

Nucleic Acid Amplification

Nucleic acids of interest may also be amplified using a variety of known amplification techniques. For instance, polymerase chain reaction (PCR) technology may be used to amplify target sequences directly from RNA or cDNA. PCR and other in vitro amplification methods may also be useful, for example, to clone nucleic acid sequences, to make nucleic acids to use as probes for detecting the presence of a target nucleic acid in samples, for nucleic acid sequencing, or for other purposes. Examples of techniques of use for nucleic acid amplification are found in Berger, Sambrook, and Ausubel, as well as Mullis et al., U.S. Pat. No. 4,683,202 (1987); and, PCR Protocols A Guide to Methods and Applications, Innis et al., Eds., Academic Press Inc., San Diego, Calif. (1990). PCR-based screening methods have been disclosed. (See, e.g., Wilfinger et al. BioTechniques, 22(3): 481-486 (1997))

Synthetic Methods for Constructing Nucleic Acids

Isolated nucleic acids may be prepared by direct chemical synthesis by methods such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetra. Lett. 22:859-1862 (1981); the solid phase phosphoramidite triester method of Beaucage and Caruthers, Tetra. Letts. 22(20):1859-1862 (1981), using an automated synthesizer as in Needham-VanDevanter et al., Nucleic Acids Res., 12:6159-6168 (1984); or by the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. While chemical synthesis of DNA is best employed for sequences of about 100 bases or less, longer sequences may be obtained by the ligation of shorter sequences.

Covalent Modification of Nucleic Acids

A variety of cross-linking agents, alkylating agents and radical generating species may be used to bind, label, detect, and/or cleave nucleic acids. For example, Vlassov, V. V., et al., Nucleic Acids Res (1986) 14:4065-4076, disclose covalent bonding of a single-stranded DNA fragment with alkylating derivatives of nucleotides complementary to target sequences. A report of similar work by the same group is that by Knorre, D. G., et al., Biochimie (1985) 67:785-789. Iverson and Dervan also showed sequence-specific cleavage of single-stranded DNA mediated by incorporation of a modified nucleotide which was capable of activating cleavage (J Am Chem Soc (1987) 109:1241-1243). Meyer, R. B., et al., J Am Chem Soc (1989) 111:8517-8519 disclose covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., Biochemistry (1988) 27:3197-3203. Use of crosslinking in triple-helix forming probes was also disclosed by Home, et al., J Am Chem Soc (1990) 112:2435-2437. Use of N4, N4-ethanocytosine as an alkylating agent to crosslink to single-stranded oligonucleotides has also been disclosed by Webb and Matteucci, J Am Chem Soc (1986) 108:2764-2765; Nucleic Acids Res (1986) 14:7661-7674; Feteritz et al., J. Am. Chem. Soc. 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Nucleic Acid Labeling

In various embodiments, tag nucleic acids may be used to trace or identify a particular nucleic acid sequence contemplated herein. A number of different labels may be used, such as fluorophores, chromophores, radio-isotopes, enzymatic tags, antibodies, chemiluminescent, electroluminescent, affinity labels, etc. One of skill in the art will recognize that these and other label moieties not mentioned herein can be used. Examples of enzymatic tags include urease, alkaline phosphatase or peroxidase. Colorimetric indicator substrates can be employed with such enzymes to provide a detection means visible to the human eye or spectrophotometrically. A well-known example of a chemiluminescent label is the luciferin/luciferase combination.

In certain embodiments, the label may be a fluorescent, phosphorescent or chemiluminescent label. Exemplary photodetectable labels may be selected from the group consisting of Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2', 7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. These and other labels are available from commercial sources, such as Molecular Probes (Eugene, Oreg.).

In certain embodiments, it is contemplated that a vaccine will be administered to a subject for vaccination against and/or treatment of a fungal infection. It is also contemplated herein that any of the vaccines disclosed may be administered to a subject having or suspected of developing a condition due to exposure or potential exposure to a fungal pathogen. In one embodiment, a subject may include a human. In other embodiments a subject may include other mammals, birds, and reptiles. Any of the methods disclosed herein may be used in combination with other anti-fungal agents or therapies to treat a subject in order to achieve the desired results.

In another embodiment, it is contemplated that a subject can be vaccinated and/or treated using a composition against a fungal pathogen disclosed herein before infection, during infection, after infection or combination therefore of. In one particular embodiment, a composition disclosed herein may be used to vaccinate a subject against a particular fungal organism to reduce the risk of a fungal infection in the subject. In another embodiment, a composition disclosed herein may be used to vaccinate a subject against one or more fungal organism to reduce the risk of a fungal infection in the subject. In certain embodiments, a vaccine containing non-viable fungal cells of one fungal type when administered to a subject may reduce the onset or progression of fungal infection of another fungal type in the subject.

Exemplary Dosing: In one embodiment, a dose may consist of around $1 \times 10^7$ yeast cells to $20 \times 10^7$ yeast cells per dose. And may be given before infection, during infection, after infection or a combination therefore of. The dose may be given daily, every other day, biweekly, weekly, seasonally or yearly until a desired effect is achieved.

A composition of the present invention may be administered to a subject in an appropriate carrier or diluent or pharmaceutically acceptable carrier, co-administered with enzyme inhibitors or in an appropriate carrier such as liposomes. The term "pharmaceutically acceptable carrier" as used herein is intended to include diluents such as saline and aqueous buffer solutions. To administer a compound that stimulates an immune response by other than parenteral administration, it may be necessary to coat the compound with, or co-administer the compound with, a material to prevent its inactivation. Enzyme inhibitors include pancreatic trypsin inhibitor, diisopropylfluorophosphate (DEP) and trasylol. Liposomes include water-in-oil-in-water emulsions as well as conventional liposomes. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by various antibacterial and antifungal agents (i.e., parabens, chlorobutanol, phenol, ascorbic acid, thimerosal, and the like). In many cases, it will be preferable to include isotonic agents, for example, sugars, polyalcohols such as manitol, sorbitol, sodium chloride in the composition. A compound such as aluminum monostearate and gelatin can be included to prolong absorption of the injectable compositions.

Sterile injectable solutions can be prepared by incorporating active compound in the required amount in an appropriate solvent with one or a combination of ingredients enumerated above, as required, followed by filtered sterilization. Generally, dispersions are prepared by incorporating the active compound into a sterile vehicle that contains a dispersion medium and other required ingredients from those enumerated above. In the case of sterile powders for the preparation of sterile injectable solutions, the preferred methods of preparation are vacuum drying and freeze-drying which yields a powder of the active ingredient (i.e., a chemical agent, antibody, etc.) plus any additional desired ingredient from a previously sterile-filtered solution thereof.

When the active agent is suitably protected, as described above, the composition may be orally administered (or otherwise indicated), for example, with an inert diluent or an assimilable edible carrier. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of compound such as non-viable fungal cells calculated to produce the desired therapeutic effect in association with the required pharmaceutical carrier.

If needed for a particular use, the biological material can be extensively dialyzed to remove undesired small molecular weight molecules and/or lyophilized for more ready formulation into a desired vehicle, where appropriate. The active compounds will then generally be formulated for parenteral administration (i.e., formulated for injection via the intravenous, intramuscular, sub-cutaneous, intralesional, or even intraperitoneal routes). The preparation of an aqueous composition that contains an active component or ingredient will be known. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid. It must be stable under the conditions of manufacture and storage and must be preserved against the contaminating action of microorganisms, such as bacteria and fungi.

Solutions of the active compounds as free-base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure.

In addition to the compounds formulated for parenteral administration, such as intravenous or intramuscular injection, other pharmaceutically acceptable forms include, e.g., liposomal formulations; time-release capsules; and any other form currently used.

In another embodiment, nasal solutions or sprays, aerosols or inhalants may be used to deliver the compound of interest. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis. Inhalation preparations may include solutions or dry powder formulations that are commonly used along with a propellant in the formulation of therapeutics used for the treatment of asthmatics.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

Particularly preferred are methods in which the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g. antioxidants, chelating agents, inert gases and buffers).

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods

Proteins to be tested Each protein from a fungal pathogen was chosen because of its identification as a virulence factor (e.g., strains lacking the protein were less virulent that the wild type), as an immunogen (infected animals generated antibodies to the candidate protein), and/or was found on the cell surface of conidia or hyphae. In addition, none of the proteins had cognates with significant (<35%) homology to mammals and to yeast.

Exemplary isolation of DNA containing the open reading frame encoding each protein: The Open Reading Frame (ORF) of each gene was obtained by PCR using gene specific primers and in certain embodiments, a high quality cDNA library as template. In other embodiments, the ORF of candidate genes was obtained using plasmid DNA containing the gene of interest as a template for amplification by PCR. Each PCR product was gel purified and ligated into the TA cloning vector, pCR2.1, using the pCR2.1 TOPO kit from InVitrogen (Carlsbad, Calif.). Resulting plasmid DNAs were used to transform competent E. coli cells and plasmid DNA isolated from midi-preps using methods standard to those of skill in the art.

In certain embodiments the gene specific PCR primers encoded a c-myc epitope such that the c-myc epitope would be generated in the protein at the carboxy terminus.

In certain methods, each ORF was excised from each plasmid DNA using the restriction endonuclease EcoRI and ligated into the EcoRI site of pYEX-BX. Each resulting ligated plasmid was used to transform competent E. coli cells and plasmid DNA isolated from midi-preps. Each ORF DNA was sequenced to ensure that it is in frame with the copper-inducible promoter and no PCR errors were present.

In one exemplary method an empty vector control was generated. As one exemplary control, an empty vector control was generated a pYEX-BX (Clonetech) vector containing the DNA encoding a c-myc epitope but lacking a fungal gene of interest. A 51 base pair template for PCR was created that contained a methionine, the sequence that encodes the c-myc protein and two stop codons. The PCR primers also included a 5' BamH I site and a 3' EcoR I restriction site that could be used to excise the tag from the pCR 2.1 vector and inserted into the pYEX-BX vector (Clonetech). The DNA and amino acid sequences are shown in SEQ ID NOs:1 and 2:

```
atg gaa cag aag ttg att tcc gaa gaa gac ctc gag
Met Glu Gln Lys Leu Ile Ser Glu Glu Asp Leu Glu
c-myc control sequence
```

This template was amplified by PCR under the following conditions: 25 µL reactions were performed in PCR Ready Bead tubes containing 500 ng of cDNA library, 2 µM primers, and 13 µL sterile water. Reactions were performed using a Perkin Elmer 2400 Thermocycler under the following conditions: an initial cycle at 94° C. for 5 min, 30 cycles at 94° C. for 1 min, 50° C. for 1 min, 72° C. for 1 min, and a final extension at 72° C. for 7 min.

The PCR reactions were separated by agarose gel electrophoresis using a 3% (w/v) agarose gel. The 51 bp band was excised from the gel, purified and ligated into pCR 2.1 (Invitrogen). The ligated vector was used to transform competent E. coli cells and vector DNA was subsequently isolated using standard techniques. DNA isolated from several isolates was used as template for PCR reactions to confirm the presence of the c-myc insert.

Several isolates were grown, cells harvested, plasmid DNA isolated and the DNA sequence of the c-myc were determined. A comparison the sequence obtained empirically with the published sequence revealed that no PCR errors were apparent. An ATG was added by the PCR primers to ensure the translation of the c-myc peptide.

Transformation of Fungal Cells Several exemplary fungal cells that can be transformed to express vaccine proteins can include, but are not limited to, Saccharomyces spp., Aspergillus spp., Cryptococcus spp., Coccidioides spp., Neurospora spp., Histoplasma spp., Blastomyces spp., and a combination thereof.

Exemplary method of transformation of S. cerevisiae. After isolating each of the genes of interest and forming each yeast expression vector (as described), DNA vectors to individually transform yeast cells were used. The transformation protocol was as follows: 50 µL of YPD broth was inoculated with W303-1B Saccharomyces cerevisiae and the culture grown overnight at 30° C. with shaking. The desired OD600 for transformation was between 0.1-0.6 (~2×107 c/mL). Cells were harvested by centrifugation at 2000×g for 10 minutes, the pellet was washed in 25 mL sterile water and cells were again centrifuged at 2000×g for 10 minutes. The pellet was resuspended in 1 mL 0.1M lithium acetate (LiAC), centrifuged at 1000×g for 30 seconds and the supernatant removed. This pellet was again resuspended in 400 µL 0.1M LiAC and the cell suspension mixed until the cells were completely suspended. Fifty milliliters of this cell suspension was used for each transformation. The cells were centrifuged at 3000×g for 30 seconds and the supernatant discarded. To the cells was added 240 µL 50% (w/v) PEG, 36 µL 1M LiAC, 25 µL denatured carrier DNA, and 50 µL of previously diluted water containing plasmid DNA (0.1-10 µg). Cells were mixed until the pellet completely resuspended, mixtures were incubated at 30° C. for 30 minutes, and heat shocked at 42° C. for 20-25 min. The cells were harvested by centrifugation at 3000×g for 30 seconds, gently resuspended in 1 mL of water and spread onto Yeast Nitrogen Base medium (YNB) (e.g., Difco) minus uracil plates. The plates were incubated at 30° C. for 3-4 days.

Identification of yeast cells expressing candidate proteins In one example, a single yeast colony was obtained from YNB minus uracil plates and grown for overnight at 30° C. with shaking in 250 mL flasks containing 50 mL YNB minus uracil medium. Each culture was diluted to a final concentration of 0.2 (OD600) in 50 mL YNB minus uracil interim cultures. The cultures were grown at 30° C. until the OD600 had doubled (approximately 5-6 hours). The OD600 of the interim cultures was determined a final time before the cultures were diluted to a final concentration of 0.02 OD600 units in 50 mL of YNB minus uracil. These cultures were grown for 1 hour with shaking at 30° C. before 0.4 mM $CuSO_4$ (final concentration) was added. As a control, to a duplicate culture, 0.4 mM $NaSO_4$ was added to show that the protein is not produced in the absence of copper. Once the $CuSO_4$ and $NaSO_4$ were added, the cultures were grown overnight (18 hours) at 30° C. with shaking (FIG. 1).

Induced and uninduced cultures were harvested after overnight incubation by centrifugation at 550×g for 10 minutes. Each cell pellet was washed with 25 mL ice cold water to remove any residual medium and the cells were harvested again by centrifugation. Each pellet was then resuspended in 1 mL of ice cold water and divided into two 1.5 mL eppendorf tubes for centrifugation. After the removal of the supernatant, one tube was frozen at −80° C. for storage and the other was lysed for protein determination. Cells were lysed in the following manner: 100 µL of glass beads were added followed by the addition of 200 µL 2× sample lysis buffer (0.1M Tris, pH 6.8, 20% (v/v) glycerol, 4% (w/v) SDS, 0.5% (v/v) β-mercaptoethanol). Tubes were mixed by vortexing for 1 min to resuspend and lyse the cells and mixtures were boiled for 3 min to denature the proteins for SDS-PAGE gel electrophoresis. Debris was removed by centrifugation at 550×g for 5 min. and the cleared cell lysates were transferred to new tubes.

Cell lysates were loaded into the wells of 15% Tris-HCl SDS-PAGE gels (example: Bio Rad, Hercules, Calif.) in 15 µL aliquots and separated by electrophoresis at 60-80 V for 2-3 hours. Proteins were then transferred from the gel to a PVDF [poly (vinylidine fluoride)]membrane using a mini-genie transfer apparatus (Idea Scientific, Minneapolis, Minn.) for 1 hour at 12 volts.

PVDF membranes were blocked in TBST (100 mM Tris, 1.5 M NaCl and 0.1% [v/v] Tween 20) containing 5% (w/v) powdered milk (Carnation) for 1 hour at room temperature. Blocked membranes were then incubated with primary anti-c-myc epitope antibody (1:1000 dilution) in TBST containing 1% milk overnight at 4° C. The next morning the membranes were washed five times for 15 minutes each in TBST before secondary antibody was added. Secondary antibody conjugated to horse radish peroxidase (HRP) was added in TBST containing 1% (w/v) milk and incubated for 1 hour at room temperature. The membrane was washed five times for 5 minutes each in TBST before exposure to ECL reagents. The membrane was exposed to ECL (Pierce Chemical Company, Rockford, Ill.) for 1 minute then developed using an Alpha-Innotech (San Leandro, Calif.) digital system.

Figure 2:
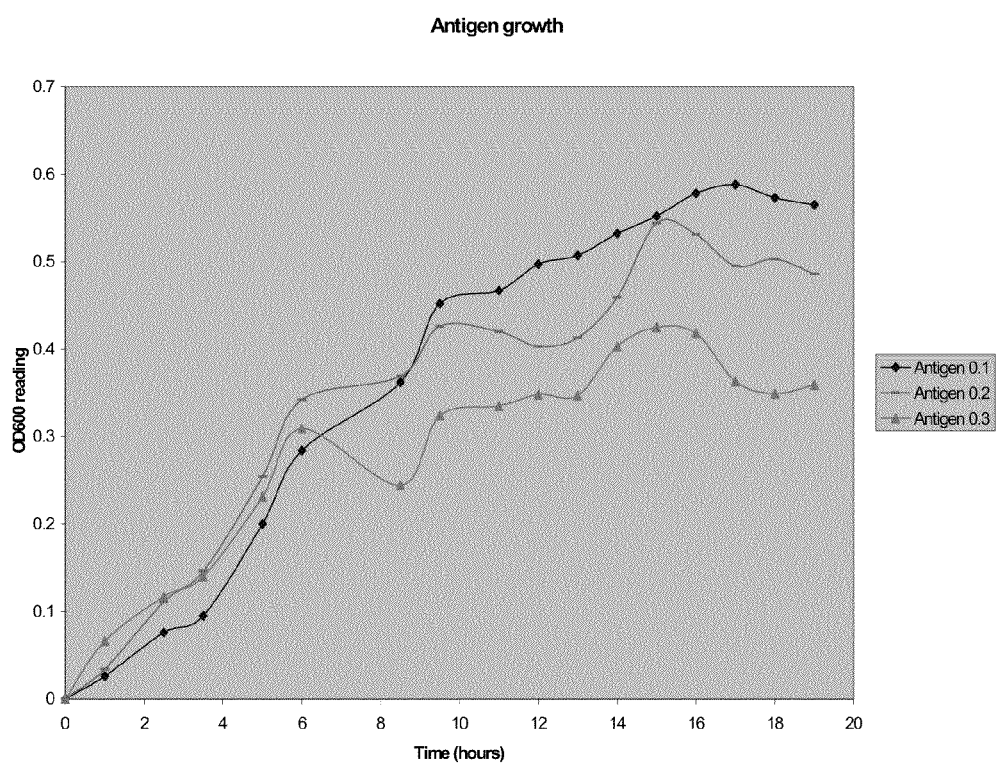
FIG. 2 illustrates an exemplary growth curve of yeast cells containing and expressing an antigen protein.

Determination of Optimal Growth Conditions of Yeast Expressing Candidate Proteins Initial 50 mL cultures were started with 800 µL of each glycerol stock that was frozen at a concentration of $1 \times 10^8$ cells/mL. Cultures were grown overnight at 30° C. with shaking. The next morning the cultures were counted using a hemocytometer as well as for the OD600 determination using a SpectraMax 340 plate reader (Molecular Devices, Sunnyvale, Calif.). Each culture was then diluted to OD600 of 0.1, 0.2, or 0.3. Duplicate cultures were grown in 250 mL Erlenmeyer flasks (50 mL cultures) as well as in 300 mL Klett flasks (containing 60 mL of medium). Samples were taken every hour from the 250 mL Erlenmeyer flasks for cell counting and OD600 readings, while Klett readings were taken using a Klett-Summerson Photoelectric colorimeter (Klett-Summerson, N.Y.). By using these methods, not only could the growth curve be characterized, but the OD600 could be correlated, cell counts, and Klett readings thereby allowing use of any of the three methods in future experiments. The following correlation was determined; 50 Klett units=0.25 OD600 units=$2 \times 10^7$ c/mL. From these data, the doubling time of the culture was determined to be approximately 5 hours. An exemplary growth curve for one such transformant is shown in FIG. 2.

Once the growth curves at each of the three initial inoculation concentrations were determined, the new variable of various $CuSO_4$ concentrations was added. Copper sulfate was tested at the following concentrations: 0, 0.2, 0.3, and 0.4 mM. The protocol to induce pYEX-BX suggested a $CuSO_4$ range of 0.2-0.5 mM and it had previously been determined that 0.5 mM was potentially toxic to the yeast. As in the experiment above, duplicate cultures were inoculated in 250 mL Erlenmeyer flasks and 300 mL Klett flasks. Samples were taken every hour from the 250 mL Erlenmyer flasks for cell counting and OD600 readings, while Klett readings were taken from the Klett flasks. The lower inoculum grew the best upon the addition of $CuSO_4$. The correlation between Klett units, OD600 units, and cell counts was the same as determined previously. The doubling time of the each culture was again 5 hours and was independent of copper concentration. The growth curve with copper for one such transformant at each innoculum is shown in FIG. 1.

Preparation of Vaccine

In one exemplary method, overnight cultures were started by adding 1 mL of a glycerol stock of yeast cells to 50 mL of YNB minus uracil medium in a 250 mL flask. Cultures were grown overnight at 30° C. with shaking. The next morning the OD600 was determined and a 50 mL interim culture was inoculated at a final OD600 of 0.2 and grown at 30° C. with shaking until it had doubled (4-5 hours). The optical density was subsequently determined for the interim culture which was used to inoculate a final 250 mL culture at 0.02 (final OD600) and grown for 1 hour at 30° C. with shaking. After the hour of growth, 0.4 mM $CuSO_4$ (final concentration) was added to induce the production of each candidate protein. This induced culture was grown for 16 to 18 hours at 30° C. with shaking. Because the doubling time for copper-induced cells was approximately 5 hours, these induced cultures were in mid to late log after about 18 hours of growth.

Heat-killed Preparations

In one example, cells from cultures were harvested by centrifugation at 1900 g for 5 min at 4° C. Cultures were washed 4 times with 100 mL room temperature PBS (137 mM NaCl, 2.7 mM KCl, 10 mM $Na_2HPO_4$, 2 mM $KH2PO_4$) to remove any residual medium and copper from the cells. Cells were resuspended in 3 mL room temperature PBS and then added to 200 mL PBS that had been pre-warmed to 56° C. The cells were subsequently heat killed by incubation at 56° C. in a water bath for 1 hour, with inversion of tubes every 10 min. to ensure that all cells were heat killed. Cells were harvested by centrifugation (1900×g for 5 min at 4° C.) and then washed 4 times with 100 mL with room temperature PBS. Cells were counted and resuspended at a final concentration of $4 \times 108$ c/mL in PBS, aliquoted in 200 mL aliquots and stored at 4° C.

Yeast cells can be heat-killed by incubation in sterile, pyrogen-free saline at 56° C. for 1 hr, washed in saline, resuspended at $2 \times 10^8$ cells/mL in sterile saline, and stored at 4° C. Each batch is expected to yield ~$2 \times 10^{10}$ yeast cells, of which a vaccine dose for the animal studies will consist of ~$1 \times 10^7$ to $20 \times 10^7$ cells.

Test for Live Cells in Heat-killed Preparations

In one method, to ensure that the heat treatment has inactivated >99.99% of the yeast cells, $1\times10^7$ heat-killed cells were incubated on agar-solidified rich medium for three days at 30° C. and the number of resulting yeast colonies (if any) determined. Only batches of cells with survival rates of <0.01% are to be used. To confirm that no live microorganisms, e.g., bacteria, were present, fluid thioglycolate medium (as described in the USP 24 NF19) may be inoculated with each batch of heat-killed yeast cells. The test mixtures were incubated for 14 days at 32° C. and examined visually for growth. Only batches of heat-killed cells in which minimal to no microbial growth was observed were used.

Endotoxin Levels of Each Batch of Vaccine

Bacterial cell-wall fragments and other pyrogens can often obscure immune responses. Pyrogen-free containers, liquids, and media were used to minimize spurious endotoxin contamination. Recently, the FDA has allowed use of a test for bacterial endotoxin levels to substitute for rabbit pyrogenicity tests. The endotoxin levels of each vaccine formulation were quantitated using a G test (Fungitec, Seikagaku Corp., Tokyo, Japan) under the U.S. Pharmacopeia (USP) guidelines. This test relies on the factor G component of horseshoe crab amoebocyte lysate. Unfortunately, this component is sensitive to $(1,3)\beta$-glucan while factors B and C are sensitive to endotoxin. Since it is expected that a small amount of fungal cell-wall glucan is present in heat-killed yeast preparations and these may lead to false positives, all samples prior to test were treated with $(1,3)\beta$-glucanase, which will destroy any $(1,3)\beta$-glucan. This procedure thus will provide an accurate determination of the endotoxin levels present. Only batches of heat-killed cells that contain <0.5 EU/mL were used.

Example 1

In certain exemplary methods, the fungal organism *Aspergillus* was examined.

Figure 3:
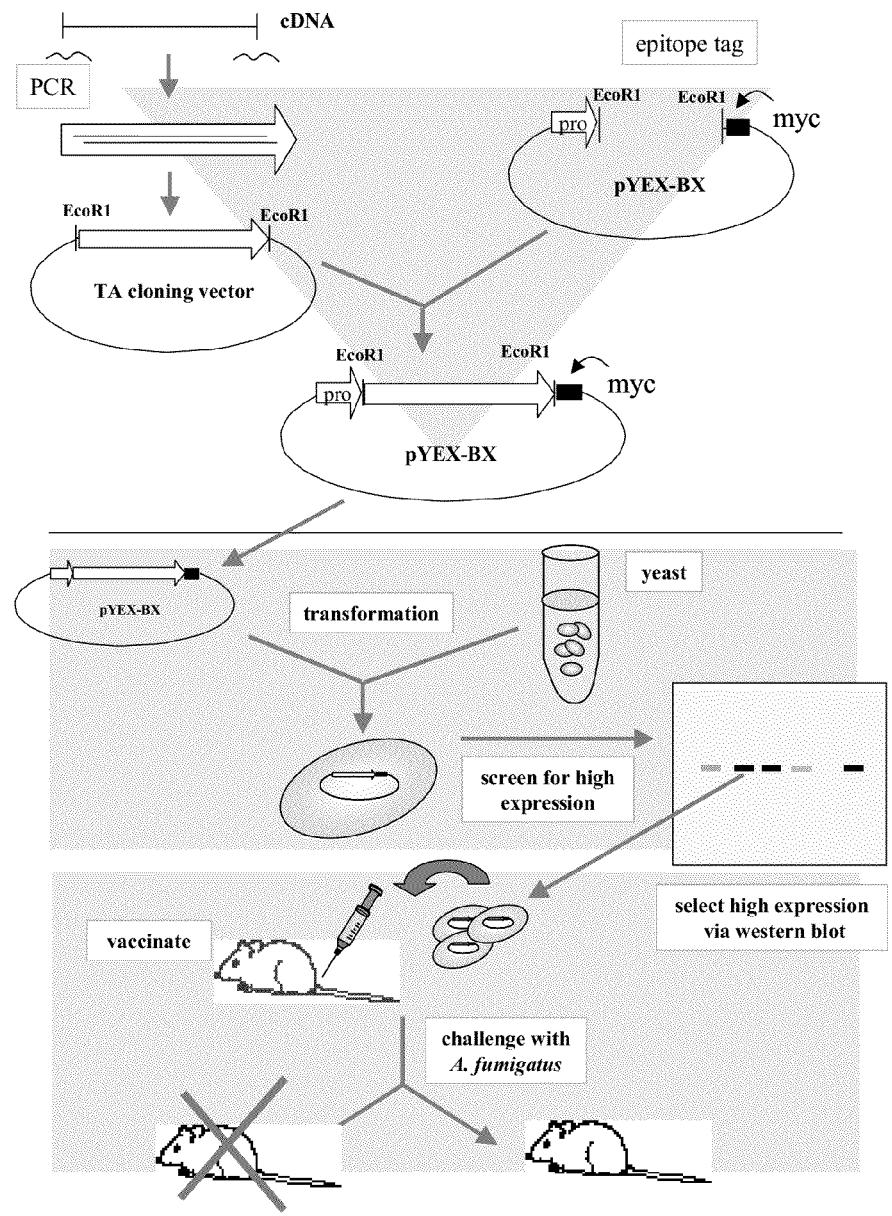
FIG. 3 illustrates an exemplary schematic of a method to test a vaccine disclosed herein.

Efficacy of Four *A. Fumigatus* antigens protecting mice from systemic aspergillosis In one exemplary method, the protective efficacy of 4 *A. fumigatus* antigens expressed in *Saccharomyces* sp. in an experimental model of systemic murine aspergillosis was tested. Efficacy was evaluated in terms of survival and tissue burden. See FIG. 3 as one exemplary strategy for vaccine generation and animal testing.

Antigens In this example, vaccines preparations containing $6\times10^7$ heat-killed yeast cells/150 microliters were administered s.c. using two injection sites (0.075 ml each) on days 28, 21 and 14 before infection. Groups pretreated with Myc (yeast containing and expressing only the c-myc tag) or PBS were used as controls.

Animals 60 CD-1 male mice weighting 30 g approx. were used.

Inoculum A total of $1.3\times10^7$ conidia of *A. fumigatus*, strain AF-10, were inoculated via lateral tail vein into the CD-1 mice.

In this exemplary method, 16 days after infection, animals were euthanatized by $CO_2$ anoxia and kidney and brain were removed. Each organ was homogenized, diluted and plated on SDA plates for CFU determination.

Survival

Figure 4:
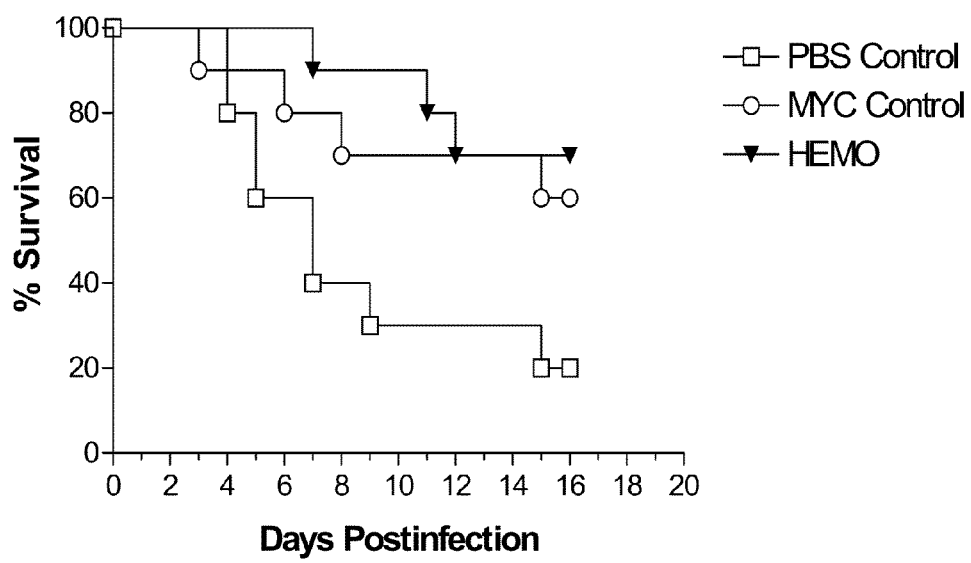
FIG. 4 illustrates exemplary survival curves for mice infected in vitro with *A. fumigatus*.

Comparisons showed that animals immunized with Hemolysin (Hemo or HEMO) antigen had an increased survival time in comparison with the PBS control group (p=0.012). In addition, the MYC control treated group did have an increased survival time in comparison with the PBS control group although this did not reach statistical significance (p=0.089) (FIG. 4).

Figure 12:
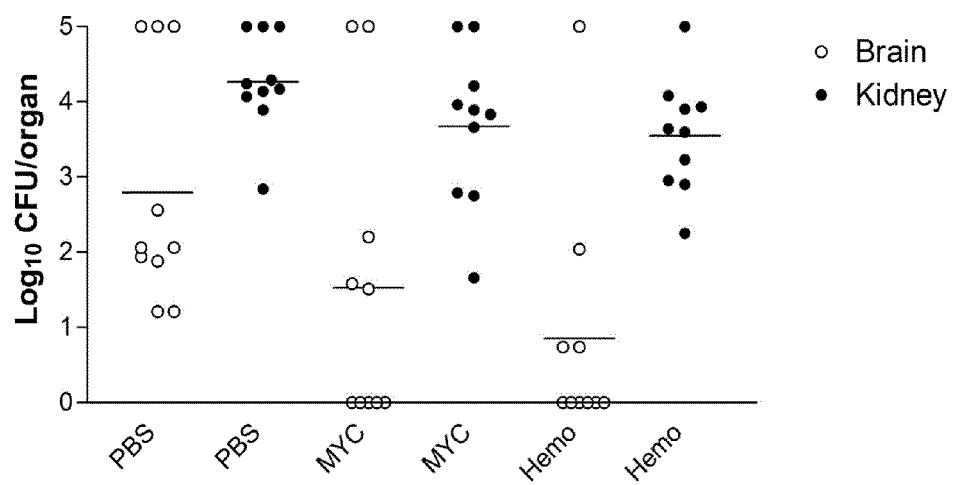
FIG. 12 illustrates an exemplary scattergram of protective efficacy of *Aspergillus* hemolysin antigen expressed in *Saccharomyces* spp. against systemic aspergillosis in mice.

In another example, the protective effect of the *A. fumigatus* antigen (HEMO) expressed in *Saccharomyces* sp. in a systemic murine model of aspergillosis was evaluated. The animal model showed low mortality in the control groups i.e., PBS and MYC, and HEMO pretreatment did not significantly prolonged the survival of the animals. However, the tissue burden study demonstrated that animals receiving three doses of the HEMO antigen before the infection had significantly lower CFU of the fungus in the kidneys and brain in comparison with the PBS-treated control animals (FIG. 12). These results demonstrate that HEMO pretreatment provides protective resistance against systemic aspergillosis.

Exemplary Cloning of AspF 2. Published DNA and predicted amino acid sequences to design PCR primers to amplify the ORF from the *Aspergillus fumigatus* cDNA library were used. The DNA and amino acid sequences of AspF 2 are presented in diagram form in SEQ ID NOs:3 and 4. The positions of the 5' and 3' primers use to obtain the predicted PCR product are also shown in SEQ ID NOs:3 and 4.

```
atg ctt gtg gcc acc ctc cct acc tcc ccc gtc ccc atc gcg gcg cga        48
Met Leu Val Ala Thr Leu Pro Thr Ser Pro Val Pro Ile Ala Ala Arg
1               5                   10                  15 gca acc ccc cac gaa ccc gtc ttc ttc tcc tgg gac gct ggc gcg gtg        96
Ala Thr Pro His Glu Pro Val Phe Phe Ser Trp Asp Ala Gly Ala Val
                20                  25                  30 acc tcg ttc ccc atc cac tcc agc tgc aat gcg acc cag cgc cgg cag        144
Thr Ser Phe Pro Ile His Ser Ser Cys Asn Ala Thr Gln Arg Arg Gln
            35                  40                  45 atc gag gcc ggc ctg aac gag gcg gtc gag ctc gcc cgg cac gcc aag        192
Ile Glu Ala Gly Leu Asn Glu Ala Val Glu Leu Ala Arg His Ala Lys
        50                  55                  60 gcc cac atc ctc cgc tgg ggc aac gag agc gag atc tac cgg aag tac        240
Ala His Ile Leu Arg Trp Gly Asn Glu Ser Glu Ile Tyr Arg Lys Tyr
65                  70                  75                  80 ttt ggc aac cgg ccc acc atg gag gcc gtc ggt gcc tac gat gtc atc        288
Phe Gly Asn Arg Pro Thr Met Glu Ala Val Gly Ala Tyr Asp Val Ile
                85                  90                  95
```

```
                                              -continued
gtg aac ggg gac aag gcc aac gtg ctc ttc cgg tgt gac aac ccc gac      336
Val Asn Gly Asp Lys Ala Asn Val Leu Phe Arg Cys Asp Asn Pro Asp
                100                 105                 110 ggc aac tgt gct ttg gaa ggc tgg ggc ggc cac tgg cgc ggc gcg aac      384
Gly Asn Cys Ala Leu Glu Gly Trp Gly Gly His Trp Arg Gly Ala Asn
            115                 120                 125 gcc acc tcc gaa acc gtc atc tgt gat cgc agc tac acc acc cgc cgc      432
Ala Thr Ser Glu Thr Val Ile Cys Asp Arg Ser Tyr Thr Thr Arg Arg
        130                 135                 140 tgg ctt gtc tcc atg tgc tcc cag ggc tac acc gtc gcc ggc tcc gag      480
Trp Leu Val Ser Met Cys Ser Gln Gly Tyr Thr Val Ala Gly Ser Glu
145                 150                 155                 160 acc aac acc ttc tgg gct tcg gac ctg atg cac cgt ctg tac cat gtg      528
Thr Asn Thr Phe Trp Ala Ser Asp Leu Met His Arg Leu Tyr His Val
                165                 170                 175 cct gct gtg ggt caa ggc cgg gtc gac cac ttc gcc gac ggc tac gac      576
Pro Ala Val Gly Gln Gly Arg Val Asp His Phe Ala Asp Gly Tyr Asp
            180                 185                 190 gag gtg att gcc ctg gcc aag agc aac ggc acc gag tcc acg cat gac      624
Glu Val Ile Ala Leu Ala Lys Ser Asn Gly Thr Glu Ser Thr His Asp
        195                 200                 205 tcg gag gcg ttg cag tat ttc gcc ctt gag gcg tat gcg ttt gat att      672
Ser Glu Ala Leu Gln Tyr Phe Ala Leu Glu Ala Tyr Ala Phe Asp Ile
    210                 215                 220 gcc gct ccc ggt gtc gga tgt gct ggc gag agt cac ggc cct gac cag      720
Ala Ala Pro Gly Val Gly Cys Ala Gly Glu Ser His Gly Pro Asp Gln
225                 230                 235                 240 gga cat gac acc ggg tct gcc tcg gcg cct gcg tct acc tcc acc tct      768
Gly His Asp Thr Gly Ser Ala Ser Ala Pro Ala Ser Thr Ser Thr Ser
                245                 250                 255 agc tcc agc tcg ggc tcg ggc tcg ggc gcc acg act acc ccg acg gat      816
Ser Ser Ser Ser Gly Ser Gly Ser Gly Ala Thr Thr Thr Pro Thr Asp
            260                 265                 270 tct ccc agt gcc act att gat gtg ccg tcg aac tgc cat acc cat gaa      864
Ser Pro Ser Ala Thr Ile Asp Val Pro Ser Asn Cys His Thr His Glu
        275                 280                 285 ggt gga cag ctt cat tgc act                                          885
Gly Gly Gln Leu His Cys Thr
    290                 295
```

A 16 amino acid signal sequence was predicted by PSORTII (psort.nibb.ac.jp/cgi-bin). The signal sequence was subsequently removed as PSORTII predicted that the protein would be extracellular, which suggested that the protein would be secreted by the *S. cerevisiae* if the signal sequence was left intact. A methionine was added before the 17th amino acid to ensure that the protein would be translated.

The following conditions were used to amplify AspF 2 from an *Aspergillus fumigatus* cDNA library: 25 μL reactions were performed in PCR Ready Bead tubes (Amersham Pharmacia) containing 500 ng of cDNA library, 2 μM primers, and 13 μL sterile water. Reactions were performed using the Perkin Elmer 2400 Thermocycler (PE Applied Biosystems) under the following conditions: an initial cycle at 94° C. for 5 min, 30 cycles at 94° C. for 1 min, 50° C. for 1 min and 72° C. for 1 min, and a final extension at 72° C. for 7 min.

The PCR reactions were separated using agarose gel electrophoresis and a photograph of a representative gel data not shown. A band of approximately 936 bases corresponding to the amplified AspF 2 ORF contains a 3' c-myc tag.

The band was excised from the gel, purified and ligated into pCR 2.1. The ligated vector was used to transform competent *E. coli* cells and vector DNA isolated from 5 mL mini cultures using standard alkaline lysis techniques. DNA isolated from several miniprep isolates was digested with EcoRI and separated by agarose gel electrophoresis to confirm the presence of the 936 base AspF 2/c-myc insert.

Several isolates were grown, cells harvested, plasmid DNA isolated and the DNA sequence of the AspF 2 insert determined. A comparison of the sequence obtained empirically with the published sequence was determined (SEQ ID NOs: 5 and 6). There were no apparent PCR errors.

```
                                                        SEQ ID NO: 5
- AspF2
accaacacct tctgggcttc ggacctgatg caccgtctgt accatgtgcc tgctgtgggt      60
caaggccggg tcgaccactt cgccgacggc tacgacgagg tgattgccct ggccaagagc     120
```

```
                                     -continued
aacggcaccg agtccacgca tgactcgag gcgttgcagt atttcgccct tgaggcgtat        180
gcgtttgata ttgccgctcc cggtgtcgga tgtgctggcg agagtcacgg ccctgaccag        240
ggacatgaca ccgggtctgc ctcggcgcct gcgtctacct ccacctctag ctccagctcg        300
ggctcgggct cgggcgccac gactaccccg acggattctc ccagtgccac tattgatgtg        360
ccgtcgaact gccataccca tgaaggtgga cagcttcatt gcactgaaca gaagttgatt        420
tccgaagaag acctcgag                                                     438

SEQ ID NO: 6
- AspF2 PCR
accaacacct tctgggcttc ggacctgatg caccgtctgt accatgtgcc tgctgtgggt         60
caaggccggg tcgaccactt cgccgacggc tacgacgagg tgattgccct ggccaagagc        120
aacggcaccg agtccacgca tgactcggag gcgttgcagt atttcgccct tgaggcgtat        180
gcgtttgata ttgccgctcc cggtgtcgga tgtgctggcg agagtcacgg ccctgaccag        240
ggacatgaca ccgggtctgc ctcggcgcct gcgtctacct ccacctctag ctccagctcg        300
ggctcgggct cgggcgccac gactaccccg acggattctc ccagtgccac tattgatgtg        360
ccgtcgaact gccataccca tgaaggtgga cagcttcatt gcactgaaca gaagttgatt        420
tccgaagaag acctcgag                                                     438
```

The DNA of an isolate was excised from the pCR 2.1 vector (Invitrogen) with a BamHI/EcoRI double digest and the reactions were separated by electrophoresis so that the DNA band encoding the AspF 2 ORF could be isolated. This DNA fragment was then ligated into the pYEX-BX vector using the same restriction enzymes. The ligated vector was then used to transform competent E. coli and the plasmid DNA isolated by standard alkaline lysis mini-preps. The DNA sequence of salient portions of the vector was determined to ensure the correct alignment of the ORF with the TATA box. Then portions of the vector were sequenced data not shown. The TATA box, the aspf-2 coding sequence, the c-myc tag sequence, and the stop codons were identified (SEQ ID NOs:1 and 2).

Exemplary cloning method for Hemolysin Published DNA and predicted amino acid sequences of Hemolysin to design PCR primers to amply the ORF from the A. fumigatus cDNA library were used. The DNA and amino acid sequences are presented in diagram form in SEQ ID NOs:7 and 8, along with the positions of the 5' and 3' primers used to obtain the predicted PCR product are shown. No signal sequence was predicted by PSORTII (psort.nibb.ac.jp/cgi-bin).

The following conditions were used to amplify hemolysin from the cDNA library: 25 µL reactions were performed in PCR Ready Bead tubes containing 500 ng of cDNA library, 2 µM primers, and 13 µL sterile water. Reactions were performed using a Perkin Elmer 2400 Thermocycler under the following conditions: an initial cycle at 94° C. for 5 min, 30 cycles at 94° C. for 1 min, 50° C. for 1 min, 72° C. for 1 min, and a final extension at 72° C. for 7 min.

Figure 5:
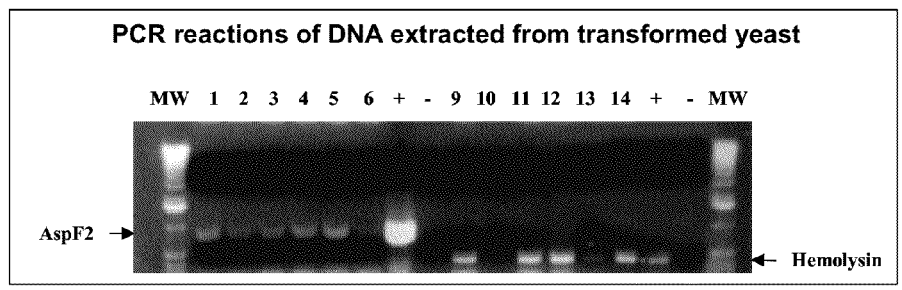
FIG. 5. represents an exemplary electrophoresis gel of separated nucleic acid sequences from PCR reactions.

The PCR reactions were separated using agarose gel electrophoresis and a band of approximately 444 bp corresponding to the amplified hemolysin ORF was excised from the gel, purified and ligated into pCR 2.1. The ligated vector was used to transform competent E. coli cells and vector DNA was subsequently isolated using standard techniques. DNA isolated from several isolates was used as template for PCR reactions to confirm the presence of the hemolysin insert. Not all isolates contained the hemolysin insert due to self ligation of the pCR 2.1 vector. See FIG. 5.

Several isolates were grown, cells harvested, plasmid DNA isolated and the DNA sequence of the hemolysin were determined. A comparison the sequence obtained empirically with

```
nucleic acid and corresponding amino acid sequence of Hemolysin
                                                       SEQ ID NOs: 7 and 8
                  ─────────────────────────────────▶
ATGGCATCGGTCCAAGCTTACGCACAGTGGGTTACGGTTCATCTCATCAATAGCATGTCTTCCGAGACCTTGAGTATCAA M   A   S   V   Q   A   Y   A   Q   W   V   T   V   H   L   I   N   S   M   S   S   E   T   L   S   I   K AATGCTAGTCTCTCCTGGGGCAAGTGGTACAAGGACGGTGACAAGGACGCCGAAATCACAAGTGAAGATGTCCAGCAAAAG N   A   S   L   S   W   G   K   W   Y   K   D   G   D   K   D   A   E   I   T   S   E   D   V   Q   Q   K ACGGCACCCCCAGGCGGTTCCGTGAACGTCAACTCTTGCGGTCGCAGCGACGCTTCGAGTGGAACGACGGGAGGTTTTGAT T   A   P   P   G   G   S   V   N   V   N   S   C   G   R   S   D   A   S   S   G   T   T   G   G   F   D TTGTATGACGGCAATACCAAGATTGGAAGAGTCCACTGGGACTGTCCATGGGGTTCTAAAACCAACGATTTCGATGTTGGA L   Y   D   G   N   T   K   I   G   R   V   H   W   D   C   P   W   G   S   K   T   N   D   F   D   V   G GAGAGAAACAAAAATTACTGGGTCGAAATTGGAACGTGGAACAAGTATGGTGGTGCCATTGGCAACTGT
                              ◀─────────────────────────────────
 E   R   N   K   N   Y   W   V   E   I   G   T   W   N   K   Y   G   G   A   I   G   N   C
``` the published sequence revealed that no PCR errors were apparent, the sequence as shown in SEQ ID NOs:9 and 10.

```
Hemo
                                                       SEQ ID NO: 9
ATGGCATCGGTCCAAGCTTACGCACAGTGGGTTACGGTTCATCTCATCAATAGCATGTCTTCCGAGAC

CTTGAGTATCAAGAATGCTAGTCTCTCCTGGGGCAAGTGGTACAAGGACGGTGACAAGGACGCCGAA

ATCACAAGTGAAGATGTCCAGCAAAAGACGGCACCCCCAGGCGGTTCCGTGAACGTCAACTCTTGCG

GTCGCAGCGACGCTTCGAGTGGAACGACGGGAGGTTTTGATTTGTATGACGGCAATACCAAGATTGGA

AGAGTCCACTGGGACTGTCCATGGGGTTCTAAAACCAACGATTTCGATGTTGGAGAGAGAAACAAAA

ATTACTGGGTCGAAATTGGAACGTGGAACAAGTATGGTGGTGCCATTGGCAACTGTGAACAGAAGTTG

ATTTCCGAAGAAGACCTCGAG

Hemo PCR
                                                       SEQ ID NO: 10
ATGGCATCGGTCCAAGCTTACGCACAGTGGGTTACGGTTCATCTCATCAATAGCATGTCTTCCGAGAC

CTTGAGTATCAAGAATGCTAGTCTCTCCTGGGGCAAGTGGTACAAGGACGGTGACAAGGACGCCGAA

ATCACAAGTGAAGATGTCCAGCAAAAGACGGCACCCCCAGGCGGTTCCGTGAACGTCAACTCTTGCG

GTCGCAGCGACGCTTCGAGTGGAACGACGGGAGGTTTTGATTTGTATGACGGCAATACCAAGATTGGA

AGAGTCCACTGGGACTGTCCATGGGGTTCTAAAACCAACGATTTCGATGTTGGAGAGAGAAACAAAA

ATTACTGGGTCGAAATTGGAACGTGGAACAAGTATGGTGGTGCCATTGGCAACTGTGAACAGAAGTTG

ATTTCCGAAGAAGACCTCGAG
```

The DNA of one isolate was treated with BamH I/EcoRI and the DNA band encoding the hemolysin ORF/c-myc tag was isolated. This DNA fragment was then ligated into vector pYEX-BX that had also been digested with BamH I/EcoRI. The ligated vector was then used to transform competent E. coli and the plasmid DNA was subsequently isolated. The DNA sequence of the relevant portions of the vector was determined to ensure the correct alignment of the ORF with the TATA box and the c-myc tag was in frame with the rest of the ORF. The sequenced portion of the vector is presented in SEQ ID NO:11. In addition, this vector was used for Examples 2 and 3.

ID NOs:1 and 2) The DNA of one isolate was treated with BamH I/EcoRI and the DNA band encoding the c-myc tag was isolated. This DNA fragment was then ligated into pYEX-BX which had also been digested with BamHI and EcoRI. The ligated vector was used to transform competent E. coli cells and vector DNA isolated using standard techniques. DNA isolated from several miniprep isolates was used as template for PCR reactions to confirm the presence of the c-myc control insert. (SEQ ID NOs:1 and 2)

Several isolates were grown, cells harvested, plasmid DNA isolated and the DNA sequence of the c-myc control insert were determined. The DNA sequence of pertinent portions of the vector was determined to ensure the correct alignment of the c-myc control with the TATA box.

```
Portions of pYEX-BX that were sequenced
                                                       SEQ ID NO: 11
ATCMGSTTMGCAAAAGTMTACMACGCAATATGGATTGTCAGAATMTATAAAAGAGAAGCAA

ATAACTCCTTGTCTTGTATCAATTGCATTATAATATCTTCTTGTTAGTGCAATATCATATAGAAG

TCATCGAAATAGATATTAAGAAAAACAAACTGTACAATCAATCATCACATCAATCATCACATA

AAATATTCAGCGAATTGGATCCATGGAACAGAAGTTGATTTCCGAAGAAGACCTCGAGTGATAAG

AATTCATTAACTTCCAAAATGAAGGTCATGAGTGCCAATGCCAATGTGGTAGCTGCAAAAATA

ATGAACAATGCCAAAAATCATGTAGCTGCCCAACGGGGTGTAACAGCGACGACAAATGCCCCT

GCGGTAACAAGTCTGAAGAAACCAAGAAGTCATGCTGCTCTGGGAAATGAAACGAATAGTCTT

TAATATATTCATCTAACTATTTGCTGTTTTTAATTTTTAAAAGGAGAAGGAAGTTTAATCGACG

ATTCTACTCAGTTTGA
```

In one exemplary method an empty vector control was generated as previously described in Methods (. This template was amplified by PCR as discussed previously. DNA isolated from several isolates was used as template for PCR reactions to confirm the presence of the c-myc insert. (SEQ In one exemplary method, transformants expressing each A. fumigatus protein were identified and the cleared cell lysates were generated and stored as previously discussed.

After gel separation, expression of A. fumigatus proteins was determined by western blot by methods known in the art.

In one exemplary method growth of transformants were determined. Transformants that were determined to produce a protein of the correct molecular weight above were grown in YNB minus uracil for 2-3 days at 30° C. with shaking. Once the cultures were in stationary phase, the cells were counted and frozen in 50% glycerol at a final concentration of 1×108 c/mL (10 yeast units) and stored at −80° C. until use.

The production of vaccines for animal models was used as previously disclosed. Each of four *A. fumigatus* genes from a cDNA library using gene-specific PCR primers were cloned. The DNA encoding each ORF was sequenced to confirm that the correct gene had been cloned followed by an inframe c-myc tag and that no PCR errors were introduced. The ORF of each gene was inserted into the copper inducible vector pYEX-BX. Portions of each ligated vector were sequenced to ensure the correct position of the gene relative to the TATA box.

Each pYEX-BX vector containing a gene of interest was used to transform yeast and yeast transformants expressing each of the four proteins identified by Western blot analysis. Each *S. cerevisiae* strain that produced the correct protein was subsequently produced and used to vaccinate an animal as discussed above.

*Aspergillus*. In another exemplary method, the protective efficacy of HEMO antigen expressed in *Saccharomyces* spp. against systemic aspergillosis was tested in mice.

Antigen. HEMO antigen was administered s.c. using two injection sites dorsally (0.075 ml each) on days 28, 21 and 14 before infection, receiving $6 \times 10^7$ yeast cells per animal. Control animals received PBS (diluent control) or MYC (yeast not expressing immunogen control) at $6 \times 10^7$ yeast cells per animal.

Animals. Thirty six weeks-old male CD-1 mice were used. Animals were housed in standard conditions in cages of 5 animals. Groups of 10 mice per group were established.

Infection. A total of 5.8×106 viable *Aspergillus fumigatus* conidia per mouse were inoculated intravenously via lateral tail vein.

Tissue burden. 16 days after infection surviving animals were euthanatized by CO2 anoxia. The kidney and brain were removed aseptically, homogenized in 0.9% saline, diluted and plated on SDA plates for CFU determination.

Statistics. Comparisons of survival were done by a log rank test and tissue burden by Mann Whitney test using GraphPad 3.03 for Windows.

FIG. 12 represents an exemplary Log 10 CFU per studied organ. Pretreatment with HEMO antigen significantly reduced tissue burdens from brain and kidney in comparison to the diluent control (p=0.003 and 0.023, respectively). In addition the yeast control (MYC) reduced organs burdens as well but did not reach statistical significance (p=0.089 in both organs). No differences were found between MYC and PBS groups. Importantly, 50 and 60% of the animals receiving MYC or HEMO, respectively, did not show detectable amount of *A. fumigatus* in brain but all PBS-pretreated animals showed fungal grown in this organ.

The protective effect of the *A. fumigatus* antigen (HEMO) expressed in *Saccharomyces* was tested in a systemic murine model of aspergillosis. The MYC only yeast control group did show a reduction in the brain organ burden. Importantly, the tissue burden study demonstrated that animals receiving three doses of the HEMO antigen before the infection had statistically significantly lower CFU of the fungus in the kidneys and brain in comparison with the PBS-treated control animals. These results show that the vaccine containing either yeast alone (MYC) or Hemo protected mice against an infection of *Aspergillus fumigatus*.

Example 2

In certain exemplary methods, the fungal organism *Coccidioides* was examined.

Figure 6:
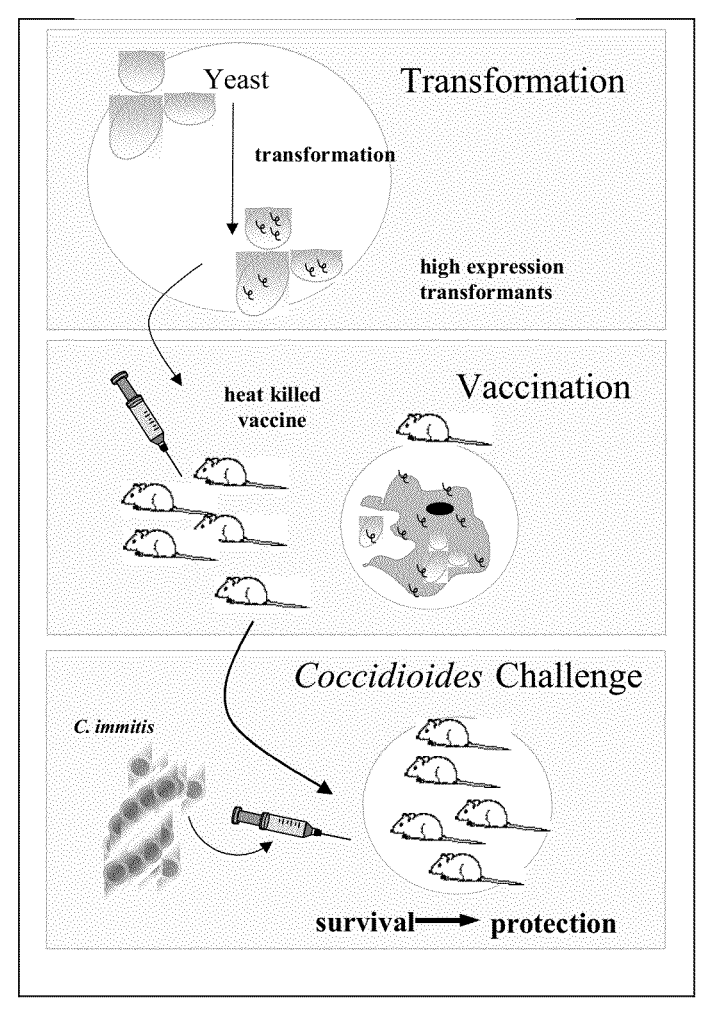

See one exemplary schematic for production of and testing for an anti-fungal vaccination in a *Coccidioides* animal model (FIG. 6). In one exemplary method, the feasibility of using heat-killed yeast cells expressing a *C. immitis* antigen as a vaccine against *C. immitis* infections was examined. cDNA was obtained for each the *C. immitis* gene whose protein has been shown in other work to elicit an immune response in infected animals. Then yeast were transformed with each cDNA and strains selected that expressed a high levels of the antigen. A schematic of the strategy is depicted in FIG. 6.

In another exemplary method, the protective effect of *Coccidioides immitis* antigen expressed by *Saccharomyces cerevisiae* was analyzed and used as a killed whole vaccine preparation in a systemic murine model of coccidioidomycosis. DNA encoding for Ag2 (also called PRA) was cloned into *S. cerevisiae* and gene expression induced using for example, copper. These yeast cells were heat killed and used to vaccinate mice prior to infection with *Coccidioides immitis*.

Animals. Six-week-old male CD-1 mice were purchased from Charles River Laboratories. Groups consisted on 20 mice, housed in standard conditions. After infection, mice were housed in micro-isolator cages. Animals were provided food and acidified water ad libitum.

Antigen. In this exemplary example, a *C. immitis* antigen expressed in *Saccharomyces* was used. This was a protein present in the alkali-soluble and water-soluble preparation of the spherule wall and called antigen 2 (Ag2/PRA). The vaccine was administered subcutaneously (s.c.) in a volume of 50 µl three times before infection (i.e., 21, 14 and 7 days prior to the infection) at a concentration of $4 \times 10^8$ cells/ml. In this example, PBS was used as the control.

Inoculum. *Coccidioides immitis* (Silveira strain) was used. The strain was grown on glucose yeast-extract (GYE) plates in a Class 3 biosafety cabinet at room temperature for 2 weeks. Arthroconidia were harvested as a suspension in saline. The number of arthroconidia was determined by hemacytometer and verified for viability by cfu (colony forming units) determination done by plating inoculum dilutions on GYE medium. Animals were infected intravenously (i.v.) with a suspension containing 376 viable arthroconidia per mouse. Statistical analysis of survival was done using a log rank test.

Figure 7:
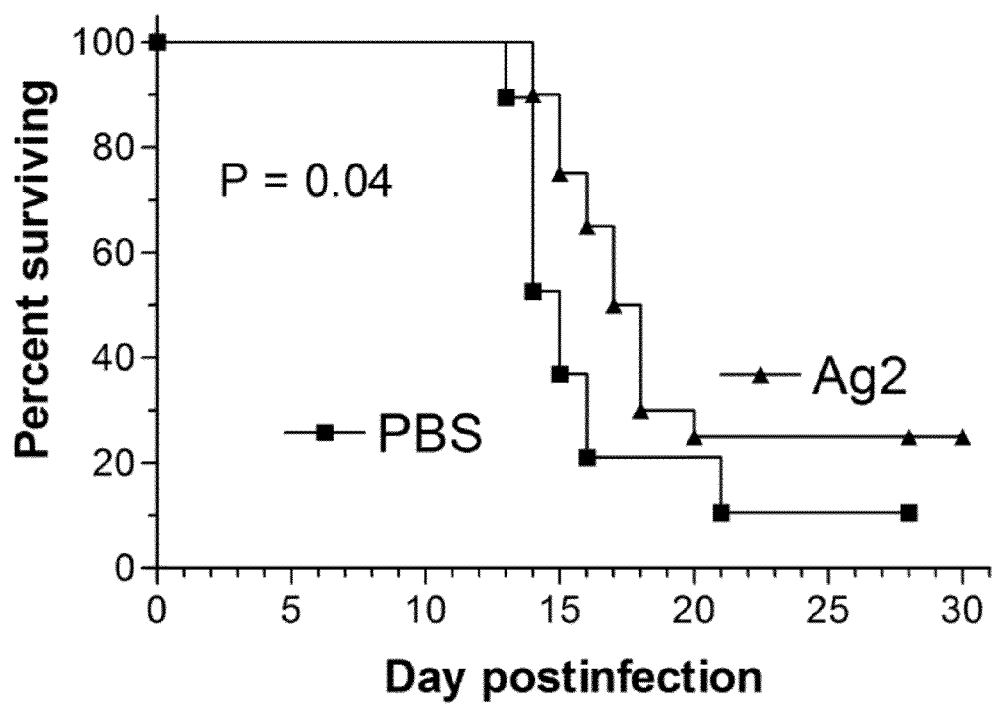
FIG. 7 illustrates exemplary survival curves for mice infected in vitro with *C immitis*.

FIG. 7 illustrates an exemplary the survival curve of the groups of mice included in the study that was vaccinated with yeast expressing the antigen-2/PRA protein. Deaths of control animals and pretreated animals began on day 13 after infection and by day 21 only 10% of the PBS treated mice were still alive. This was in contrast to the mice treated with the Ag-2 containing yeast (25% still alive) Statistical comparisons between groups showed a significant difference between the control group and Ag2 immunized animals (p=0.04). This example shows that mice vaccinated with yeast cells expressing the antigen-2/PRA protein survived to a greater extent than untreated mice.

Figure 8:
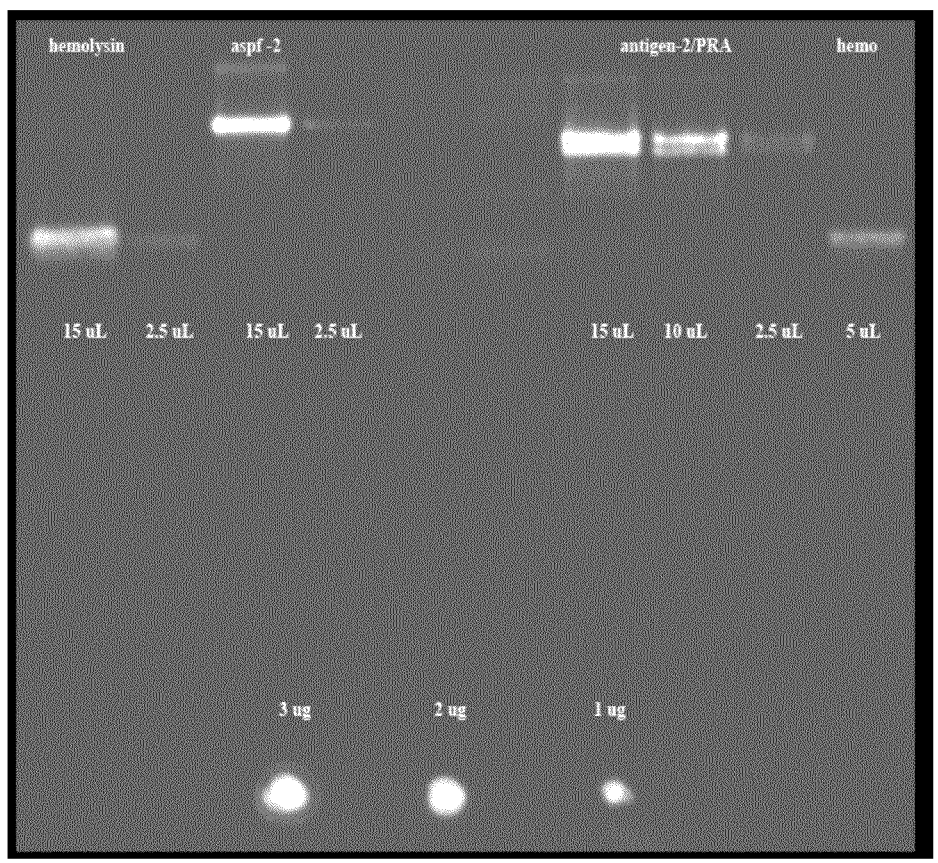
FIG. 8 represents an exemplary Western blot of separated lysed yeast cells containing and expressing genes for hemolysin, aspf2 or antigen-2/PRA.

FIG. 8 illustrates an exemplary a Western Blot of extracts of yeasts containing and expressing Hemolysin (hemo), aspf 2, or antigen 2 (the *Coccidioides* protein described above).

The numbers indicate the amount of lysate separated by SDS-GEL electrophoresis. The blots were treated with a c-myc epitope specific antibody and the antibody detected using a secondary horse radish peroxidase antibody. Various amounts in micrograms (indicated by the numbers at the bottom of the figure) of c-myc peptide were spotted.

Antigen 2/proline-rich antigen has been previously shown to be protective in murine models of coccidiomycosis. Thus antigen 2 was chosen. Published DNA and predicted amino acid sequences were used to design PCR primers to amplify the ORF from the Cox cDNA library (SEQ ID NOs:12 and 13). The DNA and amino acid sequences of antigen 2 are presented in diagram form, data not shown. An 18 amino acid signal sequence was predicted by PSORTII (psort.nibb.ac.jp/cgi-bin), but was not removed as PSORTII also predicted that the protein would be cell wall bound, most likely GPI anchored. This prediction suggests that the protein would not be secreted by the *S. cerevisiae*.

Exemplary conditions used to amplify antigen 2 from the cDNA library were as follows: 25 μL reactions were performed in PCR Ready Bead tubes (Amersham Pharmacia) containing 500 ng of cDNA library, 2 μM primers, and 13 μL sterile water. Reactions were performed using the Perkin Elmer 2400 Thermocycler (PE Applied Biosystems) under the following conditions: an initial cycle at 94° C. for 5 min, 30 cycles at 94° C. for 1 min, 50° C. for 1 min and 72° C. for 1 min, and a final extension at 72° C. for 7 min. As previously discussed, PCR reactions were separated and a band of approximately 582 bases corresponding to the amplified antigen 2 ORF was excised. The band was excised from the gel, purified and ligated into pCR 2.1. The ligated vector was used to transform competent *E. coli* cells and vector DNA isolated from 5 mL mini cultures using standard alkaline lysis techniques. DNA isolated from several miniprep isolates was digested with EcoRI to confirm the presence of the 582 base antigen 2 insert. Only one isolate contained the antigen 2 insert.

Several isolates were grown, cells harvested, plasmid DNA isolated and the DNA sequence of the antigen 2 insert determined. A comparison of the sequence obtained empirically with the published sequence is shown in SEQ ID NOs:14 and 15. There were no apparent PCR errors.

SEQ ID NOs:12 and 13

```
atg cag ttc tct cac gct ctc atc gct ctc gtc gct gcc ggc ctc gcc    48
Met Gln Phe Ser His Ala Leu Ile Ala Leu Val Ala Ala Gly Leu Ala
1               5                   10                  15 agt gcc cag ctc cca gac atc cca cct tgc gct ctc aac tgc ttc gtt    96
Ser Ala Gln Leu Pro Asp Ile Pro Pro Cys Ala Leu Asn Cys Phe Val
            20                  25                  30 gag gct ctc ggc aac gat ggc tgc act cgc ttg acc gac ttc aag tgc   144
Glu Ala Leu Gly Asn Asp Gly Cys Thr Arg Leu Thr Asp Phe Lys Cys
        35                  40                  45 cac tgc tcc aag cct gag ctc cca gga cag atc act cct tgc gtt gag   192
His Cys Ser Lys Pro Glu Leu Pro Gly Gln Ile Thr Pro Cys Val Glu
    50                  55                  60 gag gcc tgc cct ctc gac gcc cgt atc tcc gtc tcc aac atc gtc gtt   240
Glu Ala Cys Pro Leu Asp Ala Arg Ile Ser Val Ser Asn Ile Val Val
65                  70                  75                  80 gac cag tgc tcc aag gcc ggt gtc cca att gac atc cca cca gtt gac   288
Asp Gln Cys Ser Lys Ala Gly Val Pro Ile Asp Ile Pro Pro Val Asp
            85                  90                  95 acc acc gcc gct ccc gag cca tcc gag acc gct gag ccc acc gct gag   336
Thr Thr Ala Ala Pro Glu Pro Ser Glu Thr Ala Glu Pro Thr Ala Glu
            100                 105                 110 cca acc gag gag ccc act gcc gag cct acc gct gag ccc acc gct gag   384
Pro Thr Glu Glu Pro Thr Ala Glu Pro Thr Ala Glu Pro Thr Ala Glu
        115                 120                 125 ccg act tca gag ccc acc gag gag ccc act gcc gtc cca acc ggc act   432
Pro Thr Ser Glu Pro Thr Glu Glu Pro Thr Ala Val Pro Thr Gly Thr
    130                 135                 140 ggc ggt ggt gtc ccc act ggc acc ggt tcc ttc acc gtc act ggc aga   480
Gly Gly Gly Val Pro Thr Gly Thr Gly Ser Phe Thr Val Thr Gly Arg
145                 150                 155                 160 cca act gcc tcc acc cca gct gag ttc cca ggt gct ggc tcc aac gtc   528
Pro Thr Ala Ser Thr Pro Ala Glu Phe Pro Gly Ala Gly Ser Asn Val
            165                 170                 175 cgt gcc agc gtt ggc ggc att gct gct gct ctc ctc ggt ctc gct gcc   576
Arg Ala Ser Val Gly Gly Ile Ala Ala Ala Leu Leu Gly Leu Ala Ala
            180                 185                 190 tac ctg                                                           582
Tyr Leu
```

SEQ ID NO: 14: Antigen-2
ATGCAGTTCTCTCACGCTCTCATCGCTCTCGTCGCTGCCGGCCTCGCCAGTGCCCAGCTCCCAGACATC

CCACCTTGCGCTCTCAACTGCTTCGTTGAGGCTCTCGGCAACGATGGCTGCACTCGCTTGACCGACTTC

AAGTGCCACTGCTCCAAGCCTGAGCTCCCAGGACAGATCACTCCTTGCGTTGAGGAGGCCTGCCCTCT

CGACGCCCGTATCTCCGTCTCCAACATCGTCGTTGACCAGTGCTCCAAGGCCGGTGTCCCAATTGACAT

CCCACCAGTTGACACCACCGCCGCTCCCGAGCCATCCGAGACCGCTGAGCCCACCGCTGAGCCAACCG

AGGAGCCCACTGCCGAGCCTACCGCTGAGCCCACCGCTGAGCCGACTCATGAGCCCACCGAGGAGCC

CACTGCCGTCCCAACCGGCACTGGCGGTGGTGTCCCCACTGGCACCGGTTCCTTCACCGTCACTGGCA

GACCAACTGCCTCCACCCCAGCTGAGTTCCCAGGTGCTGGCTCCAACGTCCGTGCCAGCGTTGGCGGC

ATTGCTGCTGCTCTCCTCGGTCTCGCTGCCTACCTG

SEQ ID NO: 15: Antigen-2 PCR
ATGCAGTTCTCTCACGCTCTCATCGCTCTCGTCGCTGCCGGCCTCGCCAGTGCCCAGCTCCCAGACATC

CCACCTTGCGCTCTCAACTGCTTCGTTGAGGCTCTCGGCAACGATGGCTGCACTCGCTTGACCGACTTC

AAGTGCCACTGCTCCAAGCCTGAGCTCCCAGGACAGATCACTCCTTGCGTTGAGGAGGCCTGCCCTCT

CGACGCCCGTATCTCCGTCTCCAACATCGTCGTTGACCAGTGCTCCAAGGCCGGTGTCCCAATTGACAT

CCCACCAGTTGACACCACCGCCGCTCCCGAGCCATCCGAGACCGCTGAGCCCACCGCTGAGCCAACCG

AGGAGCCCACTGCCGAGCCTACCGCTGAGCCCACCGCTGAGCCGACTCATGAGCCCACCGAGGAGCC

CACTGCCGTCCCAACCGGCACTGGCGGTGGTGTCCCCACTGGCACCGGTTCCTTCACCGTCACTGGCA

GACCAACTGCCTCCACCCCAGCTGAGTTCCCAGGTGCTGGCTCCAACGTCCGTGCCAGCGTTGGCGGC

ATTGCTGCTGCTCTCCTCGGTCTCGCTGCCTACCTG

The DNA of the isolate was excised from the pCR 2.1 vector and the salient portions of the vector was determined to ensure the correct alignment of the ORF with the TATA box and the c-myc tag, as described previously. Published DNA and predicted amino acid sequences were used to design PCR primers to amply the ORF from the cDNA library for antigen 2.

In one exemplary method an empty vector control for animal models was designed as previously indicated; that is, the pYEX-BX vector containing the c-myc tag but lacking a *C. immitis* gene of interest. Several isolates were grown, cells harvested, plasmid DNA isolated and the DNA sequence of the c-myc control insert were determined. The DNA sequence of pertinent portions of the vector was determined to ensure the correct alignment of the c-myc with the TATA box.

Transformation of *S. cerevisiae* was performed as previously described. After obtaining at least 10 transformants for each *C. immitis* gene of interest, cells are grown and induced the expression of each gene by adding copper sulfate. Uninduced and induced cells were harvested by centrifugation, lysed in SDS-gel lysis buffer and the protein concentration of each extract determined. Equal protein amounts of each lysate were separated by SDS-PAGE and the separated proteins transferred to membranes. The presence of the c-myc tagged proteins was detected by Western blot analysis using an anti-c-myc antibody. Then the transformants were grown as previously described. Once transformants of each construct were isolated, the proteins were expressed via copper induction as previously discussed. Then cultures were grown overnight at 30° C. with shaking. These cultures were used for the identification of transformants that were expressing each of the *C. immitis* proteins.

Identification of transformants expressing each *C. immitis* protein. Induced and uninduced cultures were harvested after overnight incubation by centrifugation at 550×g for 10 minutes. Each cell pellet was washed with 25 mL ice cold water to remove any residual medium and the cells were harvested again by centrifugation. Each pellet was resuspended in 1 mL of ice cold water and divided into two 1.5 mL eppendorf tubes for centrifugation. After the removal of the supernatant, one tube was frozen at −80° C. for storage and the other was lysed for protein determination. Cells were lysed in the following manner: 100 μL of glass beads were added to the tube containing cells followed by the addition of 200 μL 2× sample lysis buffer (0.1M Tris, pH 6.8, 20% (v/v) glycerol, 4% (w/v) SDS, 6.2 mg DTT). Tubes were mixed by vortexing for 1 min and boiled for 3 min to resuspend and lyse the cells. Debris was removed by centrifugation and the cleared supernatant was transferred to a new tube. The cleared lysate was used for western blots.

Cell lysates were loaded into the wells of SDS page gels and expression of the *C. immits* proteins were determined by exemplary western blot procedures known in the art. Each of three *C. immitis* genes from a cDNA library using gene-specific PCR primers was obtained. The DNA encoding each ORF was sequenced to confirm that the correct gene had been cloned and that no PCR errors were introduced. The ORF of each gene was inserted into the copper inducible vector pYEX-BX. Each ligated vector was sequenced to ensure the correct position of the gene relative to the TATA box and that the c-myc tag was in frame with each protein.

Example 3

In certain exemplary methods, the fungal organism Cryptococcosis was analyzed (see exemplary schematic FIG. 9)

Cryptococcosis model. In one exemplary method, an inhalation model of cryptococcosis was chosen because 1) it most closely mimics the natural course of *C. neoformans* infection, 2) it is highly reproducible and 3) it is commonly used to assess virulence. The inhalation cryptococcosis model performed was essentially as previously described (see: Cox, G. M., Mukherjee, J., Cole, G. T., et al. Urease as a virulence factor in experimental cryptococcosis. Infect Immun. (2000) 68:443-448. incorporated herein by reference).

To test the in vivo efficacy of each vaccine formulation to protect vaccinated animals against a challenge of *C. neoformans*, mice are vaccinated with various vaccine formulations, and challenged with *C. neoformans*, and monitored for protection.

Organism. *C. neoformans* H99 was used as the challenge organism for all infections. *C. neoformans* H99 yeast for the inoculum was prepared as follows. Briefly, *C. neoformans* strain H99 was grown at 30° C. with shaking for two days in liquid YPD medium. The cells were harvested by centrifugation, washed in endotoxin-free PBS, and resuspended in endotoxin-free PBS. The cells were counted on a hemocytometer and diluted to $1\times10^6$ cells per ml. The inoculum was serially diluted and plated onto YPD to confirm the number of cells that are inoculated.

Mice. Four-week-old female A/J Cr mice were obtained from Charles River Laboratories for the inhalation model of cryptococcosis. Mice are commonly used for virulence assays with the serotype A strain, H99, and have been used in previous assessments of antibody protection against *C. neoformans*.

Briefly, mice from a specific pathogen-free colony were vaccinated with 150 μL of each yeast vaccine preparation on day 21, 14 and 7 before being challenged with 50 uL containing $5\times10^4$ H99 *C. neoformans* cells.

Figure 9:
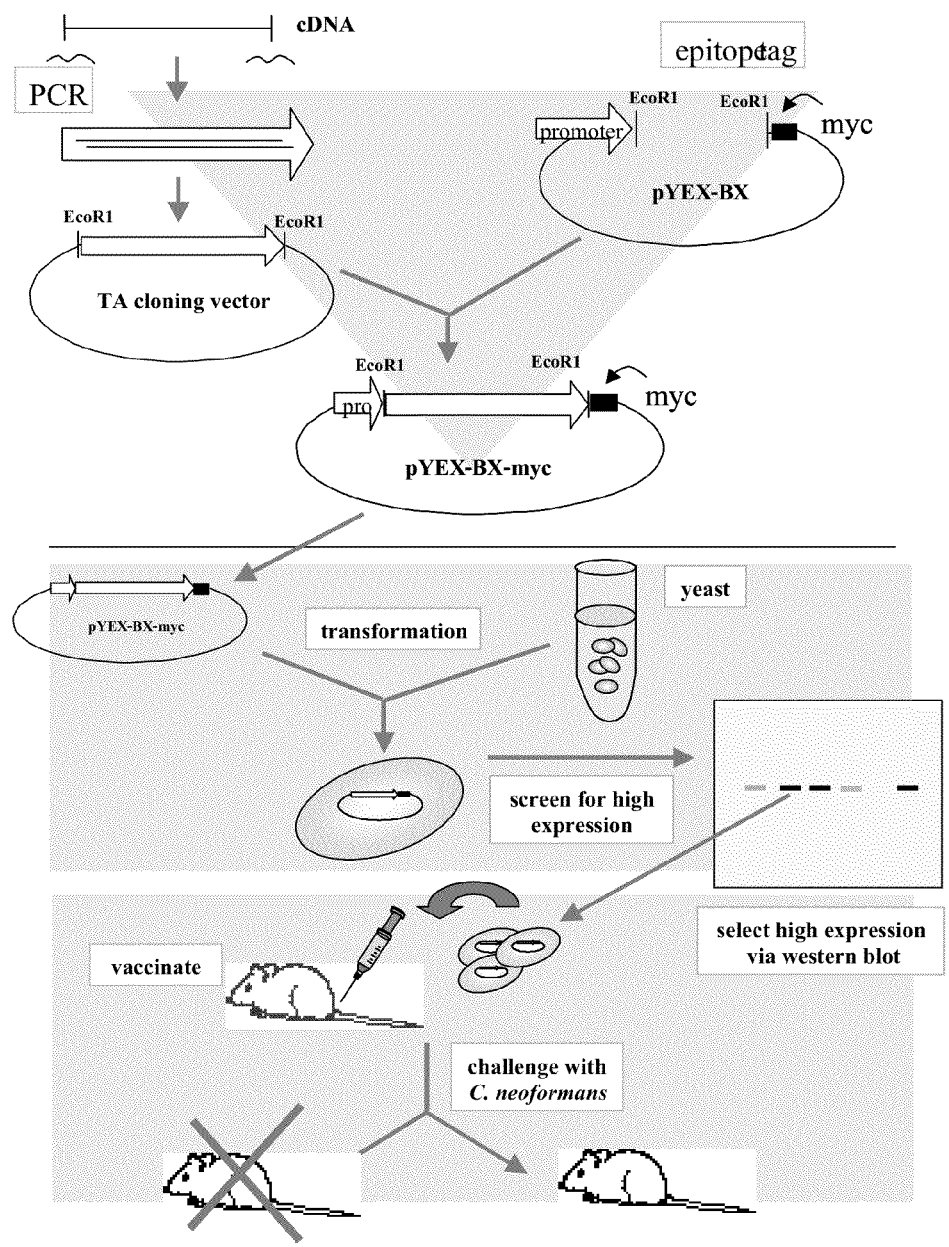
FIG. 9 illustrates an exemplary schematic of a method to test a vaccine disclosed herein.

In one exemplary method, experiments were performed to determine whether yeast strains expressing *C. neoformans* proteins could be used as a vaccine against *C. neoformans* infections. cDNA of certain genes whose proteins are likely to be important in infection were generated. Then yeast cells were transformed with each cDNA and select strains that express high levels of each putative antigen. Finally, each vaccine formulation was tested for its ability to protect vaccinated mice against a challenge of *C. neoformans*. FIG. 9 represents a schematic of these experiments.

DNA vector construction and Yeast Transformation were performed in this example as previously described. Primers are listed in Table 4 (SEQ ID NOs: 30-41). Then the cloned genes were used as template and amplified each gene using the gene-specific PCR primers. The DNA sequence of each ligated pYEX-BX vector containing a gene of interest was determined to ensure that the correct gene was cloned, the start codon was on the same DNA strand as the TATA box (initiation of transcription), and that the c-myc tag was in frame with each gene followed by two stop codons (TGA TAA).

Cloning of CDA: Published DNA was used and predicted amino acid sequences to design PCR primers to amplify the ORF from the clone, as described above. The DNA and amino acid sequences of CDA are presented in diagram form in SEQ ID NOs: 16-17. The positions of the 5' and 3' primers use to obtain the predicted PCR product are shown. A 19 amino acid signal sequence was predicted by PSORTII (psort.nibb.ac.jp/cgi-bin). The signal sequence was subsequently removed as PSORTII predicted that the protein would be extra-cellular, which suggested that the protein would be secreted by the *S. cerevisiae* if the signal sequence was left intact. A methionine was added before the 20th amino acid (Serine) to ensure that the protein would be translated.

```
                                                          SEQ ID NOs: 16 and 17
- DNA and corresponding amino acid sequence of CDA
atg aag ttc atc aca agc ctc ttt gcc gtt ctt gcc att ctc tca agt       48
Met Lys Phe Ile Thr Ser Leu Phe Ala Val Leu Ala Ile Leu Ser Ser
1               5                   10                  15 gtc tct gct tct cct acc atg aag aaa cgt gcg acc gtc gaa act atc       96
Val Ser Ala Ser Pro Thr Met Lys Lys Arg Ala Thr Val Glu Thr Ile
            20                  25                  30 aac aac tgt aat cag cag ggc act gtt gct ctg acc ttt gac gat ggc      144
Asn Asn Cys Asn Gln Gln Gly Thr Val Ala Leu Thr Phe Asp Asp Gly
                35                  40                  45 cct tac aat tac gaa gcc caa gtt gct tct gcc ctt gac ggg ggt aag      192
Pro Tyr Asn Tyr Glu Ala Gln Val Ala Ser Ala Leu Asp Gly Gly Lys
    50                  55                  60 ggt act ttt ttc ctc aac ggc gcg aat tat gtc tgc atc tac gac aag      240
Gly Thr Phe Phe Leu Asn Gly Ala Asn Tyr Val Cys Ile Tyr Asp Lys
65                  70                  75                  80 gcc gat gaa atc aga gct ttg tat gat gcc ggc cac act ctt ggt tct      288
Ala Asp Glu Ile Arg Ala Leu Tyr Asp Ala Gly His Thr Leu Gly Ser
                85                  90                  95 cac act tgg tct cac gcc gac ctt acc cag tta gat gaa tcc ggg atc      336
His Thr Trp Ser His Ala Asp Leu Thr Gln Leu Asp Glu Ser Gly Ile
            100                 105                 110 aac gag gaa ctc tcc aag gtc gaa gat gcc ttt gtc aag atc ctt ggt      384
Asn Glu Glu Leu Ser Lys Val Glu Asp Ala Phe Val Lys Ile Leu Gly
        115                 120                 125 gtc aag cct cga tac ttc cga ccc cct tac ggt aac atc aac gac aac      432
Val Lys Pro Arg Tyr Phe Arg Pro Pro Tyr Gly Asn Ile Asn Asp Asn
130                 135                 140
```

-continued

```
gtc ttg aac gtc ctc agt gaa agg ggt tac acg aag gtg ttt ttg tgg    480
Val Leu Asn Val Leu Ser Glu Arg Gly Tyr Thr Lys Val Phe Leu Trp
145                 150                 155                 160 tct gat gac act ggg gat gcc aac ggc gag tcg gtc agt tac tcc gag    528
Ser Asp Asp Thr Gly Asp Ala Asn Gly Glu Ser Val Ser Tyr Ser Glu
                165                 170                 175 ggg gta ttg gac aac gtt atc cag gat tat cct aac cct cat ctt gtc    576
Gly Val Leu Asp Asn Val Ile Gln Asp Tyr Pro Asn Pro His Leu Val
            180                 185                 190 ctt gat cac tct acc atc gag acg acc tcc tcc gag gtt ctc cct tac    624
Leu Asp His Ser Thr Ile Glu Thr Thr Ser Ser Glu Val Leu Pro Tyr
        195                 200                 205 gct gta ccc aag ctc cag agt gct ggc tac caa ctg gtc act gtc ggt    672
Ala Val Pro Lys Leu Gln Ser Ala Gly Tyr Gln Leu Val Thr Val Gly
    210                 215                 220 gaa tgt ctc ggc acc gac gaa tct cct tac gaa tgg gtt gat tgc cct    720
Glu Cys Leu Gly Thr Asp Glu Ser Pro Tyr Glu Trp Val Asp Cys Pro
225                 230                 235                 240 gga gag agg gat agc tct tgg caa tgc                                747
Gly Glu Arg Asp Ser Ser Trp Gln Cys
                245
```

The following conditions were used to amplify CDA from the plasmid: 25 µL reactions were performed in PCR Ready Bead tubes (Amersham Pharmacia) containing 500 ng of the plasmid containing CDA, 2 µM primers, and 13 µL sterile water. Reactions were performed using the Perkin Elmer 2400 Thermocycler (PE Applied Biosystems) under the following conditions: an initial cycle at 94° C. for 5 min, 30 cycles at 94° C. for 1 min, 50° C. for 1 min and 72° C. for 1 min, and a final extension at 72° C. for 7 min.

The PCR reactions were separated using agarose gel electrophoresis and a band of approximately 744 bases corresponding to the amplified CDA ORF containing a 3' c-myc tag was excised. The band was purified and ligated into pCR 2.1. The ligated vector was used to transform competent E. coli cells and vector DNA isolated from 5 mL mini cultures using standard alkaline lysis techniques. DNA isolated from several miniprep isolates was digested with EcoRI to confirm the presence of the 744 base CDA/c-myc insert.

In one exemplary method, the DNA of the isolate was excised from the pCR 2.1 vector and ligated into the pYEX-BX vector as previously described and the salient portions of the vector was determined to ensure the correct alignment of the ORF with the TATA box One exemplary method concerns cloning of Laccase: As indicated above, the same strategy to clone Laccase (lac) from a plasmid containing the gene as used to clone CDA. DNA sequence and plasmid DNA was used to predicted the amino acid sequences to design PCR primers to amplify the ORF plus the c-myc tag from the plasmid. The DNA and amino acid sequences are presented in diagram form in SEQ ID NOs:18 and 19. The positions of the 5' and 3' primers used to obtain the predicted PCR product are shown. A 20 amino acid signal sequence was predicted by PSORTII (psort.nibb.ac.jp/cgi-bin). The signal sequence was subsequently removed as PSORTII predicted that the protein would be extracellular, which suggested that the protein would be secreted by the S. cerevisiae if the signal sequence was left intact. An endogenous methionine at amino acid 21 (Glutamic acid) was used as the first amino acid in the new protein to ensure that the protein would be translated.

```
atg cgg gga gta gtc aag ctc ttc ttt cta tct tgt tcc ctc gtt tcg    48
Met Arg Gly Val Val Lys Leu Phe Phe Leu Ser Cys Ser Leu Val Ser
1                   5                   10                  15 ctg gtc agc agc gag gag act ggc aag tcg cca acc gcg aac tat gac    96
Leu Val Ser Ser Glu Glu Thr Gly Lys Ser Pro Thr Ala Asn Tyr Asp
                20                  25                  30 cat tat atg ccg aag gcg aca gca acc att gat cct agt gta ttc gct    144
His Tyr Met Pro Lys Ala Thr Ala Thr Ile Asp Pro Ser Val Phe Ala
            35                  40                  45 ctt tca aat gac ttt gaa ata aca gat gtt ccg acg acg agg gag tat    192
Leu Ser Asn Asp Phe Glu Ile Thr Asp Val Pro Thr Thr Arg Glu Tyr
        50                  55                  60 acc ttc gat atc acc aaa gcg ttg gcc agc cct gat ggt tat gaa cga    240
Thr Phe Asp Ile Thr Lys Ala Leu Ala Ser Pro Asp Gly Tyr Glu Arg
65                  70                  75                  80 gag gtt tac gtt gtc aac aac atg ttc cct gga cct gtg ata gag gct    288
Glu Val Tyr Val Val Asn Asn Met Phe Pro Gly Pro Val Ile Glu Ala
                85                  90                  95
```

```
aac acc ggg gat act att atc gta cat gtc aac aat cat ttg gag gaa      336
Asn Thr Gly Asp Thr Ile Ile Val His Val Asn Asn His Leu Glu Glu
            100                 105                 110 gga caa agt atc cac tgg cat ggt ttg cgg cag ctt ggc acg gct ttc      384
Gly Gln Ser Ile His Trp His Gly Leu Arg Gln Leu Gly Thr Ala Phe
            115                 120                 125 atg gac ggt gtc cct ggt ata aca cag tgt cct att ccc cct gga agc      432
Met Asp Gly Val Pro Gly Ile Thr Gln Cys Pro Ile Pro Pro Gly Ser
130                 135                 140 tca ttt acc tac caa ttc acc gta agc cat cag tca ggc acg ttt tgg      480
Ser Phe Thr Tyr Gln Phe Thr Val Ser His Gln Ser Gly Thr Phe Trp
145                 150                 155                 160 tgg cat tcc cat tat tcc aat tcc atg gcc gac ggc att tgg ggc ccc      528
Trp His Ser His Tyr Ser Asn Ser Met Ala Asp Gly Ile Trp Gly Pro
                165                 170                 175 tta att atc cat tcg ccc aat gaa ccc ctc caa agg gga cga gac tat      576
Leu Ile Ile His Ser Pro Asn Glu Pro Leu Gln Arg Gly Arg Asp Tyr
            180                 185                 190 gac gag gat cga atc gtt ttt ata act gac tgg gtg cat gac aac tca      624
Asp Glu Asp Arg Ile Val Phe Ile Thr Asp Trp Val His Asp Asn Ser
        195                 200                 205 gaa gtc gtt att gca gct cta gct act cca gaa ggg tac aaa gga agc      672
Glu Val Val Ile Ala Ala Leu Ala Thr Pro Glu Gly Tyr Lys Gly Ser
    210                 215                 220 cct gct ccg cca caa ggt gat gcg att ctc atc aat gga cgt ggc caa      720
Pro Ala Pro Pro Gln Gly Asp Ala Ile Leu Ile Asn Gly Arg Gly Gln
225                 230                 235                 240 acc aac tgc aca gcc act ggt tcc tcc tca tgc acc tat ccg cct cct      768
Thr Asn Cys Thr Ala Thr Gly Ser Ser Ser Cys Thr Tyr Pro Pro Pro
                245                 250                 255 ccc gag att cac gtg cca gtc aat tgc agg gtt cgt ctg cgc ttt atc      816
Pro Glu Ile His Val Pro Val Asn Cys Arg Val Arg Leu Arg Phe Ile
            260                 265                 270 agt gcg acc gcc cat ccc atg tac cgc ata act atc gac aac cac cct      864
Ser Ala Thr Ala His Pro Met Tyr Arg Ile Thr Ile Asp Asn His Pro
        275                 280                 285 ttg gaa gtt gtg gaa acc gac ggt aca gcc gtc tat ggg ccc aca gtc      912
Leu Glu Val Val Glu Thr Asp Gly Thr Ala Val Tyr Gly Pro Thr Val
    290                 295                 300 cat gaa atc tcc att gca cct ggg gaa cgg tac tct gca att atc aac      960
His Glu Ile Ser Ile Ala Pro Gly Glu Arg Tyr Ser Ala Ile Ile Asn
305                 310                 315                 320 acc tca gaa ggg aag gaa ggt gat gcg ttc tgg ctg agg aca agt gtt     1008
Thr Ser Glu Gly Lys Glu Gly Asp Ala Phe Trp Leu Arg Thr Ser Val
                325                 330                 335 gct ctg ggc tgt atg ttt ggt gga ata gat cag gtg gga ttg gcg gtt     1056
Ala Leu Gly Cys Met Phe Gly Gly Ile Asp Gln Val Gly Leu Ala Val
            340                 345                 350 gtg agg tat acg ggt aat gga atg gtt agt act gaa gag cct caa act     1104
Val Arg Tyr Thr Gly Asn Gly Met Val Ser Thr Glu Glu Pro Gln Thr
        355                 360                 365 act gct tgg agt gat cta gcg gga gct aca act cct tgt gct gga ctg     1152
Thr Ala Trp Ser Asp Leu Ala Gly Ala Thr Thr Pro Cys Ala Gly Leu
    370                 375                 380 gac caa aca tat act ctt tca cca cga gag agt ttt agt gca cct cgt     1200
Asp Gln Thr Tyr Thr Leu Ser Pro Arg Glu Ser Phe Ser Ala Pro Arg
385                 390                 395                 400 gaa ttt tca caa agc cat gtc ttc aat agc cag cga gga gcc ttt gtg     1248
Glu Phe Ser Gln Ser His Val Phe Asn Ser Gln Arg Gly Ala Phe Val
                405                 410                 415
```

-continued

| | | |
|---|---|---|
| aat gtt tat ggc aac acc ttc caa ggt tat ggg ttt aac aat atc tca<br>Asn Val Tyr Gly Asn Thr Phe Gln Gly Tyr Gly Phe Asn Asn Ile Ser<br>420                        425                        430 | 1296 |
| tat cag aac caa atc ttc aac cct cta ctt tca atc gtc caa cgc ggt<br>Tyr Gln Asn Gln Ile Phe Asn Pro Leu Leu Ser Ile Val Gln Arg Gly<br>       435                       440                     445 | 1344 |
| ggc tct tgc gag agc aca cta gta gcc agt aca act ttc ccc gac ctc<br>Gly Ser Cys Glu Ser Thr Leu Val Ala Ser Thr Thr Phe Pro Asp Leu<br>450                        455                        460 | 1392 |
| gga tca ggg aac att atc atc aac aat ctt gat ggc gtt atc gac cat<br>Gly Ser Gly Asn Ile Ile Ile Asn Asn Leu Asp Gly Val Ile Asp His<br>465                        470                     475               480 | 1440 |
| cct tac cac ctg cac ggc aac gag ttc cag gtg ata gga cga gga act<br>Pro Tyr His Leu His Gly Asn Glu Phe Gln Val Ile Gly Arg Gly Thr<br>                  485                     490                     495 | 1488 |
| gga gct ctc agc ctt gat aac ctg aca aat att gac ttc aat ttg gac<br>Gly Ala Leu Ser Leu Asp Asn Leu Thr Asn Ile Asp Phe Asn Leu Asp<br>            500                        505                     510 | 1536 |
| aac cct gtg aga aag gat acc ctc tgg ata cag ggc gga agt tgg gtg<br>Asn Pro Val Arg Lys Asp Thr Leu Trp Ile Gln Gly Gly Ser Trp Val<br>       515                        520                     525 | 1584 |
| gta ctg agg atc acg acg gat aac cct gga gtt tgg gcc ttg cac tgt<br>Val Leu Arg Ile Thr Thr Asp Asn Pro Gly Val Trp Ala Leu His Cys<br>530                        535                     540 | 1632 |
| cat att ggg tgg cat ctt act gag gga aag ttg gct gtg gtt gtc att<br>His Ile Gly Trp His Leu Thr Glu Gly Lys Leu Ala Val Val Val Ile<br>545                        550                     555               560 | 1680 |
| caa cca ggt gcg att gga cat atg gag ggc ccc gag tct tgg acg aat<br>Gln Pro Gly Ala Ile Gly His Met Glu Gly Pro Glu Ser Trp Thr Asn<br>                  565                     570                     575 | 1728 |
| ctc tgt gct aac act gat ccc aat gca ttt gga ccc gca cga cgc tca<br>Leu Cys Ala Asn Thr Asp Pro Asn Ala Phe Gly Pro Ala Arg Arg Ser<br>            580                        585                     590 | 1776 |
| cct tct cca tct att caa tcc tct aag aca tcc act ttc cag tat ctg<br>Pro Ser Pro Ser Ile Gln Ser Ser Lys Thr Ser Thr Phe Gln Tyr Leu<br>       595                        600                     605 | 1824 |
| cgc gaa gtg aaa ggg aag gtc gtt aaa cgt aga ggt gct cga gag gcg<br>Arg Glu Val Lys Gly Lys Val Val Lys Arg Arg Gly Ala Arg Glu Ala<br>610                        615                     620 | 1872 |

The following conditions were used to amplify laccase from the plasmid: 25 µL reactions were performed in PCR Ready Bead tubes containing 500 ng of plasmid containing Laccase, 2 µM primers, and 13 µL sterile water. Reactions were performed using a Perkin Elmer 2400 Thermocycler under the following conditions: an initial cycle at 94° C. for 5 min, 30 cycles at 94° C. for 1 min, 50° C. for 1 min, 72° C. for 1 min, and a final extension at 72° C. for 7 min.

The PCR reactions were separated, isolated and digested with EcoRI as previously described to confirm the presence of the 1857 base Lac/c-myc insert.

Several isolates were grown, cells harvested, plasmid DNA isolated and the DNA sequence of the Lac insert determined. The DNA of the isolate was excised from the pCR 2.1 vector and the DNA band encoding the Laccase ORF could be isolated, data not shown. This DNA fragment was then ligated into the pYEX-BX vector as described and then used to transform competent E. coli and the plasmid DNA isolated by standard alkaline lysis mini-preps. The DNA sequence of salient portions of the vector was determined to ensure the correct alignment of the ORF with the TATA box.

An empty vector control was made and used as previously described in methods.

Transformation of S. cerevisiae was made and used as previously described in methods.

Identification of yeast transformants expression each C. Neoformans protein. After obtaining transformed S. cerevisiae cells that contained each gene of interest 5 transformants were screened for each gene of interest were screened to determine the expression of each gene and the transformants were isolated as previously described. Once transformants containing each construct were isolated, each of the proteins was expressed as described previously. Then transformants expressing each C. neoformans protein were identified by one exemplary method previously disclosed.

Expression of C. neoformans proteins were determined by an exemplary western blot technique known in the art. Ten CDA transformants were screened to obtain a transformant that was positive for induction via copper. Transformant 10 was chosen for vaccine production as it had the most protein as determined by counting pixels. Five Lac transformants were screened to obtain a transformant that was positive for induction via copper. Please note that the top band is of the correct size. Transformant number 2 had the least amount of protein in the un-induced sample and the most (by counting pixels) in the copper induced sample Growth of transformants: Transformants that were determined to produce a protein of the correct molecular weight were grown in YNB minus uracil for 2-3 days at 30° C. with shaking. Once the cultures were in stationary phase, the cells were counted and frozen in 50% glycerol at a final concentration of 1×108 c/mL (10 yeast units) and stored at −80° C. until use.

Figure 10:
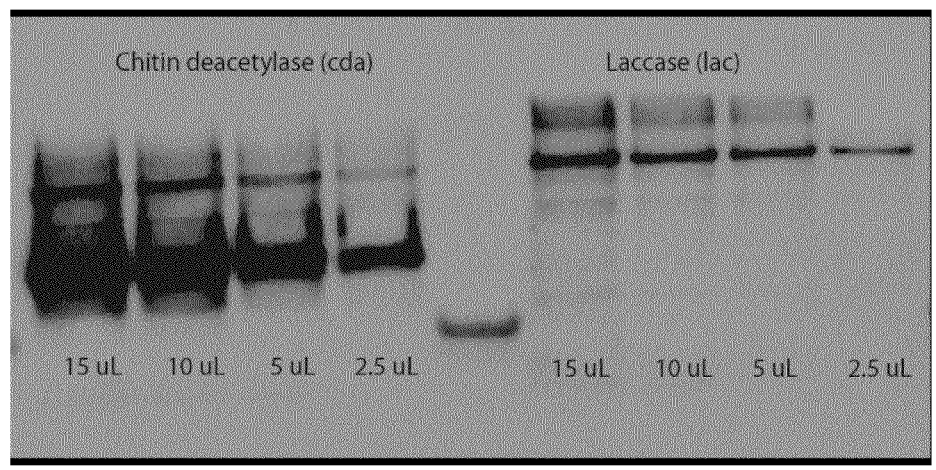
FIG. 10. represents an exemplary electrophoresis gel of separated molecules of yeast lysates containing and expressing the gene encoding Chitin deacetylase and Laccase.

Yeast cells containing and expressing chitin deacetylase or laccase were harvested and lysed as described. The indicated number of microliters of each extract were separated by SDS-PAGE, transfer to membranes and the position of each protein detected by Western blot analysis as described. The results of the western blot are shown in FIG. 10. Lane 1-4 are various amounts in microliters of lysed yeast cells expressing chitin deacetylase (cda; MW.26.6 kDa), while lanes 6-9 are various amounts in microliters of lysed yeast cells expressing laccase (lac; MW. 67.4 kDa).

Figure 11:
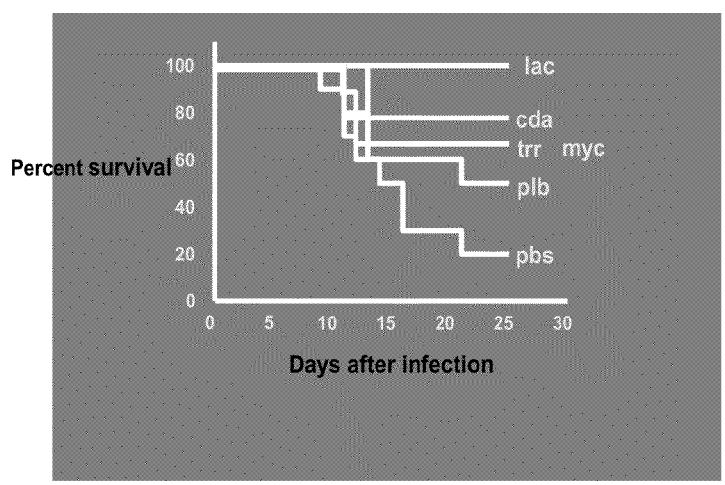
FIG. 11 illustrates an exemplary survival curves for mice infected in vitro. with *Cryptococcosis neoformans*

FIG. 11 represents exemplary linear survival plots in an animal model after exposure to a challenge fungal organism. Mice were vaccinated with yeast cells containing and expressing the DNA encoding laccase, (lac), chitin deacetylase (cda), the MYC yeast control, PBS, trr and plb (two additional *C. neoformans* proteins) as described above on days 21, 14 and 7 prior to challenge by *C. neoformans* H99 cells. Mice were weighed daily and mice that had lost >15% of their body weight euthanized. Note that mice vaccinated with lac-containing yeast were 100% protected ($p<<0.05$) while those vaccinated with cda containing yeast were 80% protected ($p<0.05$) as were those vaccinated with MYC (empty vector control). These results demonstrate that mice vaccinated with yeast expressing either laccase or chitin deacetylase were highly protected against a challenge of *C. neoformans*.

TABLE 1

Candidate antigens

| Protein | Number of amino acids | Base pairs of the ORF | Accession numbers |
|---|---|---|---|
| fos-1 | 708 | 2,124 | Protein: AAK27436 DNA: AF257496 |

TABLE 1-continued

Candidate antigens

| Protein | Number of amino acids | Base pairs of the ORF | Accession numbers |
|---|---|---|---|
| hemolysin | 131 | 721 | Protein: BAA03951.1 DNA: D16501 |
| catalase | 728 | 2,184 | Protein: AAB71223 DNA: U97574 |
| abr-1 | 664 | 1,992 | Protein: AAF03353 DNA: AF116901 |
| rodA | 159 | 477 | Protein: AAB60172.1 DNA: U06121 |
| dpp-5 | 721 | 2,163 | Protein: AAB67282 DNA: L48074 |
| dpp-4 | 765 | 2,295 | Protein: AAC34310 DNA: U87950 |

TABLE 2

*Cryptococcus* antigens

| Protein | Number of amino acids | Base pairs of the ORF | Accession numbers |
|---|---|---|---|
| CDA—Chitan deacetylase | 250 | 750 | Protein: CAD10036 DNA: AJ414580 |
| CnFOS—histidine kinase | 1367 | 4101 | Protein: AAW42353 DNA: NA* |
| Lac—Laccase | 625 | 1875 | Protein: NA* DNA: L22866 |
| Plb—phospholipse B | 638 | 1914 | Protein: AAF65220.1 DNA: AF223383 |
| Ure—Urease | 833 | 2499 | Protein: AAC62257.1 DNA: AF006062 |

*NA—not available

TABLE 3

PCR primers

| | |
|---|---|
| 5' AspF2/Bam | 5'GGA TCC ATG CTT GTG GCC ACC CTC CCT 3' (SEQ ID NO: 20) |
| 3' AspF2/myc | 5'GAA TTC TTA TCA CTC GAG GTC TTC TTC GGA AAT CAA CTT AGT GCA ATG AAG CTG TCC ACC TTC ATG GGT ATG GC 3' (SEQ ID NO: 21) |
| 5'DppV/Bam | 5'GGA TTC ATG CTT ACA CCT GAG CAG CTA ATC ACT GCT CCA CGG 3' (SEQ ID NO: 22) |
| 3'DppV/myc | 5'GAA TTC TTA TCA CTC GAG GTC TTC TTC GGA AAT CAA CTT CTG TTC CGG GAC AAC GGT GTC CTC CAG GCT GAC GGC GTT GGG G 3' (SEQ ID NO: 23) |
| 5'Fos-1/SalI | 5'GTC GAC ATG GCC CTC GAC AAG GAG C 3' (SEQ ID NO: 24) |
| 3'Fos-1/myc | 5'CTG CAG TTA TCA CTC GAG GTC TTC TTC GGA AAT CAA CTT CTG TTC CAT CTT GGA TGA TTC CTC AAA AGC TGC CAC CAT CCG CGC TTC AGC CGC 3' (SEQ ID NO: 25) |
| 5'Hemo/Bam | 5'GGA TTC ATG GCA TCG TCA AGC TAC GCA CAG TGG 3' (SEQ ID NO: 26) |
| 3' Hemo/myc | 5'GAA TTC TTA TCA CTC GAG GTC TTC TTC GGA AAT CAA CTT CTG TTC ACA GTT GCC AAT GGC ACC ACC ATA CTT GTT CCA CGT TCC AAT TTC GAC CCA G 3' (SEQ ID NO: 27) |
| 5'RodA/SalI | 5'GTC GAC ATG AAG TTC TCT TTG AGC GCT GCT GTC CTC GC 3' (SEQ ID NO: 28) |

TABLE 3-continued

PCR primers

| | |
|---|---|
| 3'RodA/myc | 5'GAA TTC TTA TCA CTC GAG GTC TTC TTC GGA AAT CAA CTT CTG TTC CAG GAT AGA ACC AAG GGC AAT GCA AGG AAG ACC CAG TCC AAT GAG GG 3' (SEQ ID NO: 29) |
| PCR primers | |

TABLE 4

PCR primers

| | |
|---|---|
| 5' CDA/Bam | GGA TCC ATG TCT CCT ACC ATG AAG AAA CGT GCG (SEQ ID NO: 30) |
| 3' CDA/myc | GAA TTC TTA TCA CTC GAG GTC TTC TTC GGA AAT CAA CTT CTG TTC GCA TTG CCA AGA GCT ATC CCT CTC TCC AGG CAA ATC AAC CCA TTC G (SEQ ID NO: 31) |
| 5' CnFos/Sal | GTC GAC ATG TCC CTC CCC GAT GCC TAC CCT CCG GTC ATA GCC ACC (SEQ ID NO: 32) |
| 3' CnFos/myc | GAA TTC TTA TCA CTC GAG GTC TTC TTC GGA AAT CAA CTT CTG TTC ACT TCT GTT GGC CAT TTC AGC TTC CTG TCT CGC C (SEQ ID NO: 33) |
| 5' Lac/Bam | GGA TCC ATG GAG GAG ACT GGC AAG TCG CCA ACC GCG (SEQ ID NO: 34) |
| 3' Lac/myc | GAA TTC TTA TCA CTC GAG GTC TTC TTC GGA AAT CAA CTT CTG TTC CGC CTC TCG AGC ACC TCT ACG TTT AAC GAC CTT CCC TTT CAC TTC GCG CAG (SEQ ID NO: 35) |
| 5' Plb/Bam | GGA TCC ATG GCT GTT CCT CCC GAG ACT CCG CGG (SEQ ID NO: 36) |
| 3' Plb/myc | GAA TTC TTA TCA CTC GAG GTC TTC TTC GGA AAT CAA CTT CTG TTC AGT GAG AGA GCG CAT ACC ATT GAG CAA CAT TTC GTT GGC (SEQ ID NO: 37) |
| 5' TRR/Bam | GGA TCC ATG CAC TCC AAG GTT GTT ATC ATC GGC TCT GG (SEQ ID NO: 38) |
| 3' TRR/myc | GAA TTC TTA TCA CTC GAG GTC TTC TTC GGA AAT CAA CTT CTG TTC CTC CTT GTC AGT GCC GAA GTA GTG CTC GGC AGG GAC ATG CAC ATC TTC GGT CTG G (SEQ ID NO: 39) |
| 5' URE/Bam | GGA TCC ATG CAT CTC CTC CCG AGA GAA ACG (SEQ ID NO: 40) |
| 3' URE/myc | GTC GAC TTA TCA CTC GAG GTC TTC TTC GGA AAT CAA CTT CTG TTC GTA AAC GAA GTA TCT CCT GGT CAA TGG GAG TTT GTC GCG GGG TGG GAC (SEQ ID NO: 41) |
| PCR primers | |

\* \* \*

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising:
   a) non-viable yeast cells *Saccharomvces cerevisiae*; and
   b) an antigen from *Cryptococcus* laccase (Lac) comprising the amino acid sequence of SEQ ID NO:19 or positions 22-624 of SEQ ID NO:19 or chitin deacetylase (CDA) comprising the amino acid sequence of SEQ ID NO:17 or positions 20-249 of SEQ ID NO:19; and
   wherein the composition is formulated for administration to a subject, and wherein the composition induces a cell-mediated immune response in a subject.

2. The composition of claim 1, wherein the yeast cells were transformed to express the antigen.

3. The composition of claim 1, wherein the non-viable yeast cells were heat-killed.

4. The composition of claim 1, wherein the non-viable yeast cells were heat-killed at 56° C. for one hour.

5. The composition of claim 1, wherein the *Cryptococcus* is *Cryptococcus neoformans*.

6. The composition of claim 1, wherein the antigen is the laccase (Lac) antigen comprising the amino acid sequence of SEQ ID NO:19 or positions 22-624 of SEQ ID NO:19.

7. The composition of claim 1, wherein the yeast cells were transformed to express the antigen.

8. The composition of claim 1, wherein the Lac antigen has the amino acid sequence of SEQ ID NO:19.

9. The composition of claim 1, wherein the Lac antigen has the amino acid sequence of positions 22-264 of SEQ ID NO:19.

10. The composition of claim 1, wherein the antigen is the chitin deacetylase (CDA) antigen comprising the amino acid sequence of SEQ ID NO:17 or positions 20-249 of SEQ ID NO:17.

11. The composition of claim 1, wherein the CDA antigen comprises an amino acid sequence of SEQ ID NO:17.

12. The composition of claim 1, wherein the CDA antigen comprises an amino acid sequence positions 20-249 of SEQ ID NO:17.

* * * * *